(12) United States Patent
Wang et al.

(10) Patent No.: US 10,888,628 B2
(45) Date of Patent: *Jan. 12, 2021

(54) GENE THERAPY FOR TREATING HEMOPHILIA A

(71) Applicant: The Trustees of the University of Pennsylvania, Philadelphia, PA (US)

(72) Inventors: Lili Wang, Phoenixville, PA (US); James M. Wilson, Philadelphia, PA (US); Jenny Agnes Sidrane, Phoenixville, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/691,822

(22) Filed: Nov. 22, 2019

(65) Prior Publication Data

US 2020/0085975 A1 Mar. 19, 2020

Related U.S. Application Data

(63) Continuation of application No. 16/093,798, filed as application No. PCT/US2017/027396 on Apr. 13, 2017.

(60) Provisional application No. 62/323,336, filed on Apr. 15, 2016, provisional application No. 62/331,807, filed on May 4, 2016, provisional application No. 62/428,866, filed on Dec. 1, 2016.

(51) Int. Cl.
| | |
|---|---|
| *A61K 48/00* | (2006.01) |
| *C12N 15/86* | (2006.01) |
| *A61K 9/00* | (2006.01) |
| *A61P 7/04* | (2006.01) |
| *A61K 38/37* | (2006.01) |

(52) U.S. Cl.
CPC ........ *A61K 48/0058* (2013.01); *A61K 9/0019* (2013.01); *A61K 38/37* (2013.01); *A61P 7/04* (2018.01); *C12N 15/86* (2013.01)

(58) Field of Classification Search
CPC ..... A61K 48/0058; A61K 38/37; C12N 15/86
See application file for complete search history.

(56) References Cited

U.S. PATENT DOCUMENTS

| | | | |
|---|---|---|---|
| 5,439,824 A | 8/1995 | Brantly et al. | |
| 5,661,008 A | 8/1997 | Almstedt et al. | |
| 5,789,203 A | 8/1998 | Chapman et al. | |
| 6,200,560 B1 | 3/2001 | Couto et al. | |
| 6,228,620 B1 | 5/2001 | Chapman et al. | |
| 6,268,212 B1 | 7/2001 | Simonet | |
| 6,271,025 B1 | 8/2001 | Negrier et al. | |
| 6,610,906 B1 | 8/2003 | Kurachi et al. | |
| 6,642,028 B2 | 11/2003 | Ill et al. | |
| 6,783,961 B1 | 8/2004 | Edwards et al. | |
| 6,797,505 B2 | 9/2004 | Snyder et al. | |
| 6,812,339 B1 | 11/2004 | Venter et al. | |
| 6,818,439 B1 | 11/2004 | Jolly et al. | |
| 7,282,199 B2 | 10/2007 | Gao et al. | |
| 7,312,324 B2 | 12/2007 | Souza et al. | |
| 7,341,871 B2 | 3/2008 | Kurachi et al. | |
| 7,351,577 B2 | 4/2008 | Couto et al. | |
| 7,351,813 B2 | 4/2008 | Miao et al. | |
| 7,572,619 B2 | 8/2009 | Hauser et al. | |
| 7,635,763 B2 | 12/2009 | Lollar | |
| 7,847,088 B2 | 12/2010 | Bezerra | |
| 7,855,274 B2 | 12/2010 | Fay et al. | |
| 7,943,374 B2 | 5/2011 | Hildinger | |
| 8,008,468 B2 | 8/2011 | Roelvink | |
| 8,021,875 B2 | 9/2011 | Wooddell et al. | |
| 8,030,065 B2 | 10/2011 | Gray | |
| 8,129,510 B2 | 3/2012 | Kay et al. | |
| 8,198,421 B2 | 6/2012 | Samulski et al. | |
| 8,309,698 B2 | 11/2012 | Koh et al. | |
| 9,393,323 B2 | 7/2016 | Nathwani et al. | |
| 9,737,618 B2 | 8/2017 | Wilson et al. | |
| 2002/0131956 A1 | 9/2002 | Walsh et al. | |
| 2002/0165177 A1 | 11/2002 | Negrier et al. | |
| 2003/0099618 A1 | 5/2003 | Couto et al. | |
| 2003/0224508 A1 | 12/2003 | Ill et al. | |
| 2006/0136184 A1 | 6/2006 | Gustafsson et al. | |
| 2007/0243168 A1* | 10/2007 | Kay .................. | A61K 48/0058 424/93.2 |
| 2007/0253936 A1 | 11/2007 | Kay et al. | |
| 2008/0312143 A1 | 12/2008 | Hauser et al. | |
| 2010/0120664 A1 | 5/2010 | Schulte et al. | |
| 2010/0183556 A1 | 7/2010 | Choi et al. | |
| 2011/0124565 A1 | 5/2011 | Hauser et al. | |
| 2011/0184049 A1 | 7/2011 | Chuah et al. | |

(Continued)

FOREIGN PATENT DOCUMENTS

| | | |
|---|---|---|
| WO | WO 1999/029848 | 6/1999 |
| WO | WO 2001/098482 | 12/2001 |

(Continued)

OTHER PUBLICATIONS

Costa et al Mol. Cell. Biol. 6 (12), 4697-4708, (Year: 1986).*
Maeda et al Mol. Biol. Med. 3 (4), 329-338 (Year: 1986).*
Bell et al. Analysis of tumors arising in male B6C3F1 mice with and without AAV vector delivery to liver. Mol Ther. Jul. 2006;14(1):34-44. Epub May 6, 2006.
Biancone et al. Redirection of tumor metastasis by expression of E-selectin in vivo. J Exp Med. Feb. 1, 1996;183(2):581-7.
Breous et al. Hepatic regulatory T cells and Kupffer cells are crucial mediators of systemic T cell tolerance to antigens targeting murine liver. Hepatology. Aug. 2009;50(2):612-21.

(Continued)

*Primary Examiner* — Anoop K Singh
(74) *Attorney, Agent, or Firm* — Howson & Howson LLP; Colleen Schaller

(57) ABSTRACT

Compositions and regimens useful in treating hemophilia A are provided. The compositions include recombinant adeno-associated virus (rAAV) with a transthyretin enhancer and promoter driving expression of a human Factor VIII.

19 Claims, 29 Drawing Sheets

Specification includes a Sequence Listing.

(56) References Cited

U.S. PATENT DOCUMENTS

| | | | | |
|---|---|---|---|---|
| 2012/0058102 | A1* | 3/2012 | Wilson | C12Y 301/21004 |
| | | | | 424/94.6 |
| 2012/0093775 | A1 | 4/2012 | Alonso et al. | |
| 2013/0004462 | A1 | 1/2013 | Samulski et al. | |
| 2013/0030042 | A1 | 1/2013 | Couto et al. | |
| 2013/0045186 | A1 | 2/2013 | Gao et al. | |
| 2013/0158104 | A1 | 6/2013 | Tubert et al. | |
| 2014/0032186 | A1 | 1/2014 | Gustafsson et al. | |
| 2015/0283267 | A1* | 10/2015 | Vandendriessche | A61K 38/37 |
| | | | | 514/44 R |
| 2015/0315612 | A1 | 11/2015 | Wilson et al. | |
| 2016/0229904 | A1* | 8/2016 | Xiao | C07K 14/755 |
| 2017/0233455 | A1* | 8/2017 | Falkner | A61K 48/0008 |
| | | | | 424/93.2 |
| 2019/0022249 | A1 | 1/2019 | Wilson et al. | |

FOREIGN PATENT DOCUMENTS

| | | | |
|---|---|---|---|
| WO | WO 2002/029103 | 4/2002 | |
| WO | WO 2002/071843 | 9/2002 | |
| WO | WO 2003/052051 | 11/2002 | |
| WO | WO 2006/102072 | 9/2006 | |
| WO | WO 2007/078599 | 7/2007 | |
| WO | WO 2008/073303 | 6/2008 | |
| WO | WO 2008/118258 | 10/2008 | |
| WO | WO 2009/122401 | 10/2009 | |
| WO | WO 2009/130208 | 10/2009 | |
| WO | WO 2009/158513 | 12/2009 | |
| WO | WO 2010/024483 | 3/2010 | |
| WO | WO 2010/109053 | 9/2010 | |
| WO | WO 2011/005968 | 1/2011 | |
| WO | WO 2011/109380 | 9/2011 | |
| WO | WO 2011/126808 | 10/2011 | |
| WO | WO 2011/154520 | 12/2011 | |
| WO | WO 2014/064277 | 5/2014 | |
| WO | WO-2014064277 A1 * | 5/2014 | A61K 48/0058 |
| WO | WO 2015/012924 | 1/2015 | |
| WO | WO 2017/100704 | 6/2017 | |

OTHER PUBLICATIONS

Breous et al. Inflammation promotes the loss of adeno-associated virus-mediated transgene expression in mouse liver. Gastroenterology. Jul. 2011;141(1):348-57, 357.e1-3. Epub Apr. 12, 2011.
Bunting et al. Gene Therapy with BMN 270 Results in Therapeutic Levels of FVIII in Mice and Primates and Normalization of Bleeding in Hemophilic Mice. Mol Ther. Feb. 7, 2018;26(2):496-509. Epub Dec. 14, 2017.
Calcedo et al. Assessment of Humoral, Innate, and T-Cell Immune Responses to Adeno-Associated Virus Vectors. Hum Gene Ther Methods. Apr. 2018;29(2):86-95.
Calcedo et al. Worldwide epidemiology of neutralizing antibodies to adeno-associated viruses. J Infect Dis. Feb. 1, 2009;199(3):381-90.
Calvez et al. Recombinant factor VIII products and inhibitor development in previously untreated boys with severe hemophilia A. Nov. 27, 2014;124(23):3398-408. Epub Sep. 24, 2014.
Cao et al. Induction and role of regulatory CD4+CD25+ T cells in tolerance to the transgene product following hepatic in vivo gene transfer. Blood. Aug. 15, 2007;110(4):1132-40. Epub Apr. 16, 2007.
Chao et al. Expression of human factor VIII by splicing between dimerized AAV vectors. Mol Ther. Jun. 2002;5(6):716-22.
Chuah et al. Liver-specific transcriptional modules identified by genome-wide in silico analysis enable efficient gene therapy in mice and nonhuman primates. Mol Ther. Sep. 2014;22(9):1605-13. Epub Jun. 23, 2014.
Ciliberto et al. Cell-specific expression of a transfected human α1-antitrypsin gene. Cell. Jun. 1985;41(2):531-40.
Dang et al. Structure of the hepatic control region of the human apolipoprotein E/C-I gene locus. J Biol Chem. Sep. 22, 1995;270(38):22577-85.

Dimatteo et al. Hyperactive piggyBac transposons for sustained and robust liver-targeted gene therapy. Mol Ther. Sep. 2014;22(9):1614-24. Epub Jul. 18, 2014.
Dimichele. Inhibitor development in haemophilia B: an orphan disease in need of attention. Br J Haematol. Aug. 2007;138(3):305-15.
Dobrzynski et al. Induction of antigen-specific CD4+ T-cell anergy and deletion by in vivo viral gene transfer. Blood. Aug. 15, 2004;104(4):969-77. Epub Apr. 22, 2004.
Dobrzynski et al. Prevention of cytotoxic T lymphocyte responses to factor IX-expressing hepatocytes by gene transfer-induced regulatory T cells. Proc Natl Acad Sci U S A. Mar. 21, 2006;103(12):4592-7. Epub Mar. 10, 2006.
Eckhardt et al. Factor VIII gene (F8) mutation and risk of inhibitor development in nonsevere hemophilia A. Blood. Sep. 12, 2013;122(11):1954-62. Epub Aug. 7, 2013.
Freitas et al. Sequencing of 42kb of the APO E-C2 gene cluster reveals a new gene: PEREC1. DNA Seq. 1998;9(2):89-100.
Gao et al. Adeno-associated viruses undergo substantial evolution in primates during natural infections. Proc Natl Acad Sci U S A. May 13, 2003;100(10):6081-6. Epub Apr. 25, 2003.
Gao et al.Biology of AAV serotype vectors in liver-directed gene transfer to nonhuman primates. Mol Ther. Jan. 2006;13(1):77-87. Epub Oct. 10, 2005.
Garcia et al. Transgenic mice expressing high levels of soluble TNF-R1 fusion protein are protected from lethal septic shock and cerebral malaria, and are highly sensitive to Listeria monocytogenes and Leishmania major infections. Eur J Immunol. Aug. 1995;25(8):2401-7.
GenBank: AAO88201, capsid protein [Non-human primate Adeno-associated virus], May 14, 2003.
GenBank: AAS99285, capsid protein VP1 [Adeno-associated virus], Jun. 24, 2004.
George et al. Hemophilia B Gene Therapy with a High-Specific-Activity Factor IX Variant. N Engl J Med. Dec. 7, 2017;377(23):2215-2227.
Giles et al. A detailed comparison of the performance of the standard versus the Nijmegen modification of the Bethesda assay in detecting factor VIII:C inhibitors in the haemophilia A population of Canada. Association of Hemophilia Centre Directors of Canada. Factor VIII/IX Subcommittee of Scientific and Standardization Committee of International Society on Thrombosis and Haemostasis. Thromb Haemost. Apr. 1998;79(4):872-5.
Gouw et al. Factor VIII products and inhibitor development in severe hemophilia A. N Engl J Med. Jan. 17, 2013;368(3):231-9.
Greig et al. Characterization of Adeno-Associated Viral Vector-Mediated Human Factor VIII Gene Therapy in Hemophilia A Mice. Hum Gene Ther. May 2017;28(5):392-402. Epub Jan. 5, 2017.
Greig et al. Intramuscular injection of AAV8 in mice and macaques is associated with substantial hepatic targeting and transgene expression. PLoS One. Nov. 13, 2014;9(11):e112268.
Greig et al., Optimized AAV-Mediated Human Factor VIII Gene Therapy in Hemophilia A Mice and Cynomolgus Macaques, Abstract presented at ASGCT 19th Annual Meeting, Washington, D.C., May 4-7, 2016.
Grieger and Samulski. Packaging capacity of adeno-associated virus serotypes: impact of larger genomes on infectivity and postentry steps. J Virol. Aug. 2005;79(15):9933-44.
Grimm et al. Titration of AAV-2 particles via a novel capsid ELISA: packaging of genomes can limit production of recombinant AAV-2. Gene Ther. Jul. 1999;6(7):1322-30.
Hasbrouck and High. AAV-mediated gene transfer for the treatment of hemophilia B: problems and prospects. Gene Ther. Jun. 2008;15(11):870-5. Epub Apr. 24, 2008.
Hoffman et al. Muscle as a target for supplementary factor IX gene transfer. Hum Gene Ther. Jul. 2007;18(7):603-13.
Ill et al. Optimization of the human factor VIII complementary DNA expression plasmid for gene therapy of hemophilia A. Blood Coagul Fibrinolysis. Dec. 1997;8 Suppl 2:S23-30.
Jiang et al. Multiyear therapeutic benefit of AAV serotypes 2, 6, and 8 delivering factor VIII to hemophilia A mice and dogs. Blood. Jul. 1, 2006;108(1):107-15. Epub Mar. 7, 2006.

(56) References Cited

OTHER PUBLICATIONS

Kay Ma et al., Evidence for gene transfer and expression of factor IX in haemophilia B patients treated with an AAV vector, Nature Genetics, 24(3):257-61, Mar. 2000.

Lind et al. Novel forms of B-domain-deleted recombinant factor VIII molecules. Construction and biochemical characterization. Eur J Biochem. Aug. 15, 1995;232(1):19-27.

Lock et al. Rapid, simple, and versatile manufacturing of recombinant adeno-associated viral vectors at scale. Hum Gene Ther. Oct. 2010;21(10):1259-71.

Long et al. Complete sequence of the cDNA for human alpha 1-antitrypsin and the gene for the S variant. Biochemistry. Oct. 9, 1984;23(21):4828-37.

Lytle AM et al., Effects of FVIII immunity on hepatocyte and hematopoietic stem cell-directed gene therapy of murine hemophilia A, Methods & Clinical Development, vol. 3:15056, Feb. 10, 2016.

Martino et al. Tolerance induction to cytoplasmic betagalactosidase by hepatic AAV gene transfer: implications for antigen presentation and immunotoxicity. PLoS One. Aug. 4, 2009;4(8):e6376.

McIntosh et al. Therapeutic levels of FVIII following a single peripheral vein administration of rAAV vector encoding a novel human factor VIII variant. Blood. Apr. 25, 2013;121(17):3335-44.

Mingozzi et al. Induction of immune tolerance to coagulation factor IX antigen by in vivo hepatic gene transfer. J Clin Invest 2003;111:1347-1356.

Miyatake et al. Transcriptional Targeting of Herpes Simplex Virus for Cell-Specific Replication, J. Virol., Jul. 1997; 71(7):5124-32.

Mount et al. Sustained phenotypic correction of hemophilia B dogs with a factor IX null mutation by liver-directed gene therapy. Blood 2002;99:2670-2676.

Nair et al. Computationally designed liver-specific transcriptional modules and hyperactive factor IX improve hepatic gene therapy. Blood. May 15, 2014;123(20):3195-9. Epub Mar. 17, 2014.

Nathwani et al. Adenovirus-associated virus vector mediated gene transfer in hemophilia B. N Engl J Med. Dec. 22, 2011;365(25):2357-65. Epub Dec. 10, 2011.

Nathwani et al. Long-term safety and efficacy of factor IX gene therapy in hemophilia B. N Engl J Med. Nov. 20, 2014;371(21):1994-2004.

Nathwani et al. Self-complementary adeno-associated virus vectors containing a novel liver-specific human factor IX expression cassette enable highly efficient transduction of murine and nonhuman primate liver. Blood. Apr. 1, 2006;107(7):2653-61. Epub Dec. 1, 2005.

Nathwani et al. Sustained high-level expression of human factor IX (hFIX) after liver-targeted delivery of recombinant adeno-associated virus encoding the hFIX gene in rhesus macaques. Blood 2002;100:1662-1669.

Nguyen et al. Novel factor VIII variants with a modified furin cleavage site improve the efficacy of gene therapy for hemophilia A. Jan. 2017;15(1):110-121. Epub Nov. 25, 2016.

Peyvandi et al. A Randomized Trial of Factor VIII and Neutralizing Antibodies in Hemophilia A. N Engl J Med. May 26, 2016;374(21):2054-64.

Powell et al. Phase 1 trial of FVIII gene transfer for severe hemophilia A using a retroviral construct administered by peripheral intravenous infusion. Blood. Sep. 15, 2003;102(6):2038-45. Epub May 22, 2003.

Radcliffe et al. Analysis of factor VIII mediated suppression of lentiviral vector titres. Gene Ther. Feb. 2008;15(4):289-97. Epub Nov. 29, 2007.

Rangarajan et al. AAV5-Factor VIII Gene Transfer in Severe Hemophilia A. N Engl J Med. Dec. 28, 2017;377(26):2519-2530.

Rouet et al. A potent enhancer made of clustered liver-specific elements in the transcription control sequences of human alpha 1-microglobulin/bikunin gene. J Biol Chem. Oct. 15, 1992;267(29):20765-73.

Sandberg et al. Structural and functional characteristics of the B-domain-deleted recombinant factor VIII protein, r-VIII SQ. Thromb Haemost. Jan. 2001;85(1):93-100.

Sandig et al. HBV-derived promoters direct liver-specific expression of an adenovirally transduced LDL receptor gene. Gene Ther., Nov. 1996; 3(11):1002-9.

Sarkar et al, Total Correction of Hemophilia A Mice with Canine FVIII Using an AAV 8 Serotype, Blood First Edition Paper, 103(4), pp. 1253-60, published online Oct. 9, 2003.

Sarkar et al. A single adeno-associated virus (AAV)-murine factor VIII vector partially corrects the hemophilia A phenotype. Journal of Thrombosis and Haemostasis. J Thromb Haemost. Feb. 2003;1(2):220-6.

Siner et al. Circumventing furin enhances factor VIII biological activity and ameliorates bleeding phenotypes in hemophilia models. JCI Insight. Oct. 6, 2016;1(16):e89371.

Skarnes et al. A conditional knockout resource for the genome-wide study of mouse gene function. Nature. Jun. 15, 2011;474(7351):337-42.

Sommer et al. Quantification of adeno-associated virus particles and empty capsids by optical density measurement. Mol Ther. Jan. 2003;7(1):122-8.

Sullivan et al., SPK-8011: Preliminary Results from a Phase 1/2 Trial of Investigational Gene Therapy for Hemophilia Confirm Transgene Derived Increases in FVIII Activity That Are Persistent and Stable beyond Eight Months. Molecular Therapy, 2018;26(suppl):163.

Thomson et al. A comprehensive comparison of multiple sequence alignments. Nucleic Acids Res. Jul. 1, 1999;27(13):2682-90.

Toole et al. A large region (approximately equal to 95 kDa) of human factor VIII is dispensable for in vitro procoagulant activity. Proc Natl Acad Sci U S A. Aug. 1986;83(16):5939-42.

Wang et al. Identification of an adeno-associated virus binding epitope for AVB sepharose affinity resin. Mol Ther Methods Clin Dev. Nov. 4, 2015;2:15040.

Wang et al. Muscle-directed gene therapy for hemophilia B with more efficient and less immunogenic AAV vectors. J Thromb Haemost. Oct. 2011;9(10):2009-19.

Wang et al. Sustained correction of OTC deficiency in spf( ash) mice using optimized self-complementary AAV2/8 vectors. Gene Ther. Apr. 2012;19(4):404-10. Epub Aug. 18, 2011.

Wang et al. Sustained expression of therapeutic level of factor IX in hemophilia B dogs by AAV-mediated gene therapy in liver. Mol Ther. Feb. 2000;1(2):154-8.

Wang et al. Systematic evaluation of AAV vectors for liver directed gene transfer in murine models. Mol Ther. Jan. 2010;18(1):118-25. Epub Oct. 27, 2009.

Wang et al. The pleiotropic effects of natural AAV infections on liver-directed gene transfer in macaques. Mol Ther. Jan. 2010;18(1):126-34. Epub Nov. 3, 2009.

Ward et al. Codon optimization of human factor VIII cDNAs leads to high-level expression. Blood 2011;117:798-807. Blood. Jan. 20, 2011;117(3):798-807. Epub Nov. 1, 2010.

Wobus et al. Monoclonal antibodies against the adeno-associated virus type 2 (AAV-2) capsid: epitope mapping and identification of capsid domains involved in AAV-2-cell interaction and neutralization of AAV-2 infection. J Virol. Oct. 2000 ;74(19):9281-93.

Wu et al., Optimization of self-complementary AAV vectors for liver-directed expression results in sustained correction of hemophilia B at low vector dose, Mol Ther. Feb. 2008;16(2):280-9. Epub Dec. 4, 2007.

International Search Report and Written Opinion in International Patent Application No. PCT/US2017/027396, dated Sep. 12, 2017.

Pipe et al., 2020, 23rd Annual Meeting of the American Society of Gene and Cell Therapy, Abstract No. 941: "First-in-human gene therapy study of AAVhu37 capsid vector technology in severe hemophilia A: safety and FVIII activity results"; Published Apr. 28, 2020; Scheduled for Presentation on May 14, 2020.

Non-Final Office Action dated Feb. 6, 2020 in U.S. Appl. No. 16/093,798.

Response to Office Action dated Feb. 6, 2020 filed in U.S. Appl. No. 16/093,798.

(56) References Cited

OTHER PUBLICATIONS

Office Action dated Oct. 15, 2019 issued in corresponding European Patent Application No. 17734159.1.
Response to Office Action dated Oct. 15, 2019 filed in corresponding European Patent Application No. 17734159.1.

* cited by examiner

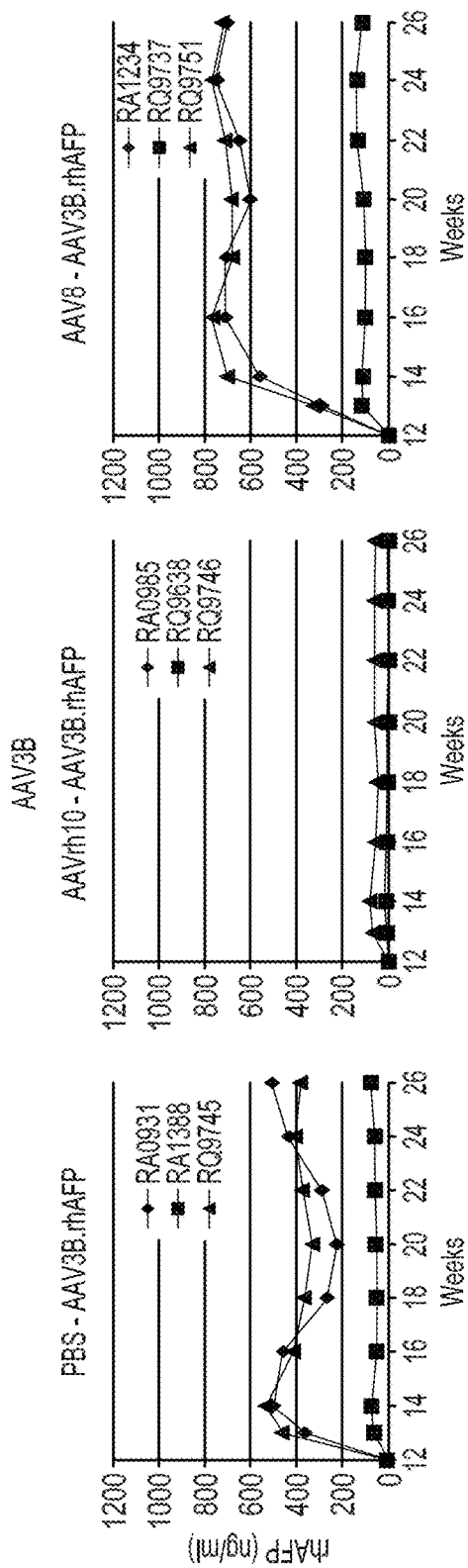
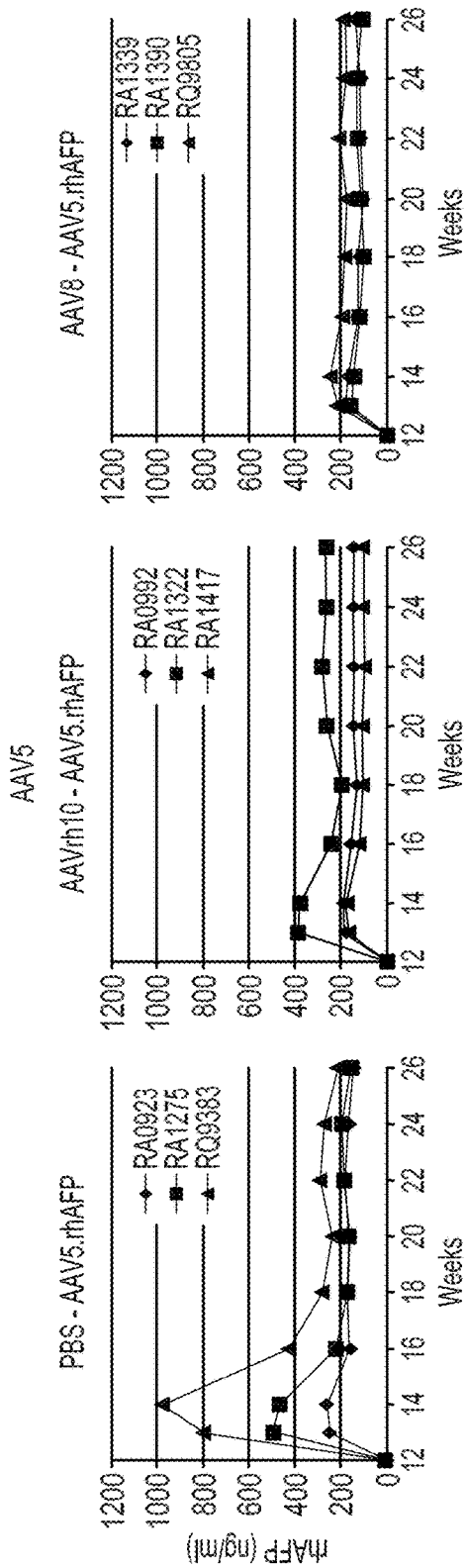
Figure 17A
Figure 17B

Percent Identify Matrix - created by Clustal2.1

1: hFVIIIco    100.00  77.24 (SEQ ID NO: 2)
   2: hFVIII       77.24  100.00 (SEQ ID NO: 1)

```
hfVIIIco    atgcagatcgagctgagcacctgcttcttcctgtgcctgctgcggttctgcttctccgcc    60
hfVIII      atgcaaatagagctctccacctgcttctttctgtgccttttgcgattctgctttagtgcc    60
            ***  ***  ******** ***   ****    * hfVIIIco    accggcggtactacctgggagccgtggagctgagctgggattacatgcagagcgatctg    120
hfVIII      accagaagatactacctgggtgcagtggaactgtcatgggactatatgcaaagtgatctc    120
            *** *  * ********   ***  *    *  ***  *** hfVIIIco    ggagagctgccagtggatgcccggttcccaccacgggtgccaaagagcttcccattcaac    180
hfVIII      ggtgagctgcctgtggacgcaagattcctcctagagtgccaaaatctttccattcaac    180
             ***** *        * ******** *   ******* hfVIIIco    accagcgtggtgtacaagaagaccctgttcgtggagttcaccgatcacctgttcaacatc    240
hfVIII      acctcagtcgtgtacaaaaagactctgtttgtagaattcacggatcaccttttcaacatc    240
            *    **  * *   *  *** * ***** ******* hfVIIIco    gccaagccacggccaccctggatgggactgctgggaccaacaatccaggccgaggtgtac    300
hfVIII      gctaagccaaggccaccctggatgggtatgctaggtcctaccatccaggctgaggtttat    300
             ** *********** *      ***** * hfVIIIco    gataccgtggtgatcaccctgaagaacatggcctctcatcctgtgtccctgcacgccgtg    360
hfVIII      gatacagtggtcattacacttaagaacatggcttccatcctgtcagtcttcatgctgtt    360
            *** *     *********** *  ****** hfVIIIco    ggagtgagctactggaaggccagcgagggagccgagtacgatgatcagaccagccagcgg    420
hfVIII      ggtgtatcctactggaaagcttctgagggagctgaatatgatgatcagaccagtcaaagg    420
               *****   ****    *********   ** hfVIIIco    gagaaggaggatgataaggtgttcccaggaggaagccacacctacgtgtggcaggtgctg    480
hfVIII      gagaaagaagatgataaagtcttcctggtggaagccatacatatgtctggcaggtcctg    480
            ****  ******  **   ******   *    *****  * hfVIIIco    aaggagaacggaccaatggccagcgatccactgtgcctgacctacagctacctgagccac    540
hfVIII      aaagagaatggtccaatggcctctgaccactgtgccttacctactcatatcttttctcat    540
             *  ******    * ***** * ****  * ** *  * * * * hfVIIIco    gtggatctggtgaaggatctgaacagcggactgatcggagccctgctggtgtgcgcggag    600
hfVIII      gtggacctggtaaaagacttgaattcaggcctcattggagccctactagtatgtagagaa    600
            *** *     *  ** *  * *****  *  *  ** hfVIIIco    ggaagcctggccaaggagaagacccagaccctgcacaagttcatcctgctgttcgccgtg    660
hfVIII      gggagtctggccaaggaaaagacacagacctttgcacaaatttatactactttttgctgta    660
              *********  * *     * *   * *      ** hfVIIIco    ttcgatgagggaaagagctggcacagcgagaccaagaacagcctgatgcaggatcgggat    720
hfVIII      tttgatgaagggaaaagttggcactcagaaacaaagaactccttgatgcaggataggat    720
             *   *   ***   *   *  * ********* *** hfVIIIco    gccgcagcgccgggcctggccaagatgcacaccgtgaacggatacgtgaaccggagc    780
hfVIII      gctgcatctgtcgggcctggcctaaaatgcacacagtcaatggttatgtcaacaggtct    780
            ** ***   ** ********** **  ********* ** ** ** ** ** ***  **
```

Figure 25

```
hfVIIIco   ctgccaggactgatcggatgccaccggaagagcgtgtactggcacgtgatcggaatggga   840
hfVIII     ctgccaggtctgattggatgccaccggaaatcagtgtattggcatgtgattggaatgggc   840
           ******   *******      * * * ******* hfVIIIco   accacccagaggtgcactctatcttcctggagggacacacctttctggtgcggaaccac   900
hfVIII     accactcctgaagtgcactcaatattcctcgaaggtcacacatttcttgtgaggaaccat   900
           ***   ****  ***  *** * * * ***** hfVIIIco   cggcaggccagcctggagatcagcccaatcaccttcctgaccgcccagaccctgctgatg   960
hfVIII     cgccaggcgycttggaaatctcgccaataactttccttactgtcaaacactcttgatg    960
            ***  * ** *   ***  *      * *** hfVIIIco   gatctgggacagttcctgctgttctgccatatcagcagccaccagcacgatggaatggag   1020
hfVIII     gaccttggacagtttctaatgttttgtcatatctcttccaccaacatgatggcatggaa    1020
             ******  ***  ****       **  *** *** hfVIIIco   gcctacgtgagggtggatagctgccagagaagccacagctgcggctgaagaacaacgag   1080
hfVIII     gcttatgtcaaagtagacagctgtccagagaaccccaactacgaatgaaaaataatgaa   1080
                 **  ***     *** hfVIIIco   gaggccgaggattacgatgatgatctgaccgatagcgagatggatgtggtgcggttcgat   1140
hfVIII     gaagcggaagactatgatgatgatcttactgattctgaaatggatgtggtcaggtttgat   1140
                ********     ***** *  * hfVIIIco   gatgataacagcccaagcttcatccagatccggagcgtggccaagaagcacccaaagacc   1200
hfVIII     gatgacaactctcctcctttatccaaattcgctcagttgccaagaagcatcctaaaact   1200
           *** *       **         ******* hfVIIIco   tgggtgcactacatcgccgccgaggaggaggattgggattacgcccactggtgctggcc   1260
hfVIII     tgggtacattacattgctgctgaagaggaggactgggactatgctccttagtcctcgcc   1260
           ***   ***    ****** *      *  * hfVIIIco   cctgatgatcggagctacaagagccagtacctgaacaacggaccacagcggatcggacgg   1320
hfVIII     cccgatgacagaagttataaaagtcaatatttgaacaatggccctcagcggattggtagg   1320
            *   * *          ****  ******  ** hfVIIIco   aagtaccccaaagtgcggttcatggcctacaccgatgagaccttcaagacccggggaggcc   1380
hfVIII     aagtacaaaaaagtccgatttatggcatacacagatgaaacctttaagactcgtgaagct   1380
           **** * *    * * * * *   ** * hfVIIIco   atccagcacgagagcggaatcctgggaccactgctgtacggagaggtgggagatacctg   1440
hfVIII     attcagcatgaatcaggaatcttggacctttactttatgggaagttggagacacactg   1440
            *     ****  ** * *     ***  *** hfVIIIco   ctgatcatcttcaagaaccaggccagccggccatacaacatctacccacacggaatcacc   1500
hfVIII     ttgattatatttaagaatcaagcaagcagaccatataacatctaccctcacggaatcact   1500
           * **   *   *  ** ***** ********* hfVIIIco   gatgtgcggccactgtacagccggcggctgccaaagggagtgaagcacctgaaggatttc   1560
hfVIII     gatgtccgtcctttgtattcaaggagattaccaaaaggtgtaaaacatttgaaggattt    1560
           ***            *****    * ********** hfVIIIco   ccaatcctgccaggagagatcttcaagtacaagtggacagtgacagtggaggatggacca   1620
hfVIII     ccaattctgccaggagaaatattcaaatataaatggacagtgactgtagaagatgggcca   1620
           *** *******  ***   *****    *** hfVIIIco   accaagtctgatccaagatgcctgaccagatactacagcagctttgtgaacatggagaga   1680
hfVIII     actaaatcagatcctcggtgcctgaccogctattactctagtttcgttaatatggagaga   1680
           ** ** ** *****  * ********   ** ** ** ** ** ** ** **********
```

Figure 25 (cont'd)

```
hfVIIIco    gacctggcctctggactgattggaccactgctgatctgctaccggagtctgtggatcag    1740
hfVIII      gatctagcttcaggactcattggccctctcctcatctgctacaaagaatctgtagctcaa    1740
                *** *    *********  *** *** hfVIIIco    agaggaaaccagatcatgtctgataagagaaatgtgatcctgttctctgtgtttgatgag    1800
hfVIII      agaggaaaccagataatgtcagacaagaggaatgtcatcctgttttctgtatttgatgag    1800
            ***********    * * **** * ****** hfVIIIco    aacagaagctggtacctgacagagaacatccagagattcctgccaaacccagccggagtg    1860
hfVIII      aaccgaagctggtacctcacagagaatatacaacgctttctccccaatccagctggagtg    1860
            * ************* ****  **  *     *** **** hfVIIIco    cagctggaggatccagagttccaggccagcaacatcatgcacagcatcaacggatacgtg    1920
hfVIII      cagcttgaggatccagagttccaagcctccaacatcatgcacagcatcaatggctatgtt    1920
            *** ************** * ******************* hfVIIIco    ttcgatagcctgcagctgagcgtgtgcctgcaggaggtggcctattggtatatcctgagc    1980
hfVIII      tttgatagtttgcagttgtcagtttgtttgcatgaggtggcatactggtacattctaagc    1980
             *  *         *****   ***   * hfVIIIco    atcggagcccagaccgatttcctgagcgtgttcttcagcggatacaccttcaagcacaag    2040
hfVIII      attggagcacagactgacttcctttctgtcttcttctctggatataccttcaaacacaaa    2040
             * *  ***     ****    * **** *** hfVIIIco    atggtgtacgaggataccctgacctgttcccattctccggagagaccgtgttcatgagc    2100
hfVIII      atggtctatgaagacacactcacctattcccattctcaggagaaactgtcttcatgtcg    2100
            ***        ********* *   **** * hfVIIIco    atggagaacccaggactgtggatcctgggatgccacaactctgatttcagaaacagagga    2160
hfVIII      atggaaaaccaggtctatggattctggggtgccacaactcagactttcggaacagaggc    2160
            *** **   *   *********   *** * ******** hfVIIIco    atgactgccctgctgaaagtgtccagctgtgataagaacactggagattactatgaggat    2220
hfVIII      atgaccgccttactgaaggtttctcgttgtgacaagaacactggtgattcttacgaggac    2220
            *** **  * ***    * ******* *   *** hfVIIIco    agctatgaggatatctctgcctacctgctgagcaagaacaatgccattgagccaagaagc    2280
hfVIII      agttatgaagatatttcagcatacttgctgagtaaaaacaatgccattgaaccaagaagc    2280
             * *   * *****  *************** ******* hfVIIIco    ttcagccagaacccaccagtgctgaagagacaccagagagagatcaccagaaccaccctg    2340
hfVIII      ttctcccagaatccaccagtcttgaaacgccatcaacgggaaataactcgtactactctt    2340
            * ** *******  * **** *   ** *   * hfVIIIco    cagtctgatcaggaggagattgattatgatgataccatctctgtggagatgaagaaggag    2400
hfVIII      cagtcagatcaagaggaaattgactatgatgataccatatcagttgaaatgaagaaggaa    2400
            *** * * * **********    *********** hfVIIIco    gattttgatatctatgatgaggatgagaaccagagcccaagaagcttccagaagaagacc    2460
hfVIII      gattttgacatttatgatgaggatgaaaatcagagccccgcagctttcaaaagaaaaca    2460
            ******  ************  ******** *    ***  ** hfVIIIco    agacactacttcatcgctgcagtggagagactgtgggattatggaatgagcagcagccca    2520
hfVIII      cgacactattttattgctgcagtggagagggctctggattatgggatgagtagctcccca    2520
            *****   * ***************   * ********* * * **** hfVIIIco    cacgtgctgagaaacagagcccagagcggatctgtgccacagttcaagaaggtggtgttc    2580
hfVIII      catgttctaagaaacagggctcagagtggcagtgtccctcagttcaagaaagttgttttc    2580
            ** ** **  ******* **  ***** **    ** **  ********* **  ****
```

Figure 25 (cont'd)

```
hfVIIIco    caggagttcaccgatggaagcttcacccagccactgtaccggggagagctgaacgagcac    2640
hfVIII      caggaatttactgatggctcctttactcagccctataccgtggagaactaaatgaacat    2640
            ***    *   *  ***  * *** * hfVIIIco    ctgggactgctggaccatacatccggggccgaggtggaggataacatcatggtgaccttc    2700
hfVIII      ttgggactcctgggggccatatataagagcagaagttgaagataatatcatggtaactttc    2700
            ***** *  *   *     ** *  **  ****   *** hfVIIIco    cggaaccaggccagccggccatacagcttctacagcagcctgatcagctacgaggaggat    2760
hfVIII      agaaatcaggcctctcgtccctattccttctattctagccttatttcttatgaggaagat    2760
             *  **        **** *     *** * hfVIIIco    cagcggcagggagccgagccacggaagaacttcgtgaagccaaacgagaccaagacctac    2820
hfVIII      cagaggcaaggagcagaacctagaaaaaactttgtcaagcctaatgaaaccaaaacttac    2820
            *  *  **   *  * ***  ***   *  *** hfVIIIco    ttctggaaggtgcagcaccacatggcccccaaccaaggatgagttcgattgcaaggcctgg    2880
hfVIII      ttttggaaagtgcaacatcatatggcacccactaaagatgagttttgactgcaaagcctgg    2880
             * *     * *   *  ***  ****** hfVIIIco    gcctacttcagcgatgtggatctggagaaggatgtgcacagcggactgatcggaccactg    2940
hfVIII      gcttatttctctgatgttgacctggaaaagatgtgcactcaggcctgattggaccccctt    2940
               *  *   ***   ***    * *  * * hfVIIIco    ctggtgtgccacaccaacaccctgaacccagcccacggacggcaggtgaccgtgcaggag    3000
hfVIII      ctggtctgcacactaacacactgaacctgctcatgggagacaagtgacagtacaggaa    3000
            ***  *  * ****  *   *  *    *  *** hfVIIIco    ttcgccctgttcttcaccatcttcgatgagaccaagagctggtacttcaccgagaacatg    3060
hfVIII      tttgctctgttttttcaccatctttgatgagaccaaaagctggtacttcactgaaaatatg    3060
              ***  ****** **** * ******    * hfVIIIco    gagcggaactgccgggccccttgcaacatccagatggaggatccaaccttcaaggagaac    3120
hfVIII      gaaagaaactgcagggctccctgcaatatccagatggaagatcccactttaaagagaat    3120
            **  * **** *  ** ****  *      ** hfVIIIco    taccggttccacgccatcaacggatacatcatggatacccctgccaggactggtgatggcc    3180
hfVIII      tatcgttccatgcaatcaatggctacataatggatacactacctggcttagtaatggct    3180
              *** *  * **** *   **    *   *** hfVIIIco    caggatcagcggatccggtggtacctgctgagcatgggaagcaacgagaacatccacagc    3240
hfVIII      caggatcaaaggattcgatggtatctgctcagcatgggcagcaatgaaaacatccattct    3240
            ******   *    *  *** *   ******** hfVIIIco    atccactttcagcggacacgtgttcaccgtgcggaagaaggaggagtacaagatggcccctg    3300
hfVIII      attcatttcagtggacatgtgttcactgtacgaaaaagaggagtataaaaatggcactg    3300
              *** *  *   *    *   ***** hfVIIIco    tacaacctgtacccaggagtgttcgagaccgtggagatgctgccaagcaaggccggaatc    3360
hfVIII      tacaatctctatccaggtgtttttgagacagtggaaatgttaccatccaaagctggaatt    3360
            ***    *   **** * *** ***   *  ***  *** * hfVIIIco    tggcgggtggagtgcctgatcggagagcacctgcacgccggaatgagcacccctgttcctg    3420
hfVIII      tggcgggtggaatgccttattggcgagcatctacatgctgggatgagcacactttttctg    3420
            *********  *   * *****  *    * ***********  *  *** hfVIIIco    gtgtacagcaacaagtgccagaccccactgggaatggccagcggacacatccgggatttc    3480
hfVIII      gtgtacagcaataagtgtcagactcccctgggaatggcttctggacacattagagatttt    3480
            ***********  ***** *****  ** ********   * ******** *  ***** 
```

Figure 25 (cont'd)

```
hfVIIIco   cagatcaccgccagcggacagtacggacagtgggccccaaagctggcccggctgcactac   3540
hfVIII     cagattacagcttcaggacaatatggacagtgggcccaaagctggccagacttcattat   3540
           **            *********************** hfVIIIco   agcggaagcatcaacgcctggagcaccaaggagccattcagctggatcaaagtggatctg   3600
hfVIII     tccggatcaatcaatgcctggagcaccaaggagccctttcttggatcaagtggatctg   3600
             **    * ****************   ****** ******** hfVIIIco   ctggccccaatgatcatccacggaatcaagacccagggagcccggcagaagttcagcagc   3660
hfVIII     ttggcaccaatgattattcacggcatcaagacccagggtgcccgtcagaagttctccagc   3660
            * ****  *** **********  *  **** ** hfVIIIco   ctgtacatcagccagttcatcatcatgtacagcctggatggaaagaagtggcagacctac   3720
hfVIII     ctctacatctctcagtttatcatcatgtatagtcttgatgggaagaagtggcagacttat   3720
            **    * ******   * ********** hfVIIIco   cggggaaacagcaccggaaccctgatggtgttcttcggaaacgtggatagcagcggaatc   3780
hfVIII     cgaggaaattccactggaacctaatggtcttctttggcaatgtggattcatctgggata   3780
            *   * ******* * *** *   *** * hfVIIIco   aagcacaacatcttcaaccccaccaatcatcgcccgatacatccggctgcacccaacccac   3840
hfVIII     aaacacaatatttttaaccctccaattattgctcgatacatccgtttgcacccaactcat   3840
            *   *  ***  **   *******   ********  * hfVIIIco   tacagcatcagaagcacccctgcggatggagctgatgggatgtgatctgaacagctgctcc   3900
hfVIII     tatagcattcgcagcactcttcgcctggagttgatgggctgtgatttaaatagttgcagc   3900
            ***  * *** *      ** *      * hfVIIIco   atgccactgggaatggagagcaaggccatcagcgatgcccagatcaccgccagcagctac   3960
hfVIII     atgccattgggaatggagagtaaagcaatatcagatgcacagattactgcttcatcctac   3960
           **** *********    *   ** *      ** hfVIIIco   ttcaccaacatgttcgccacctggagcccaagcaaggcccggctgcacctgcagggacgg   4020
hfVIII     tttaccaatatgtttgccacctggtctccttcaaaagctcgacttcacctccaagggagg   4020
            * * ****             ***  *** * hfVIIIco   agcaacgcctggcggccacaggtgaataacccaaaggagtggctgcaggtggatttccag   4080
hfVIII     agtaatgcctggagacctcaggtgaataatccaaaagagtggctgcaagtggacttccag   4080
             ****** *    ****  * ****** * **** hfVIIIco   aagaccatgaaggtgaccggagtgaccacccagggagtgaagagcctgctgactagcatg   4140
hfVIII     aagacaatgaaagtcacaggagtaactactcagggagtaaaaatctctgcttaccagcatg   4140
           **** **   ****   ********   *    ** * ****** hfVIIIco   tatgtgaaggagttcctgatcagcagcagccaggatggacaccagtggaccctgttcttc   4200
hfVIII     tatgtgaaggagttcctcatctccagcagtcaagatggccatcagtggactctcttttt   4200
           ***************  ****   ***  ******* hfVIIIco   cagaacggaaaggtgaaggtgttccagggaaaccaggatagcttcacccccagtggtgaac   4260
hfVIII     cagaatggcaaagtaaaggttttttcagggaaatcaagactccttcacacctgtggtgaac   4260
           ***  *  ***     *** *      **   ******** hfVIIIco   agcctggatccaccactgctgacccgatacctgcggatccacccacagagctggtgcac   4320
hfVIII     tctctagacccaccgttactgactcgctaccttcgaattcacccccagagttgggtgcac   4320
                 *****  * **   *  * **   ***** hfVIIIco   cagatcgccctgagaatggaggtgctgggatgcgaggcccaggatctgtactga       4374
hfVIII     cagattgccctgaggatggaggttctgggctgcgaggcacaggacctctac---       4371
           ***** ******** ******** ***** ******** ***** ** **
```

GENE THERAPY FOR TREATING HEMOPHILIA A

CROSS-REFERENCE TO RELATED APPLICATIONS

This application is a continuation of U.S. patent application Ser. No. 16/093,798, filed Oct. 15, 2018, which is a National Stage Entry under 35 U.S.C. 371 of International Patent Application No. PCT/US2017/027396, filed Apr. 13, 2017, which claims the benefit under 35 USC 119(e) of U.S. Provisional Patent Application No. 62/323,336, filed Apr. 15, 2016, U.S. Provisional Patent Application No. 62/331,807, filed May 4, 2016, and U.S. Provisional Patent Application No. 62/428,866, filed Dec. 1, 2016. These applications are incorporated by reference herein.

INCORPORATION-BY-REFERENCE OF MATERIAL SUBMITTED IN ELECTRONIC FORM

Applicant hereby incorporates by reference the Sequence Listing material filed in electronic form herewith. This file is labeled "UPN-16-7798PCT_ST25.txt".

1. INTRODUCTION

The application relates to embodiments useful for a gene therapy for treating hemophilia A.

2. BACKGROUND

Hemophilia A (HA or HemA) is the most common inherited bleeding disorder. According to the US Centers for Disease Control and Prevention, hemophilia A occurs in approximately 1 in 5,000 live births. There are about 20,000 people with hemophilia A in the US. Hemophilia A is four times as common as hemophilia B, and more than half of patients with hemophilia A have the severe form of hemophilia. HA is caused by a deficiency of factor VIII (FVIII) and is well suited for a gene replacement approach, primarily because a modest increase in the level of FVIII (>1% of normal) can ameliorate the severe bleeding phenotype. Adeno-associated viral (AAV) vectors currently show the greatest promise for gene therapy applications because of their excellent safety profile and ability to direct long-term transgene expression from postmitotic tissues such as the liver.

The use of AAV vectors for HA gene therapy, however, poses new challenges because of the distinct molecular and biochemical properties of human FVIII ("hFVIII"). Compared with other proteins of similar size, expression of hFVIII is highly inefficient. Bioengineering of the FVIII molecule has resulted in improvement of the FVIII expression. For instance, the hFVIII B domain, which is not required for co-factor activity, has been deleted (BDD) and replaced by a short 14 amino acid linker (FVIII SQ) resulting in a 17-fold increase in mRNA levels over full-length wild-type FVIII and a 30% increase in secreted protein. See, Ward, Natalie J., et al. "Codon optimization of human factor VIII cDNAs leads to high-level expression." Blood 117.3 (2011): 798-807 and U.S. Pat. No. 9,393,323, also published as WO 2011/005968. Recombinant FVIII-BDD-SQ is in clinical use as a replacement recombinant FVIII product (Refacto, Wyeth Pharma; Xyntha, Pfizer).

Another obstacle to AAV-mediated gene transfer for HA gene therapy is the size of the FVIII coding sequence, which at 7.0 kb, far exceeds the normal packaging capacity of AAV vectors. Packaging of large expression cassettes into AAV vectors has been reported, but this is a highly inconsistent process resulting in low yields of vector particles with reduced infectivity and requiring a high dose that might induce liver damage. See, e.g. Sarkar, R., W. Xiao, and H. H. Kazazian. "A single adeno-associated virus (AAV)-murine factor VIII vector partially corrects the hemophilia A phenotype." Journal of Thrombosis and Haemostasis 1.2 (2003): 220-226; and McIntosh, Jenny, et al. "Therapeutic levels of FVIII following a single peripheral vein administration of rAAV vector encoding a novel human factor VIII variant." Blood 121.17 (2013): 3335-3344.

Thus, more efficient AAV.FVIII vectors are needed for HA treatment.

3. SUMMARY

The embodiments described herein relate to an AAV gene therapy vector for delivering normal human FVIII to a subject in need thereof, following intravenous administration of the vector resulting in long-term, perhaps 10 years or more, of clinically meaningful correction of the bleeding defect. The subject patient population is patients with moderate to severe hemophilia A. The intended vector dose is intended to deliver FVIII blood levels of approximately 3-10% or 5%. The goal for the AAV vector treatment is conversion of severe hemophilia A patients to either moderate or mild hemophilia A thus relieving such patients of the need to be on a prophylaxis regimen.

The gene therapy product described herein provides multiple important advantages to currently available prophylactic approaches to the management of severe Hemophilia A. First, preclinical results with the investigational product are consistent with its potential to achieve circulating levels of Factor VIII of 10% or more of normal, levels which would be transformative in the target patient population. Second, the product should lead to effectively constant Factor VIII blood levels, avoiding the trough levels currently seen with administration of exogenous factor. Third, by only requiring a single administration, the requirement for frequent intravenous administrations could be reduced for an extended period of time, perhaps for a decade or more.

This application provides the use of a replication deficient adeno-associated virus (AAV) to deliver a human Factor VIII (hFVIII or hF8) gene to liver cells of patients (human subjects) diagnosed with hemophilia A. The recombinant AAV vector (rAAV) used for delivering the hFVIII gene ("rAAV.hFVIII") should have a tropism for the liver (e.g., a rAAV bearing an AAVhu.37 or an AAVrh.10 capsid), and the hFVIII transgene should be controlled by liver-specific expression control elements. In one embodiment, the expression control elements include one or more of the following: a transthyretin enhancer (enTTR); a transthyretin (TTR) promoter; and a polyA signal. In another embodiment, the expression control elements include one or more of the following: a shortened α1-microglogulin/bikunin precursor (ABPS) enhancer, and enTTR; a transthyretin (TTR) promoter; and a polyA signal. In one embodiment, the expression control elements include one or more of the following: a transthyretin enhancer (enTTR); an alpha 1 anti-trypsin (A1AT) promoter; and a polyA signal. In another embodiment, the expression control elements include one or more of the following: an ABPS enhancer, and enTTR; an A1AT promoter; and a polyA signal. Such elements are further described herein.

In one embodiment, the hFVIII gene encodes a B-domain deleted (BDD) form of factor VIII, in which the B-domain is replaced by a short amino acid linker (FVIII-BDD-SQ, also referred to herein as hFVIII). In one embodiment, the FVIII-BDD-SQ protein sequence is shown in SEQ ID NO: 3. In one embodiment, the FVIII-BDD-SQ coding sequence is shown in SEQ ID NO: 1. The coding sequence for hFVIII is, in one embodiment, codon optimized for expression in humans. Such sequence may share less than 80% identity to the native hFVIII coding sequence (SEQ ID NO: 1). In one embodiment, the hFVIII coding sequence is that shown in SEQ ID NO: 2.

In another aspect, provided herein is an aqueous suspension suitable for administration to a hemophilia A patient which includes the rAAV described herein. In some embodiments, the suspension includes an aqueous suspending liquid and about $1\times10^{12}$ to about $1\times10^{14}$ genome copies (GC) of the rAAV/mL. The suspension is, in one embodiment, suitable for intravenous injection. In other embodiment, the suspension further includes a surfactant, preservative, and/or buffer dissolved in the aqueous suspending liquid.

In another embodiment, provided herein is a method of treating a patient having hemophilia A with an rAAV as described herein. In one embodiment, about $1\times10^{11}$ to about $3\times10^{13}$ genome copies (GC) of the rAAV/kg patient body weight are delivered the patient in an aqueous suspension.

The goal of the treatment is to functionally replace the patient's defective hFVIII via rAAV-based liver-directed gene therapy as a viable approach to treat this disease and improve response to current therapies. The embodiments described in the application are based, in part, on the development of therapeutic compositions and methods that allow for the safe delivery of efficacious doses; and improved manufacturing methods to meet the purification production requirement for efficacious dosing in human subjects.

4. BRIEF DESCRIPTION OF THE DRAWINGS

Figure 5:
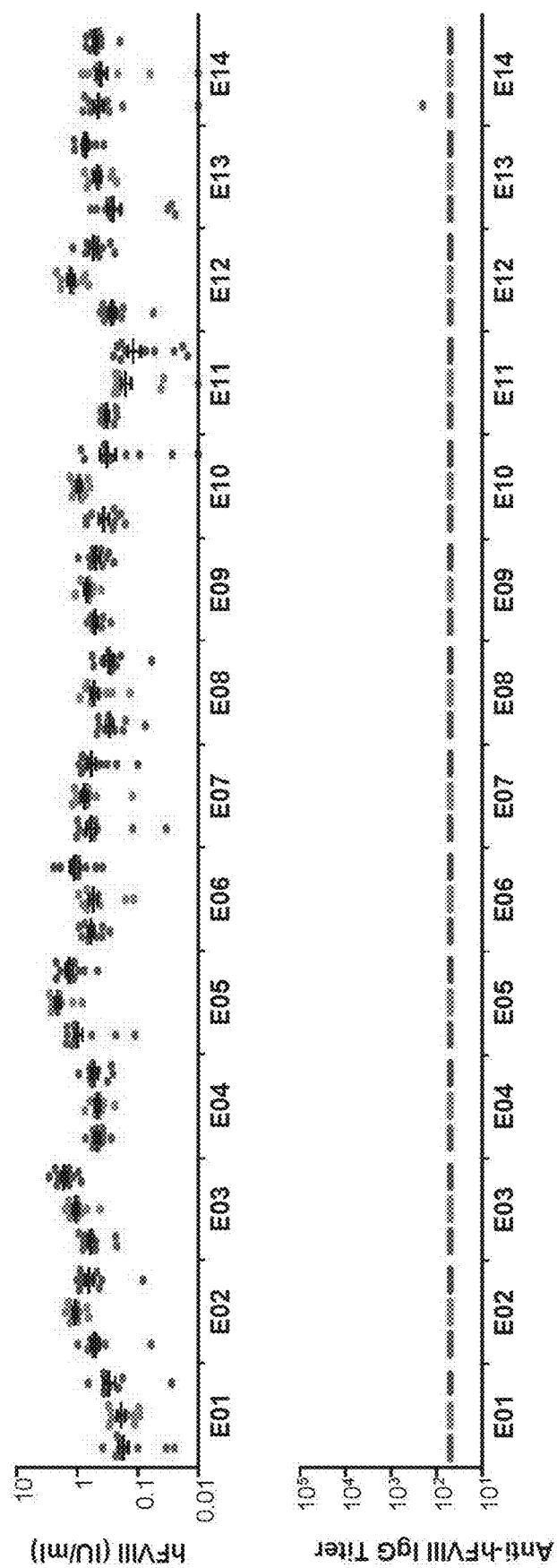

FIG. 5 shows variation in hFVIII activity prior to antibody generation in FVIII KO mice. FVIII KO mice were administered IV with $10^{10}$ GC of AAVrh10 vectors expressing hFVIIIco-SQ from one of the 42 enhancer/promoter combinations. Each of the enhancer arrangements (denoted as E01-E14, Table 1) were combined with the TBG-S1 (left cohort from each grouping), A1AT (middle cohort) and TTR (right cohort) promoters. hFVIII activity (A) and anti-hFVIII IgG titers (B) were determined by COATEST assay and anti-hFVIII IgG ELISA, respectively. Assays were performed on mouse plasma isolated at week 2 post-vector administration. Mice are individually plotted with mean±SEM values for activity shown (n=10/group).

Figure 6:
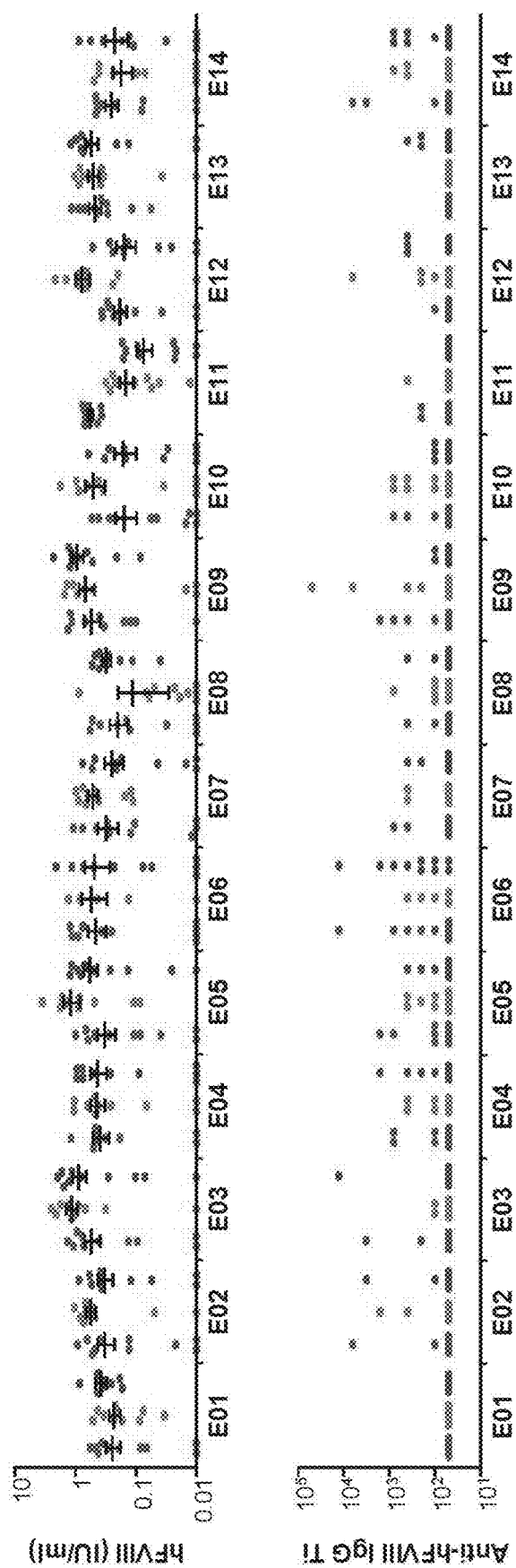

FIG. 6 shows hFVIII activity and anti-hFVIII antibody titer at week 8 following IV vector administration in FVIII KO mice. FVIII KO mice were administered IV with $10^{10}$ GC of AAVrh10 vectors expressing hFVIIIco-SQ from one of the 42 enhancer/promoter combinations. Each of the enhancer arrangements (denoted as E01-E14, Table 1) were combined with the TBG-S1 (left cohort from each grouping), A1AT (middle cohort) and TTR (right cohort) promoters. hFVIII activity (A) and anti-hFVIII IgG titers (B) were determined by COATEST assay and anti-hFVIII IgG ELISA, respectively. Assays were performed on mouse plasma isolated at week 8 post-vector administration. Mice are individually plotted with mean±SEM values for activity shown (n=10/group).

Figure 7:
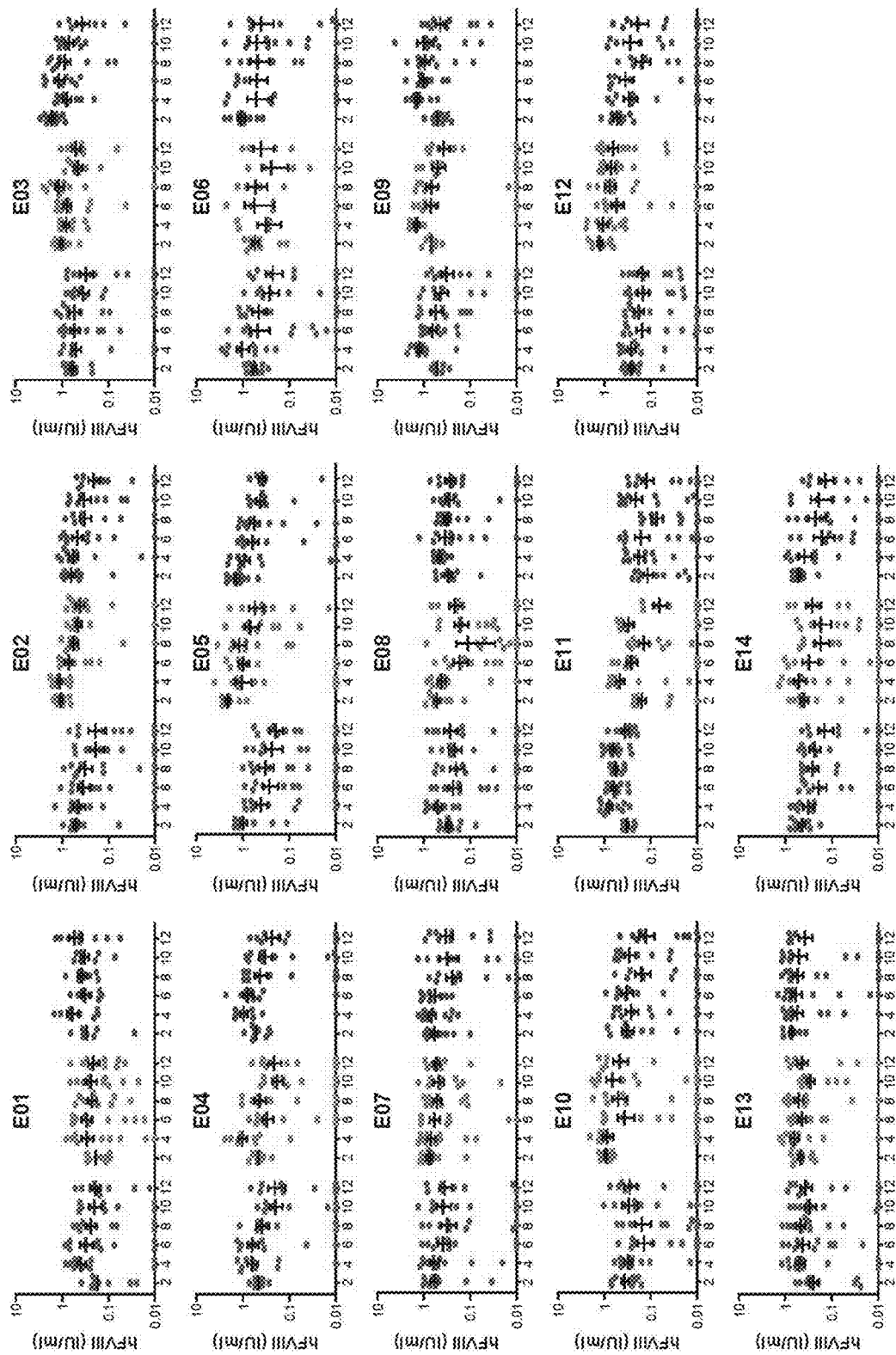

FIG. 7 shows hFVIII activity in FVIII KO mice following IV administration of the 42 enhancer/promoter combination vectors over time. FVIII KO mice were administered IV with $10^{10}$ GC of AAVrh10 vectors expressing hFVIIIco-SQ from one of the 42 enhancer/promoter combinations. Each of the enhancer arrangements (denoted as E01-E14, Table 1) were combined with the TBG-S1 (left cohort from each grouping), A1AT (middle cohort) and TTR (right cohort) promoters. hFVIII activity was determined by COATEST assay on mouse plasma isolated biweekly post-vector administration. Mice are individually plotted with mean±SEM (n=10/group).

Figure 8:
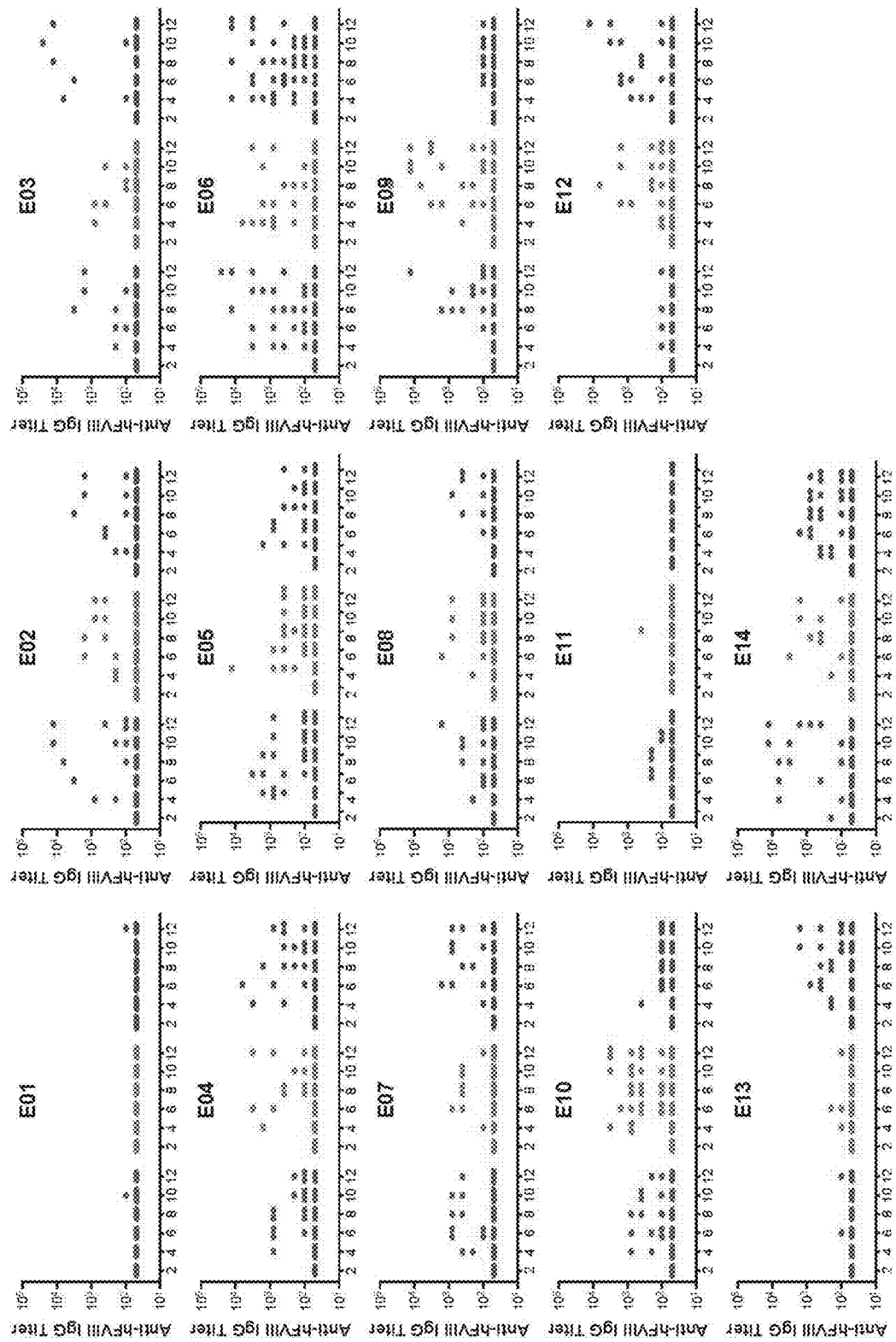

FIG. 8 shows Anti-hFVIII antibody titers in FVIII KO mice following IV administration of the 42 enhancer/promoter combination vectors over time. FVIII KO mice were administered IV with $10^{10}$ GC of AAVrh10 vectors expressing hFVIIIco-SQ from one of the 42 enhancer/promoter combinations. Each of the enhancer arrangements (denoted as E01-E14, Table 1) were combined with the TBG-S1 (left cohort), A1AT (middle cohort) and TTR (right cohort) promoters. Anti-hFVIII IgG titers were determined by anti-hFVIII IgG ELISA on mouse plasma isolated biweekly. Mice are individually plotted (n=10/group).

Figure 9:
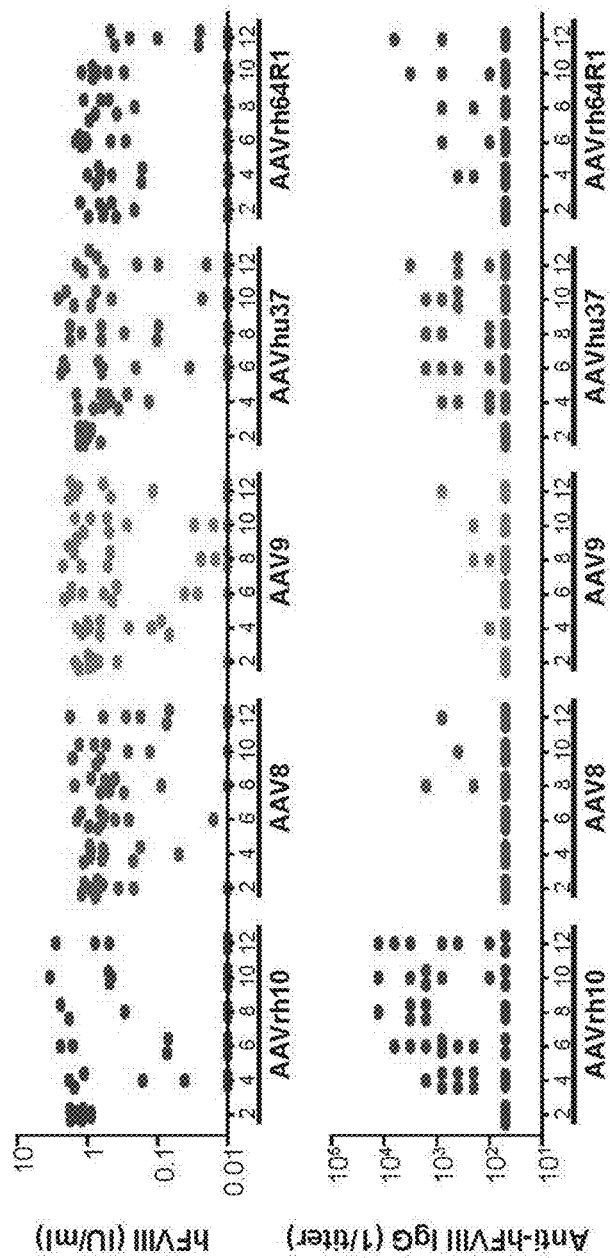

FIG. 9 provides comparison of hFVIII activity and anti-hFVIII antibody titer by following IV administration of the E06.TTR.hFVIIIco-SQ genome by a variety of vector capsids. FVIII KO mice were administered IV with $10^{10}$ GC of AAVrh10, AAV8, AAV9, AAVhu37, or AAVrh64R1 vectors expressing hFVIIIco-SQ from E06.TTR. Plasma was collected biweekly and hFVIII activity (A) and anti-hFVIII IgG titers (B) were determined by COATEST assay and anti-hFVIII IgG ELISA, respectively. Mice are individually plotted with mean±SEM values for activity shown (n=10/group).

Figure 10:
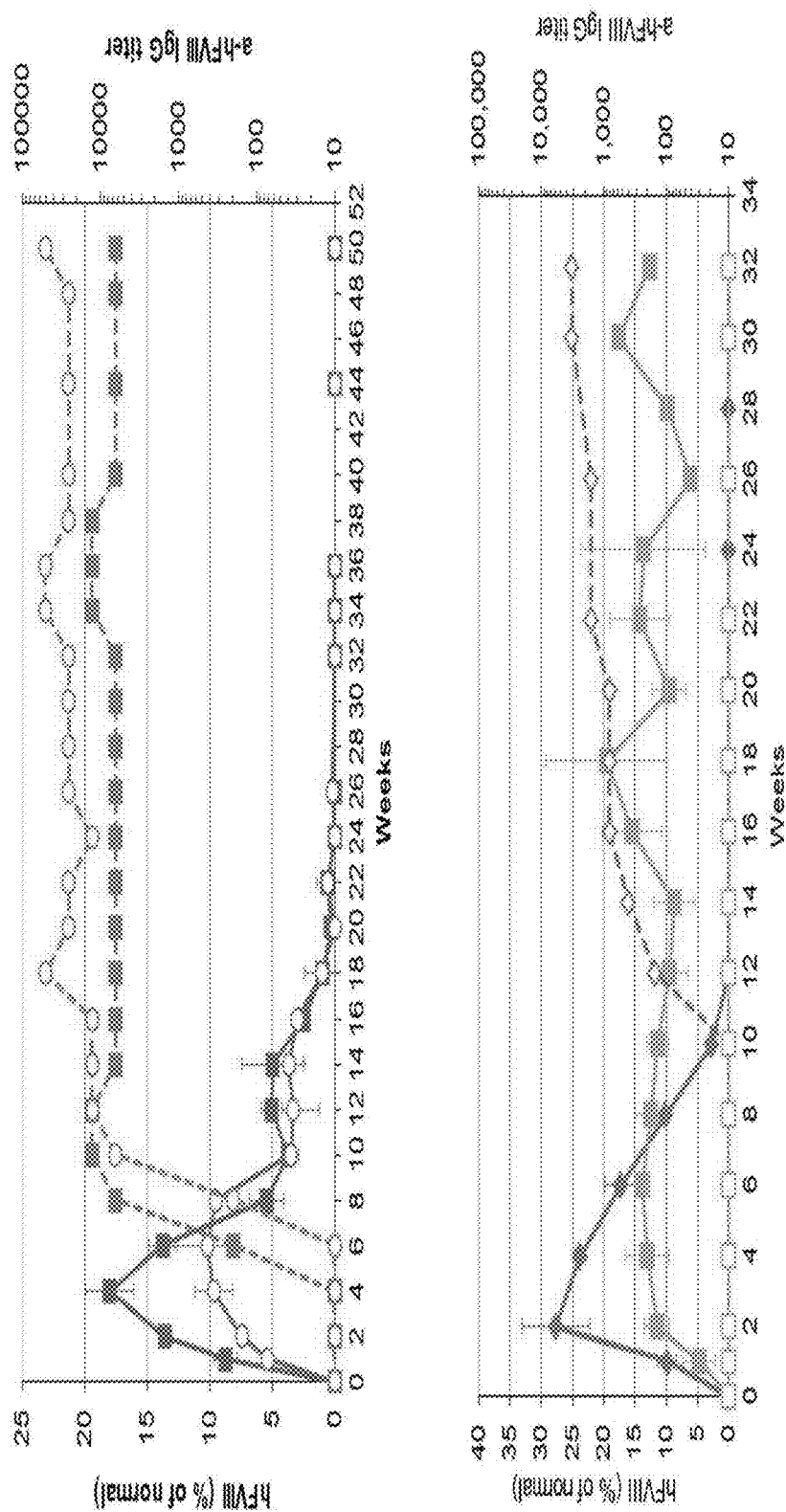

FIG. 10 provides expression of hFVIII in pilot non-human primate (NHP) studies. (A) Two male rhesus macaques were administered IV with $3\times10^{12}$ GC/kg of AAVrh10.ABP2.TBG-S1.hFVIIIco-SQ. (B) Two male cynomolgus macaques were administered IV with $3\times10^{12}$ GC/kg of AAVhu37.ABP2.TBG-S1.hFVIIIco-SQ. Macaques were bled weekly or biweekly to evaluate hFVIII expression and the presence of antibodies against the hFVIII transgene. hFVIII expression was measured in plasma by ELISA (solid line) and values are expressed as mean±SEM. Anti-hFVIII IgG titers were also determined in plasma by ELISA (dotted line).

Figure 11:
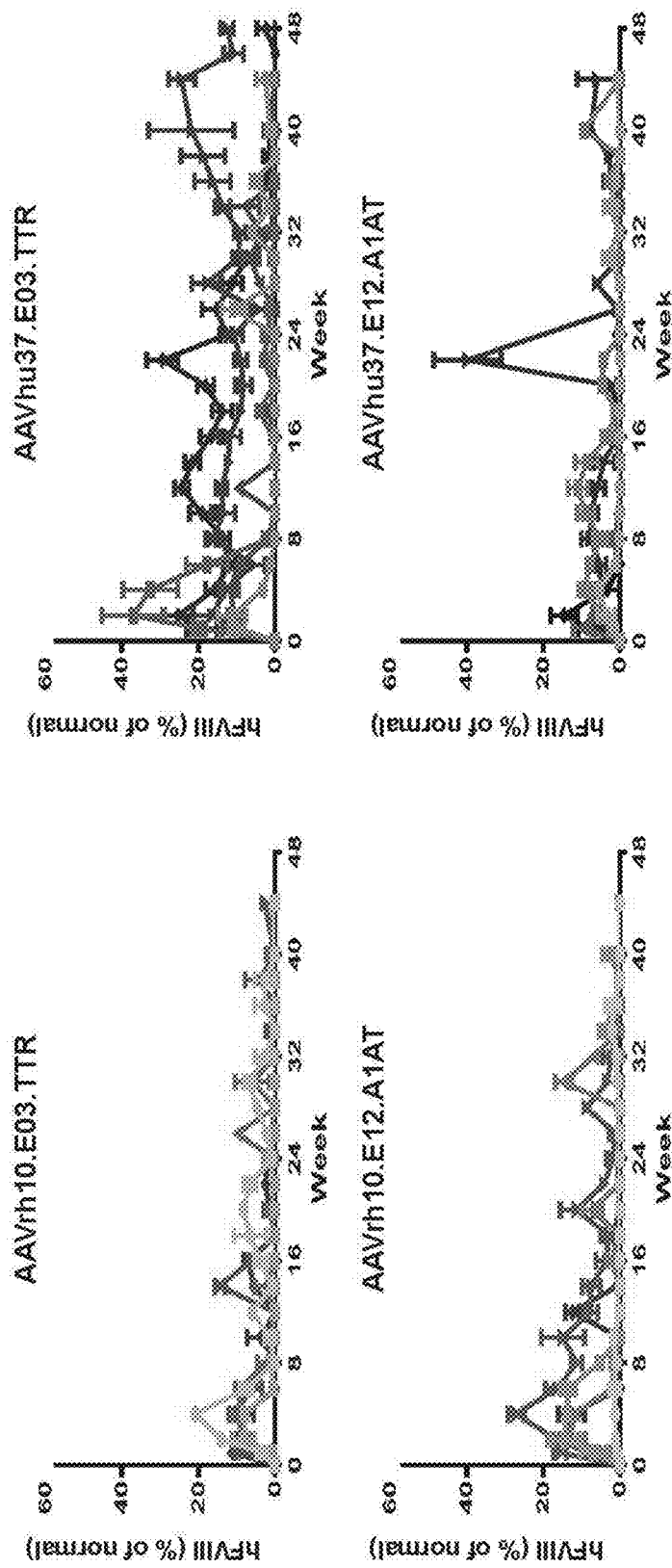

FIG. 11 provides expression of hFVIII in cynomolgus macaques. Five male rhesus macaques were administered IV with $1.2\times10^{13}$ GC/kg of one of AAVrh10.E03.TTR.hFVIIIco-SQ.PA75, AAVrh10.E12.A1AT.hFVIIIco-SQ.PA75, AAVhu37.E03.TTR.hFVIIIco-SQ.PA75, or AAVhu37.E12.A1AT.hFVIIIco-SQ.PA75. Macaques were bled biweekly to evaluate hFVIII expression in plasma by ELISA and values are expressed as mean±SEM.

Figure 12:
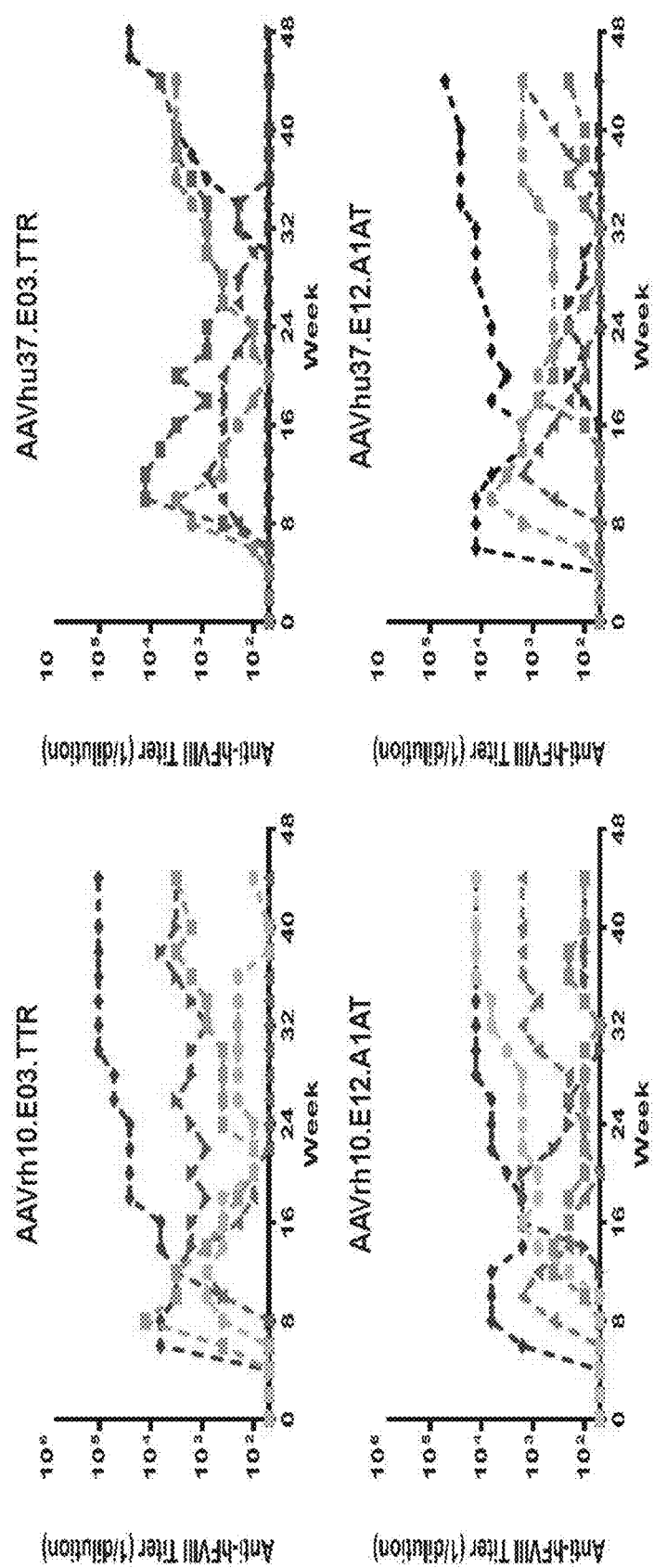

FIG. 12 shows generation of anti-hFVIII antibodies in cynomolgus macaques. Five male rhesus macaques were administered IV with $1.2\times10^{13}$ GC/kg of one of AAVrh10.E03.TTR.hFVIIIco-SQ.PA75, AAVrh10.E12.A1AT.hFVIIIco-SQ.PA75, AAVhu37.E03.TTR.hFVIIIco-SQ.PA75, or AAVhu37.E12.A1AT.hFVIIIco-SQ.PA75. Macaques were bled biweekly to evaluate the presence of antibodies against the hFVIII transgene. Anti-hFVIII IgG titers were evaluated in plasma by ELISA. Statistical analysis is shown in FIG. 14.

Figure 13:
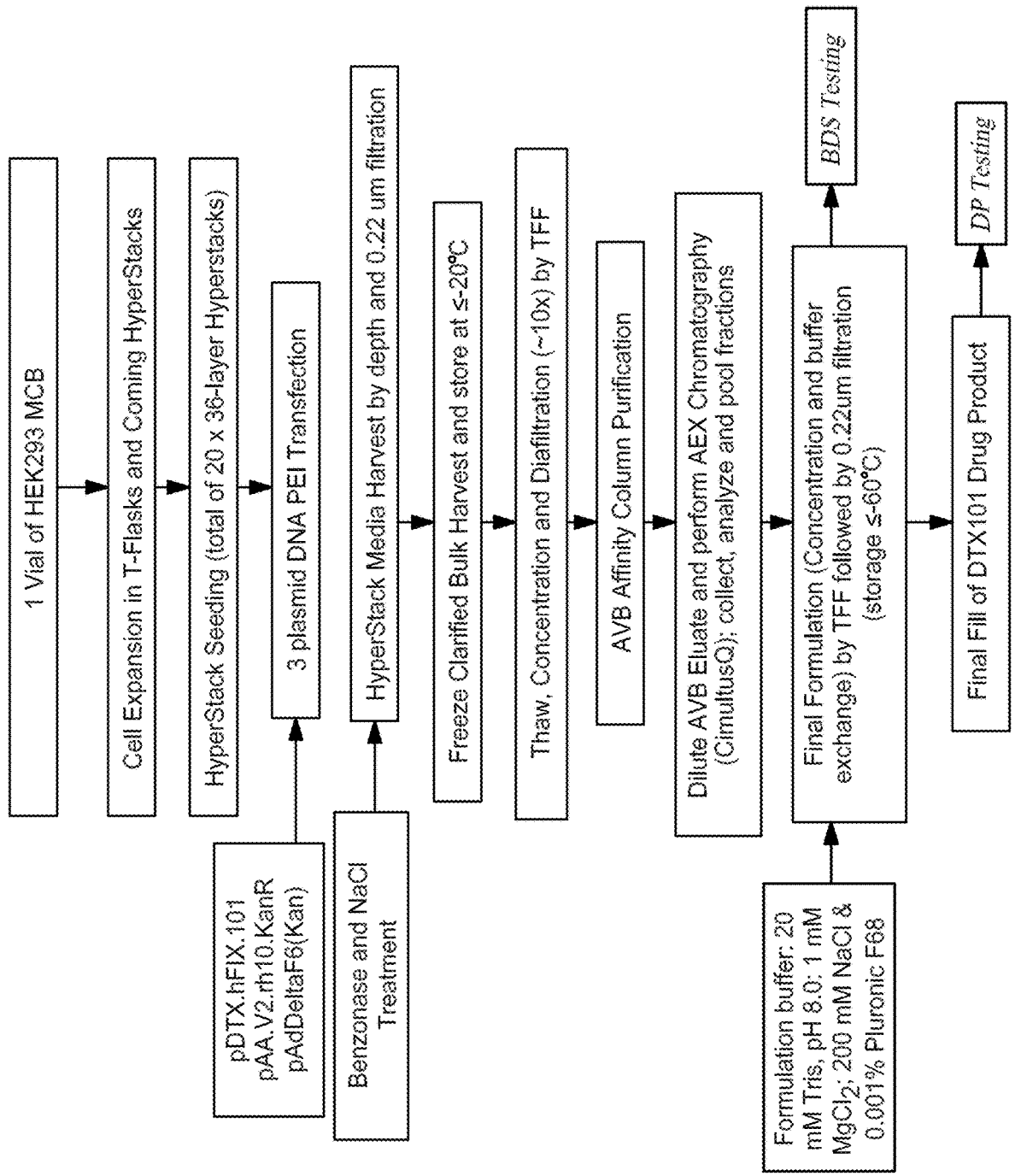

FIG. 13 provides a manufacturing scheme.

Figure 14:
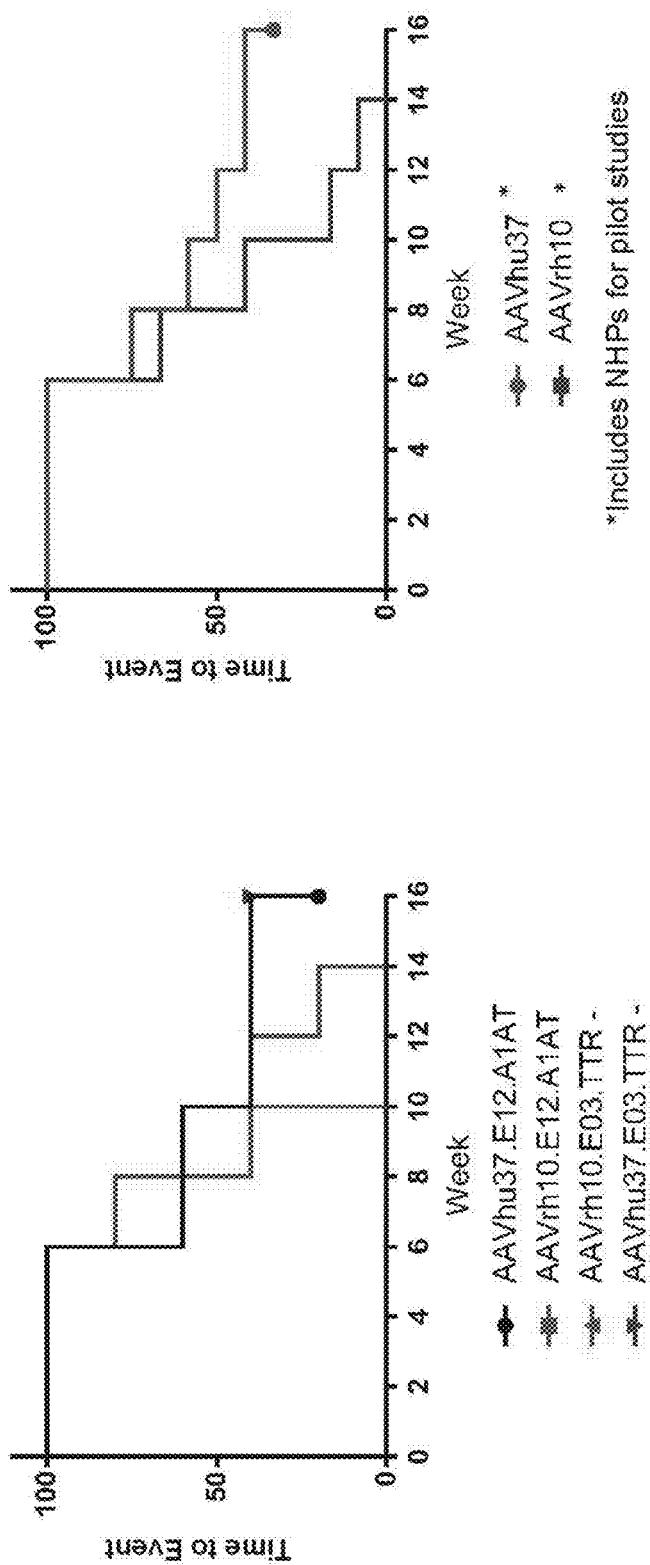

FIG. 14 provides time event analysis of generation of anti-FVIII antibodies shown in FIG. 12. A statistically significant difference was seen between AAVrh.10 and AAVhu.37 using a Log-rank (Mantel-Cox) test.

Figure 15:
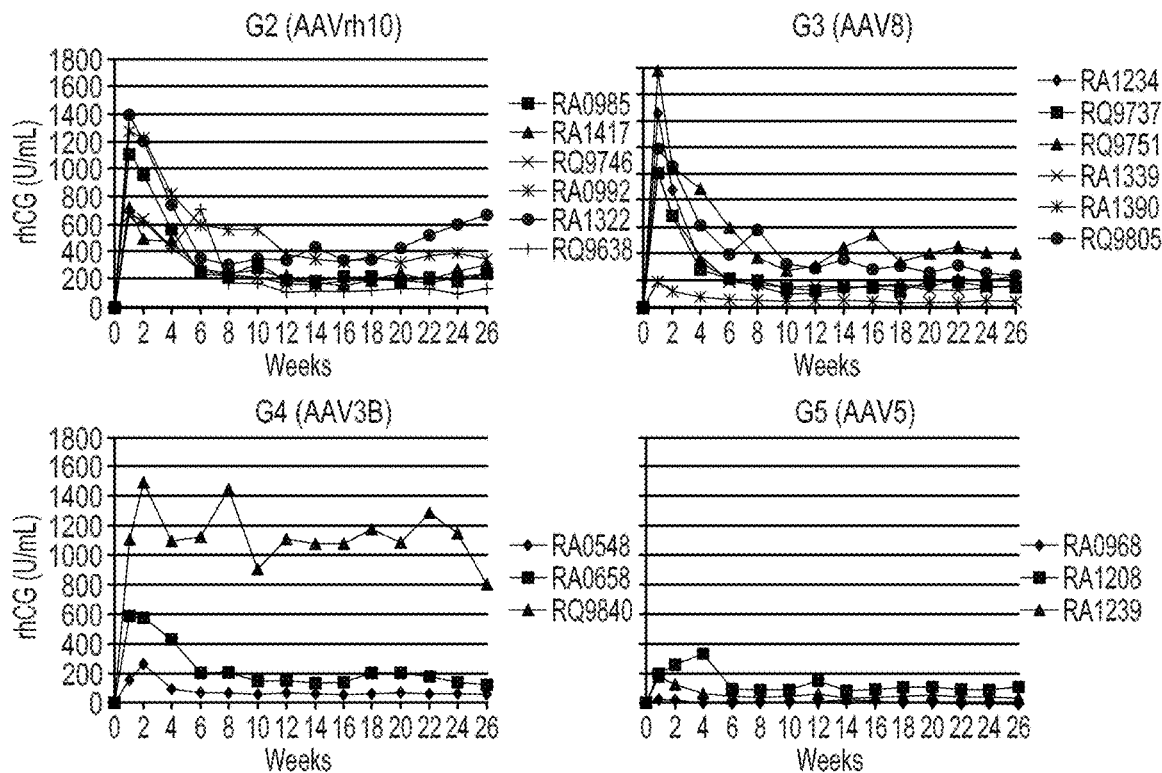

FIG. 15 shows a comparison of rhCG expression levels by AAVrh10, AAV8, AAV3B and AAVS vectors (first vector injection).

Figure 16A:
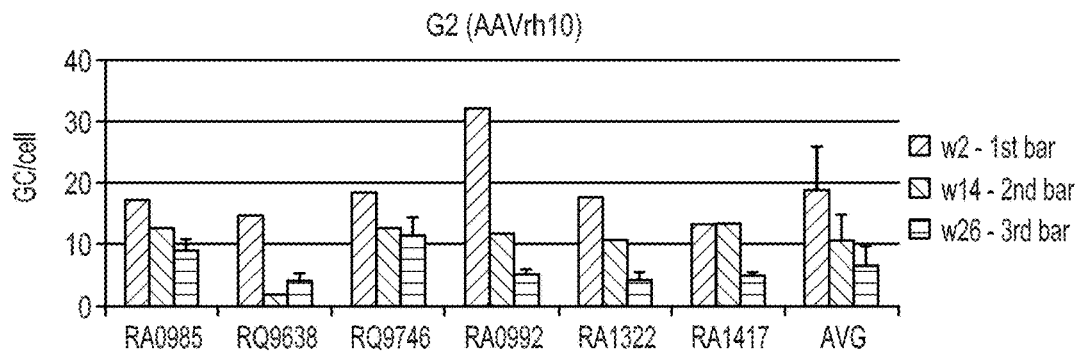
Figure 16B:
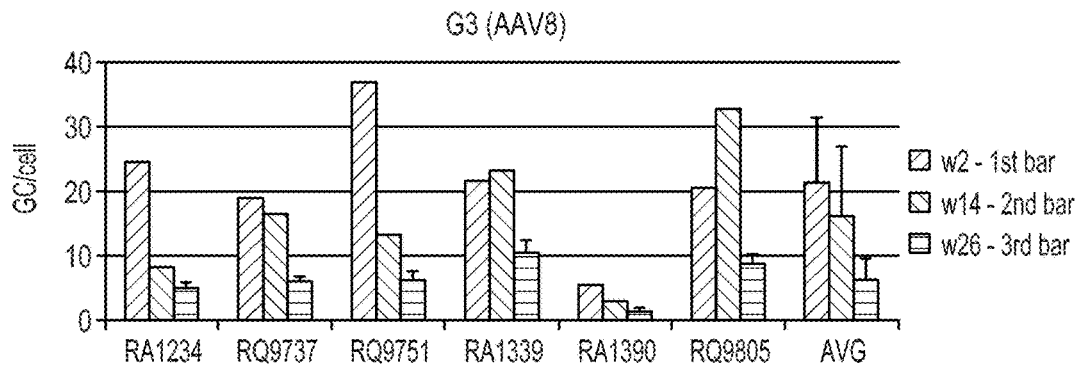
Figure 16C:
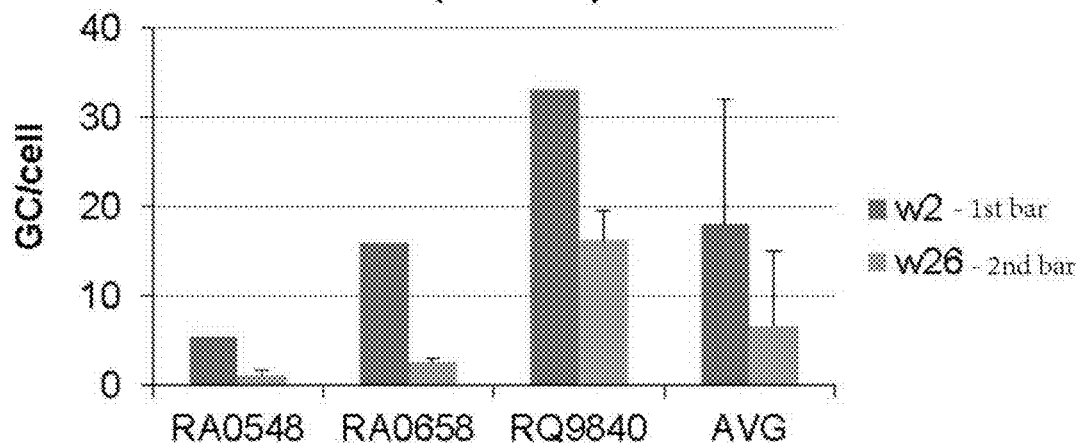
Figure 16D:
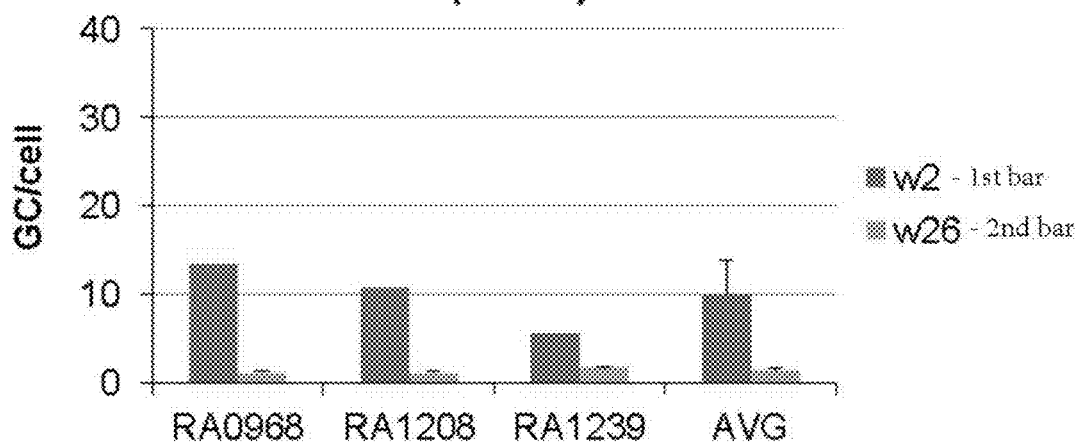

FIGS. 16A-16D show rhCG vector DNA copies in liver at different time points (AAVrh10, FIG. 16A; AAV8, FIG. 16B; AAV3B, FIG. 16C; AAVS, FIG. 16D).

FIGS. 17A-17B show rhAFP levels after readministration (second vector injection) with AAV3B (FIG. 17A) or AAVS (FIG. 17B) vectors expressing rhAFP.

Figure 18A:
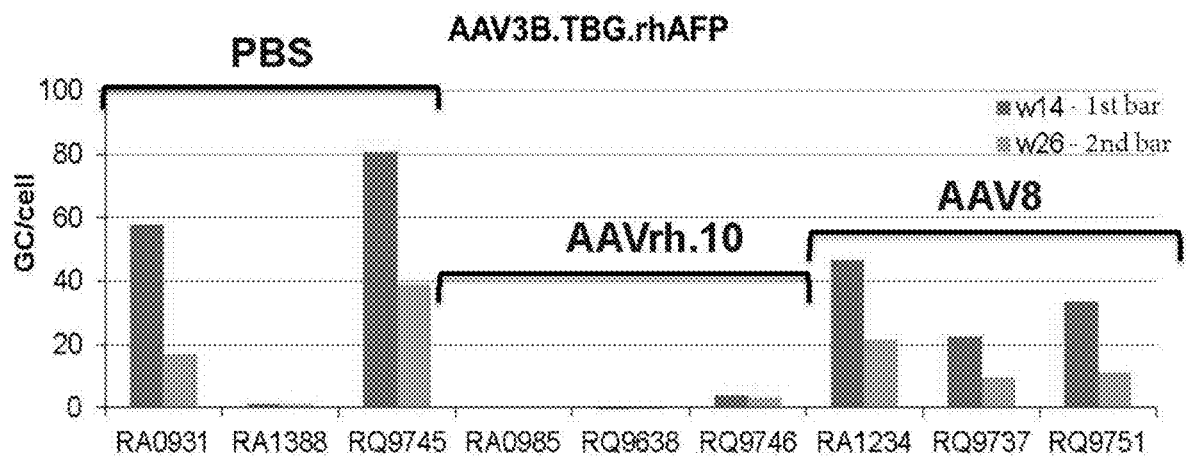
Figure 18B:
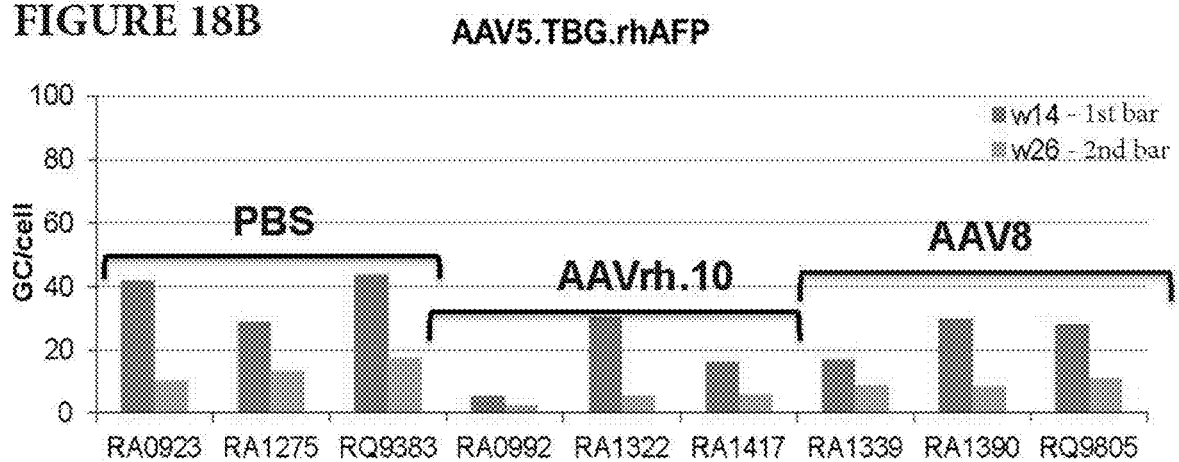

FIGS. 18A-18B show rhAFP vector genome copies in liver (FIG. 18A, AAV3B.TBG.rhAFP; FIG. 18B, AAVS.TBG.rhAFP).

Figure 19:
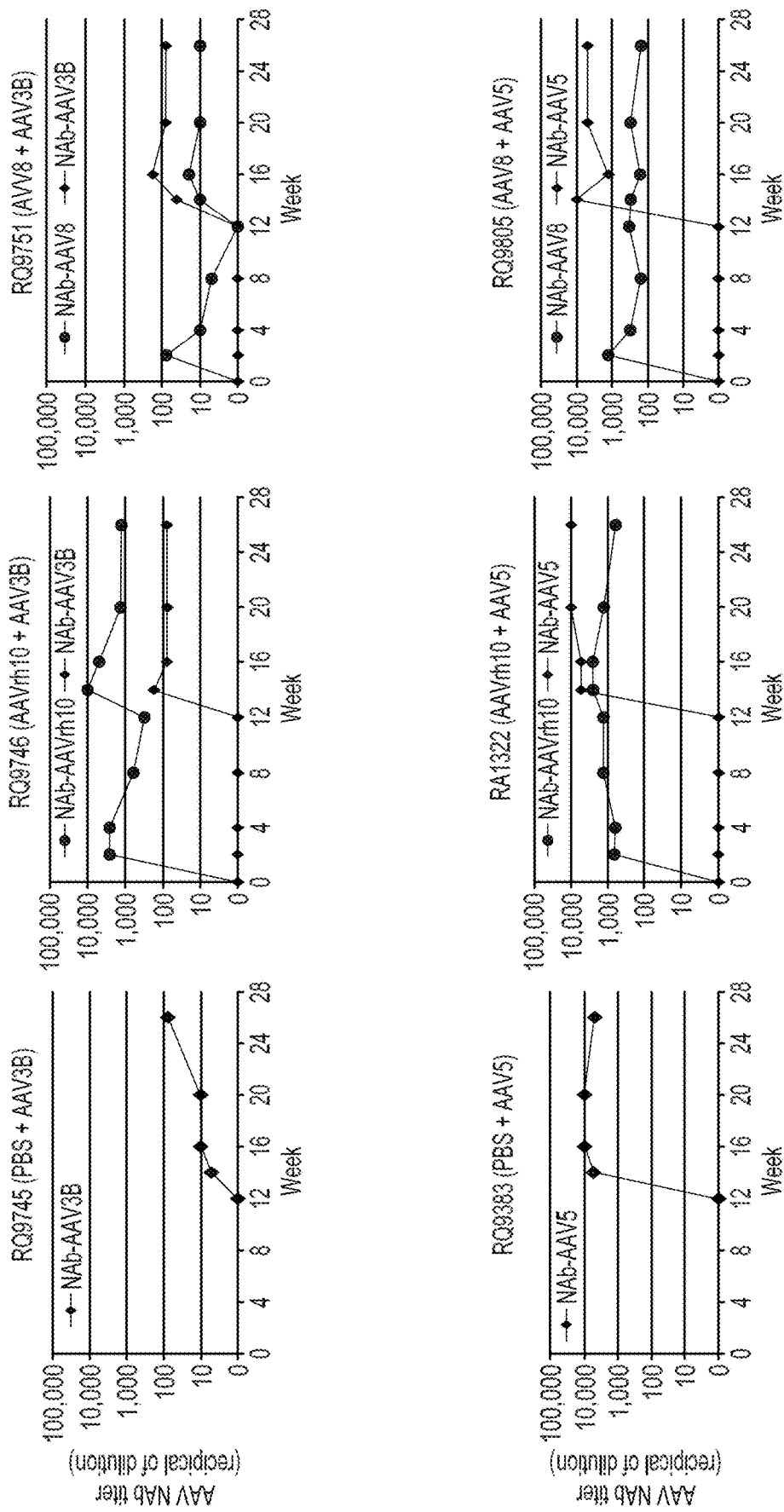

FIG. 19 shows differential AAV Nab response in macaques.

Figure 20A:
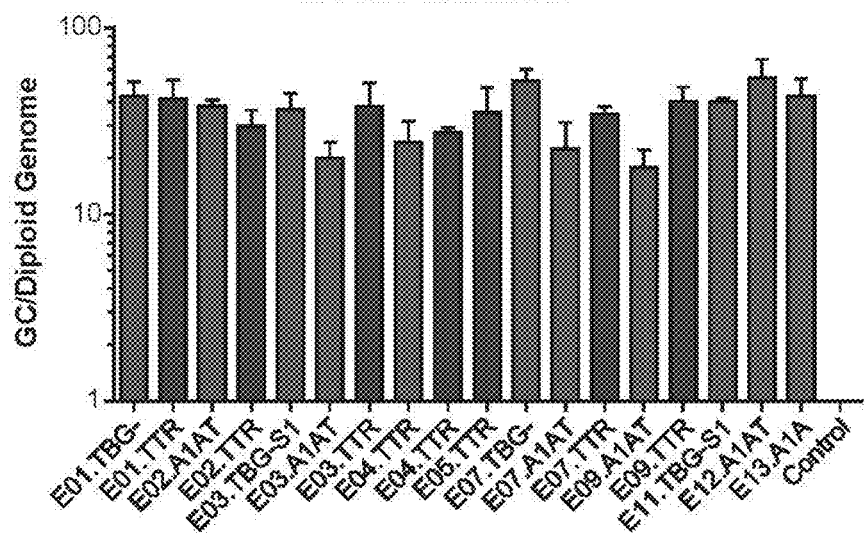
Figure 20B:
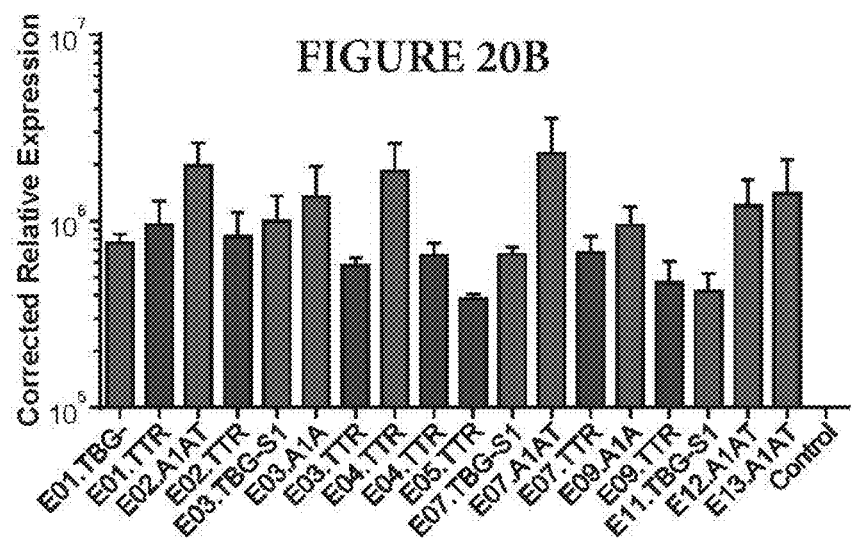

FIGS. 20A-20B provide liver vector GC (FIG. 20A) or RNA transcript levels (FIG. 20B) in liver of mice injected with the AAVrh10 enhancer/promoter vectors expressing hFVIIIco IV as described in Section 6.3.8.

Figure 21:
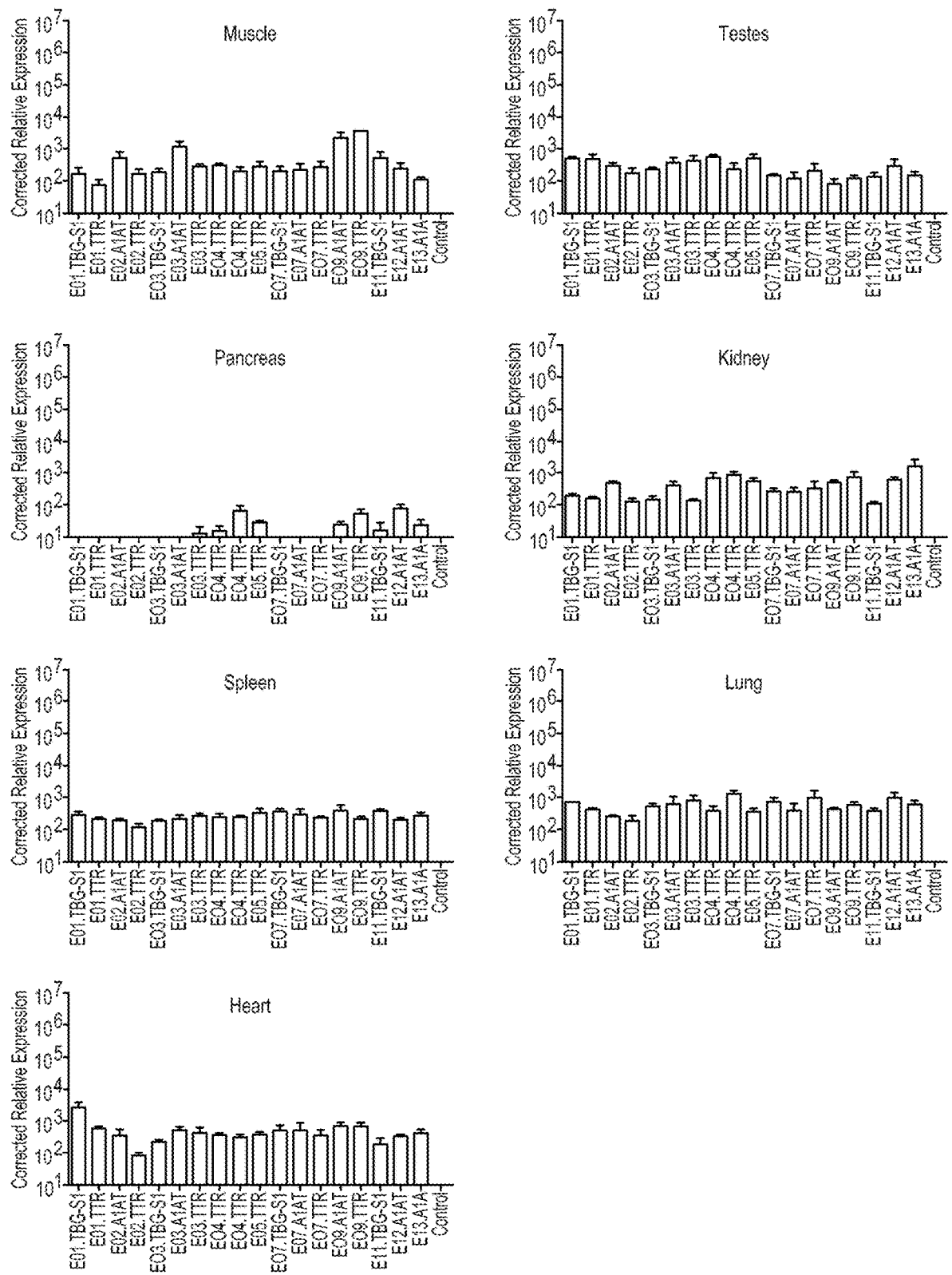

FIG. 21 provides hFVIII RNA transcript levels in muscle (right gastrocnemius), right testis, pancreas, right kidney, spleen, right lung, and heart of mice injected with the AAVrh10 enhancer/promoter vectors expressing hFVIIIco IV as described in Section 6.3.8.

Figure 22:
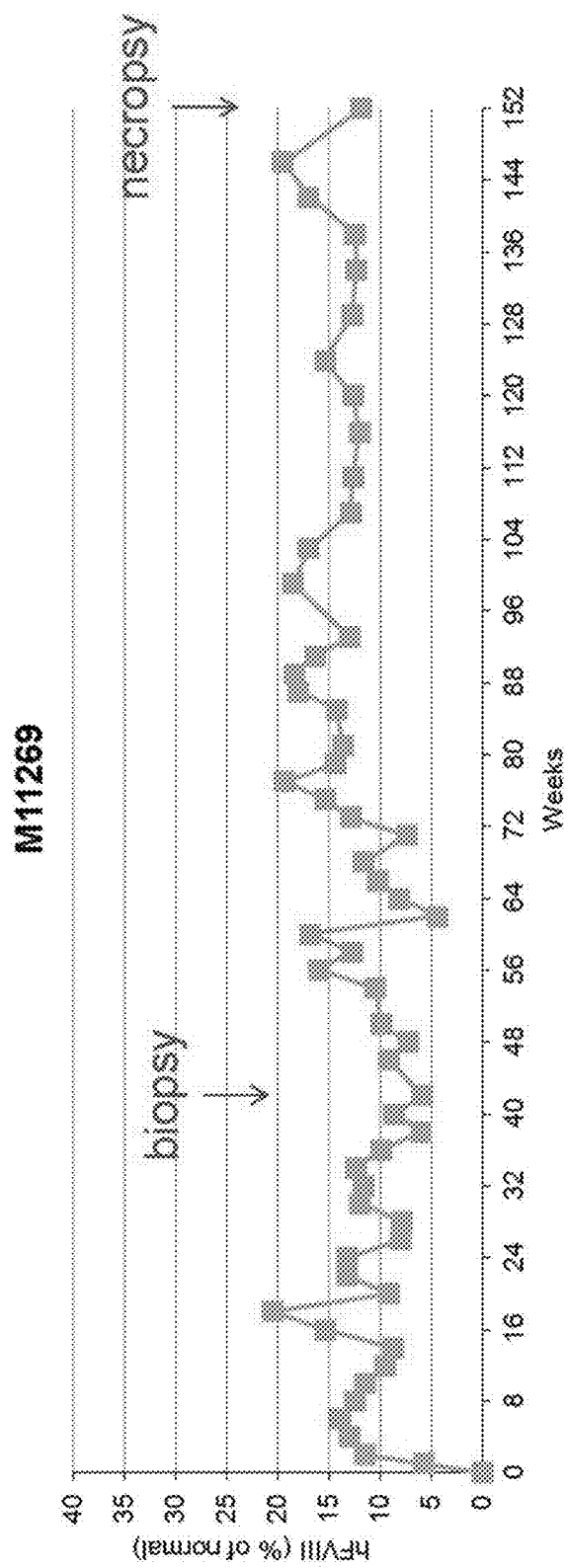

FIG. 22 is a graph showing long-term stable expression of human FVIII in a cynomolgus macaque (35 months) following a single intravenous injection of AAVhu37.TBG-S1.hFVIII-SQ.PA75 at $3 \times 10^{12}$ GC/kg.

Figure 23:
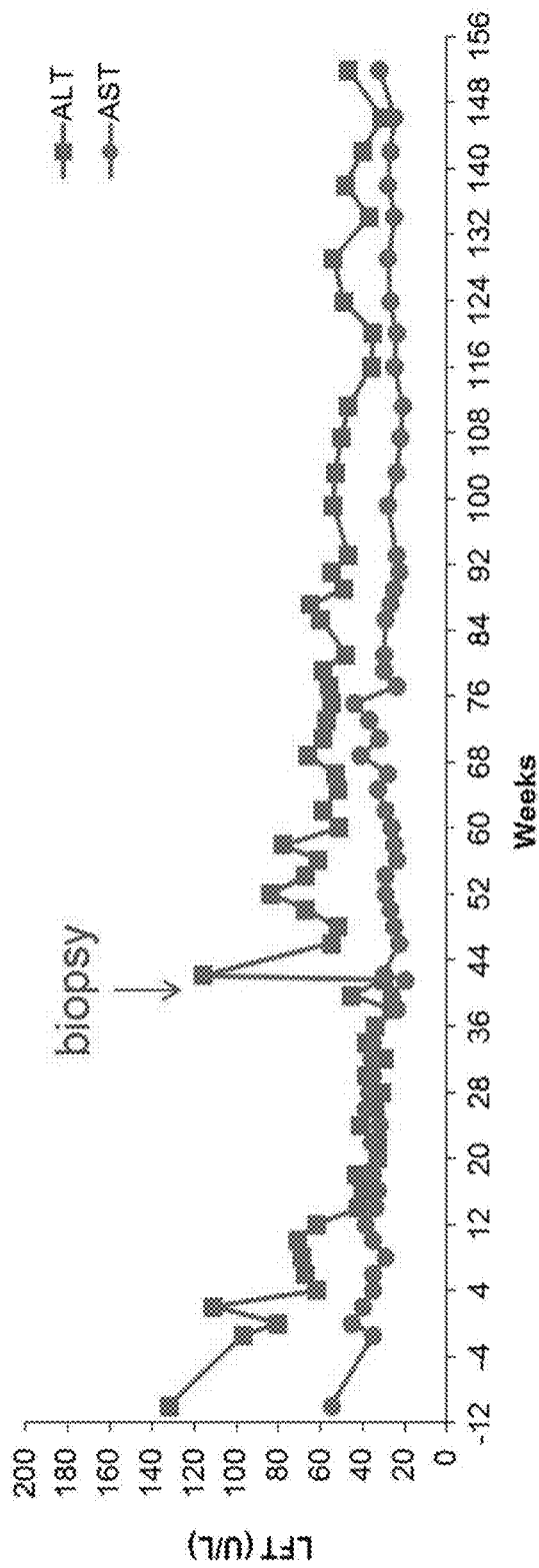

FIG. 23 is a graph showing liver enzyme levels (ALT, U/mL, squares; AST, U/mL, circles) in the macaque of FIG. 22.

Figure 24:
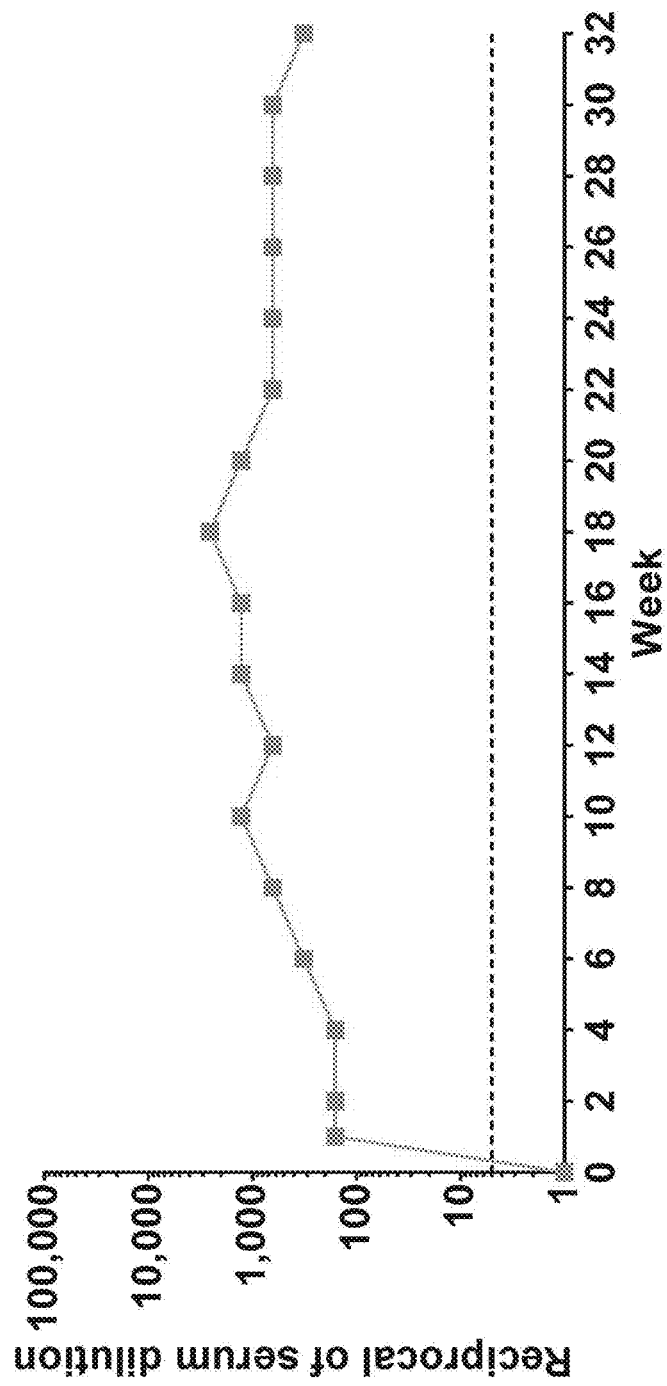

FIG. 24 is a graph showing neutralizing antibody (Nab) response to the AAVhu.37 capsid.

FIG. 25 is an alignment of the hFVIIIco sequence (SEQ ID NO: 2) vs. hFVIII native (SEQ ID NO: 1) sequence.

5. DETAILED DESCRIPTION

The embodiments described in the application relate to the use of a replication deficient adeno-associated virus (AAV) to deliver a human Factor VIII (hFVIII) gene to liver cells of patients (human subjects) diagnosed with hemophilia A (HA). The recombinant AAV vector (rAAV) used for delivering the hFVIII gene ("rAAV.hFVIII") should have a tropism for the liver (e.g., an rAAV bearing an AAVhu.37 or AAVrh.10 capsid), and the hFVIII transgene should be controlled by liver-specific expression control elements. In one embodiment, the expression control elements include one or more of the following: a transthyretin (TTR) enhancer; a transthyretin (TTR) promoter; and a polyA signal. Such elements are further described herein.

As used herein, "AAVhu.37 capsid" refers to the hu.37 having the amino acid sequence of GenBank, accession: AAS99285, SEQ ID NO: 17, which is incorporated by reference herein. Some variation from this encoded sequence is permitted, which may include sequences having about 99% identity to the referenced amino acid sequence in AAS99285 and US 2015/0315612 (which is incorporated herein by reference) (i.e., less than about 1% variation from the referenced sequence). Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003) and US 2015/0315612.

As used herein, "AAVrh10 capsid" refers to the rh.10 having the amino acid sequence of GenBank, accession: AAO88201, SEQ ID NO: 18 which is incorporated by reference herein. Some variation from this encoded sequence is permitted, which may include sequences having about 99% identity to the referenced amino acid sequence in AAO88201 and US 2013/0045186A1 (i.e., less than about 1% variation from the referenced sequence), provided that the integrity of the ligand-binding site for the affinity capture purification is maintained and the change in sequences does not substantially alter the pH range for the capsid for the ion exchange resin purification (as discussed further herein). Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003) and US 2013/0045186A1.

As used herein, the term "NAb titer" a measurement of how much neutralizing antibody (e.g., anti-AAV Nab) is produced which neutralizes the physiologic effect of its targeted epitope (e.g., an AAV). Anti-AAV NAb titers may be measured as described in, e.g., Calcedo, R., et al., Worldwide Epidemiology of Neutralizing Antibodies to Adeno-Associated Viruses. Journal of Infectious Diseases, 2009. 199(3): p. 381-390, which is incorporated by reference herein.

The terms "percent (%) identity", "sequence identity", "percent sequence identity", or "percent identical" in the context of amino acid sequences refers to the residues in the two sequences which are the same when aligned for correspondence. Percent identity may be readily determined for amino acid sequences over the full-length of a protein, polypeptide, about 32 amino acids, about 330 amino acids, or a peptide fragment thereof or the corresponding nucleic acid sequence coding sequencers. A suitable amino acid fragment may be at least about 8 amino acids in length, and may be up to about 700 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using any of a variety of publicly or commercially available Multiple Sequence Alignment Programs. Sequence alignment programs are available for amino acid sequences, e.g., the "Clustal Omega", "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

As used herein, the term "operably linked" refers to both expression control sequences that are contiguous with the gene of interest and expression control sequences that act in trans or at a distance to control the gene of interest.

A "replication-defective virus" or "viral vector" refers to a recombinant, synthetic or artificial viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% from the reference given, unless otherwise specified.

Unless defined otherwise in this specification, technical and scientific terms used herein have the same meaning as commonly understood by one of ordinary skill in the art and by reference to published texts, which provide one skilled in the art with a general guide to many of the terms used in the present application.

5.1 Gene Therapy Vectors

In one aspect, a recombinant adeno-associated virus (rAAV) vector carrying the human clotting factor 8 (hF8 or hFVIII) gene is provided for use in gene therapy. The rAAV.hFVIII vector should have a tropism for the liver (e.g., a rAAV bearing an AAVhu.37 or AAVrh.10 capsid) and the hFVIII transgene should be controlled by liver-specific expression control elements. The vector is formulated in a buffer/carrier suitable for infusion in human subjects. The buffer/carrier should include a component that prevents the rAAV from sticking to the infusion tubing but does not interfere with the rAAV binding activity in vivo.

5.1.1. The rAAV.hFVIII Vector 5.1.1.1. The hFVIII Sequence

Human coagulation factor VIII is produced as a large 330-kDa glycoprotein with the domain structure A1-A2-B-A3-C1-C2, where both the A and C domains have internal sequence homology and approximately 40% sequence identity to the A and C domains of factor V (FV), which shares the same domain structure. The B domain, which constitutes 38% of the total sequence, is dispensable for procoagulant activity. FVIII in which the B domain is deleted (BDD) and replaced by a short 14 amino acid linker (FVIII SQ) is in clinical use as a replacement recombinant FVIII product, and has been shown to result in a 17-fold increase in mRNA levels over full-length wild-type FVIII and a 30% increase in secreted protein. See, McIntosh et al, Therapeutic levels of FVIII following a single peripheral vein administration of rAAV vector encoding a novel human factor VIII variant, Blood, 121(17):3335-44 (February 2013) and Ward et al, Codon optimization of human factor VIII cDNAs leads to high-level expression, Blood, 117(3):798-807 (January 2011), which are incorporated herein by reference.

In one embodiment, the hFVIII gene encodes the hFVIII protein shown in SEQ ID NO: 3, which is a FVIII in which the B domain is deleted (BDD) and replaced by a short 14 amino acid linker (FVIII-BDD-SQ). Thus, in one embodiment, the hFVIII transgene can include, but is not limited to, one or more of the sequences provided by SEQ ID NO:1 or SEQ ID NO: 2 which are provided in the attached Sequence Listing, which is incorporated by reference herein. SEQ ID NO: 1 provides the cDNA for native human FVIII-BDD-SQ. SEQ ID NO: 2 provides an engineered cDNA for human FVIII-BDD-SQ, which has been codon optimized for expression in humans (sometimes referred to herein as hFVIIIco-SQ or hFVIIIco-BDD-SQ). It is to be understood that reference to hFVIII herein may, in some embodiments, refer to the hFVIII-BDD-SQ native or codon optimized sequence. Alternatively or additionally, web-based or commercially available computer programs, as well as service based companies may be used to back translate the amino acid sequences to nucleic acid coding sequences, including both RNA and/or cDNA. See, e.g., backtranseq by EMBOSS, www.ebi.ac.uk/Tools/st/; Gene Infinity (www.geneinfinity.org/sms-/sms_backtranslation.html); ExPasy (www.expasy.org/tools/). It is intended that all nucleic acids encoding the described hFVIII polypeptide sequences are encompassed, including nucleic acid sequences which have been optimized for expression in the desired target subject (e.g., by codon optimization). In one embodiment, the nucleic acid sequence encoding hFVIII shares at least 95% identity with the native hFVIII coding sequence of SEQ ID NO: 1. In another embodiment, the nucleic acid sequence encoding hFVIII shares at least 90, 85, 80, 75, 70, or 65% identity with the native hFVIII coding sequence of SEQ ID NO: 1. In one embodiment, the nucleic acid sequence encoding hFVIII shares about 77% identity with the native hFVIII coding sequence of SEQ ID NO: 1. In one embodiment, the nucleic acid sequence encoding hFVIII is SEQ ID NO: 2. In another embodiment, the nucleic acid sequence encoding hFVIII shares at least 99%, 97%, 95%, 90%, 85%, 80%, 75%, 70%, or 65% identity with the hFVIII coding sequence of SEQ ID NO: 1 or SEQ ID NO: 2. In another embodiment, the nucleic acid sequence encoding hFVIII is SEQ ID NO: 19. In another embodiment, the nucleic acid sequence encoding hFVIII shares at least 90, 85, 80, 75, 70, or 65% identity with the hFVIII coding sequence of SEQ ID NO: 19. In yet another embodiment, the nucleic acid sequence encoding hFVIII shares at least 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identity with the hFVIII coding sequence of SEQ ID NO: 1 or SEQ ID NO: 2. In yet another embodiment, the nucleic acid sequence encoding hFVIII shares at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identity with the hFVIII coding sequence of SEQ ID NO: 19. See, Ward et al, Codon optimization of human factor VIII cDNAs leads to high-level expression, Blood, 117(3):798-807 (January 2011), which is incorporated herein by reference for a discussion of various variants of FVIII-SQ, including codon optimized variants.

Codon-optimized coding regions can be designed by various different methods. This optimization may be performed using methods which are available on-line (e.g., GeneArt), published methods, or a company which provides codon optimizing services, e.g., as DNA2.0 (Menlo Park, Calif.). One codon optimizing approach is described, e.g., in International Patent Publication No. WO 2015/012924, which is incorporated by reference herein. See also, e.g., US Patent Publication No. 2014/0032186 and US Patent Publication No. 2006/0136184. Suitably, the entire length of the open reading frame (ORF) for the product is modified. However, in some embodiments, only a fragment of the ORF may be altered. By using one of these methods, one can apply the frequencies to any given polypeptide sequence, and produce a nucleic acid fragment of a codon-optimized coding region which encodes the polypeptide.

A number of options are available for performing the actual changes to the codons or for synthesizing the codon-optimized coding regions designed as described herein. Such modifications or synthesis can be performed using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides are designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Thermo Fisher Scientific Inc. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

5.1.1.2. The rAAV Vector

Because hFVIII is natively expressed in the liver, it is desirable to use an AAV which shows tropism for liver. In one embodiment, the AAV supplying the capsid is AAVrh.37. In another embodiment, the AAV supplying the capsid is AAVrh.10. However, any of a number of rAAV vectors with liver tropism can be used.

In a specific embodiment described in the Examples, infra, the gene therapy vector is an AAVhu.37 vector expressing an hFVIII transgene under control of a transthyretin promoter referred to as rAAVhu.37.TTR.hFVIII. The external AAV vector component is a serotype hu.37, T=1 icosahedral capsid consisting of 60 copies of three AAV viral proteins, VP1, VP2, and VP3, at a ratio of 1:1:10. The capsid contains a single-stranded DNA rAAV vector genome.

The rAAVhu.37.TTR.hFVIII genome contains an hFVIII transgene flanked by two AAV inverted terminal repeats (ITRs). The hFVIII transgene includes an enhancer, promoter, an hFVIII coding sequence, and polyadenylation (polyA) signal. These control sequences are "operably linked" to the hFVIII gene sequences. The expression cassette may be engineered onto a plasmid which is used for production of a viral vector.

The ITRs are the genetic elements responsible for the replication and packaging of the genome during vector production and are the only viral cis elements required to generate rAAV. The minimal sequences required to package the expression cassette into an AAV viral particle are the AAV 5' and 3' ITRs, which may be of the same AAV origin as the capsid, or which of a different AAV origin (to produce an AAV pseudotype). In one embodiment, the ITR sequences from AAV2, or the deleted version thereof (ΔITR), are used. However, ITRs from other AAV sources may be selected. Where the source of the ITRs is from AAV2 and the AAV capsid is from another AAV source, the resulting vector may be termed pseudotyped. Typically, an expression cassette for an AAV vector comprises an AAV 5' ITR, the hFVIII coding sequences and any regulatory sequences, and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and 3' ITRs are used. In one embodiment, the 5' ITR sequence is shown in SEQ ID NO: 11. In one embodiment, the 3' ITR sequence is shown in SEQ ID NO: 12.

Expression of the hFVIII coding sequence is driven from a liver-specific promoter. Because of the size of the hFVIII transgene, the use of promoter of relatively small size is desirable. An illustrative plasmid and vector described herein uses the transthyretin (TTR) (also referred to herein as P3) promoter, or a modified version thereof. The TTR promoter sequence is shown in SEQ ID NO: 7. Alternatively, other liver-specific promoters may be used such as the thyroxin binding globulin (TBG) (also referred to herein as P1) promoter, or a shortened version thereof, TBG-S1, which sequence is shown in SEQ ID NO: 8. Another suitable promoter is the alpha 1 anti-trypsin (A1AT), or a modified version thereon (also referred to herein as P2), shown in SEQ ID NO: 9. Other suitable promoters include human albumin (Miyatake et al., J. Virol., 71:5124 32 (1997)), humAlb; and hepatitis B virus core promoter, (Sandig et al., Gene Ther., 3:1002 9 (1996). See, e.g., The Liver Specific Gene Promoter Database, Cold Spring Harbor, rulai.s-chl.edu/LSPD, which is incorporated by reference. Although less desired, other promoters, such as viral promoters, constitutive promoters, regulatable promoters [see, e.g., WO 2011/126808 and WO 2013/04943], or a promoter responsive to physiologic cues may be used may be utilized in the vectors described herein.

In one embodiment, the expression control sequences include one or more enhancer. In one embodiment the transthyretin (enTTR) (100 bp enhancer sequence from transthyretin) is included, which sequence is shown in SEQ ID NO: 5. See, Wu et al, Molecular Therapy, 16(2):280-289, February 2008, which is incorporated herein by reference. In another embodiment, the En34 enhancer is included (34 bp core enhancer from the human apolipoprotein hepatic control region), which is shown in SEQ ID NO: 4. In yet another embodiment, the ABPS (shortened version of the 100 bp distal enhancer from the α1-microglogulin/bikunin precursor [ABP] to 42 bp) enhancer is included. Such sequence is shown in SEQ ID NO: 6. In another embodiment, more than one enhancer is present. Such combination may include more than one copy of any of the enhancers described herein, and/or more than one type of enhancer. In various embodiments, the enhancers are present in one of the following combinations:

TABLE 1

Enhancer combinations

| Combination name | En34 | ABPS | EnTTR | Net length (bp) |
|---|---|---|---|---|
| E01 | 1 | 0 | 0 | 34 |
| E02 | 0 | 1 | 0 | 42 |
| E03 | 0 | 0 | 1 | 100 |
| E04 | 1 | 1 | 0 | 76 |
| E05 | 0 | 1 | 1 | 142 |
| E06 | 1 | 0 | 1 | 134 |
| E07 | 2 | 0 | 0 | 68 |
| E08 | 0 | 2 | 0 | 84 |
| E09 | 0 | 0 | 2 | 200 |
| E10 | 1 | 1 | 1 | 176 |
| E11 | 2 | 0 | 1 | 168 |
| E12 | 0 | 2 | 1 | 184 |
| E13 | 1 | 2 | 0 | 118 |
| E14 | 2 | 1 | 0 | 110 |

In one embodiment, the enhancers are combined in the following sequence: 5'-EnTTR-ABPS-En34-Promoter-3'. In another embodiment, the enhancers are combined in the following sequence: 5'-Promoter-EnTTR-ABPS-En34-3'. In one embodiment, the expression control sequences include enTTR. In another embodiment, the expression control sequences include two copies of ABPS and 1 copy of enTTR.

In addition to a promoter, an expression cassette and/or a vector may contain other appropriate transcription initiation, termination, enhancer sequences, and efficient RNA processing signals. Such sequences include splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. In one embodiment, a polyadenylation (polyA) signal is included to mediate termination of hFVIII mRNA transcripts. A polyA signal useful herein is an artificial polyA which is about 75 bp in size (PA75) shown in SEQ ID NO: 10. Examples of other suitable polyA sequences include, e.g., bovine growth hormone, SV40, rabbit beta globin, and TK polyA, amongst others.

In one embodiment, the regulatory sequences are selected such that the total rAAV vector genome is about 5 to about 5.5 kilobases in size. In another embodiment, the regulatory sequences are selected such that the total rAAV vector genome is about 5.1 kb in size. In another embodiment, the regulatory sequences are selected such that the total rAAV vector genome is about 5.2 kb in size. In another embodiment, the total rAAV vector genome is less than 5 kb in size.

In one embodiment, the vector genome is nt 1 to nt 5110 of SEQ ID NO: 13. In one embodiment, the vector genome is nt 1 to nt 5194 of SEQ ID NO: 14. In one embodiment, the vector genome is nt 1 to nt 5138 of SEQ ID NO: 15. In another embodiment, the vector genome is nt 1 to nt 5222 of SEQ ID NO: 16.

5.1.2. rAAV.hFVIII Formulation

In one embodiment, the rAAV.hFVIII vector is provided in a pharmaceutical composition which comprises an aqueous carrier, excipient, diluent or buffer. In one embodiment, the buffer is PBS. In a specific embodiment, the rAAV.hFVIII formulation is a suspension containing an effective amount of rAAV.hFVIII vector suspended in an aqueous solution containing 0.001% Pluronic F-68 in TMN200 (200 mM sodium chloride, 1 mM magnesium chloride, 20 mM Tris, pH 8.0). However, various suitable solutions are known including those which include one or more of: buffering saline, a surfactant, and a physiologically compatible salt or mixture of salts adjusted to an ionic strength equivalent to about 100 mM sodium chloride (NaCl) to about 250 mM sodium chloride, or a physiologically compatible salt adjusted to an equivalent ionic concentration.

For example, a suspension as provided herein may contain both NaCl and KCl. The pH may be in the range of 6.5 to 8.5, or 7 to 8.5, or 7.5 to 8. A suitable surfactant, or combination of surfactants, may be selected from among Poloxamers, i.e., nonionic triblock copolymers composed of a central hydrophobic chain of polyoxypropylene (poly (propylene oxide)) flanked by two hydrophilic chains of polyoxyethylene (poly(ethylene oxide)), SOLUTOL HS 15 (Macrogol-15 Hydroxystearate), LABRASOL (Polyoxy caprylic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension. In another embodiment, the vector is suspended in an aqueous solution containing 180 mM sodium chloride, 10 mM sodium phosphate, 0.001% Poloxamer 188, pH 7.3.

In one embodiment, the formulation is suitable for use in human subjects and is administered intravenously. In one embodiment, the formulation is delivered via a peripheral vein by bolus injection. In one embodiment, the formulation is delivered via a peripheral vein by infusion over about 10 minutes (±5 minutes). In one embodiment, the formulation is delivered via a peripheral vein by infusion over about 90 minutes (±10 minutes). In another embodiment, the formulation is delivered via a peripheral vein by infusion over about 20 minutes (±5 minutes). In another embodiment, the formulation is delivered via a peripheral vein by infusion over about 30 minutes (±5 minutes). In another embodiment, the formulation is delivered via a peripheral vein by infusion over about 40 minutes (±5 minutes). In another embodiment, the formulation is delivered via a peripheral vein by infusion over about 50 minutes (±5 minutes). In another embodiment, the formulation is delivered via 15 a peripheral vein by infusion over about 60 minutes (±5 minutes). In another embodiment, the formulation is delivered via a peripheral vein by infusion over about 70 minutes (±5 minutes). In another embodiment, the formulation is delivered via a peripheral vein by infusion over about 80 minutes (±5 minutes). However, this time may be adjusted as needed or desired. Any suitable method or route can be used to administer an AAV-containing composition as described herein, and optionally, to co-administer other active drugs or therapies in conjunction with the AAV-mediated delivery of hFVIII described herein. Routes of administration include, for example, systemic, oral, inhalation, intranasal, intratracheal, intraarterial, intraocular, intravenous, intramuscular, subcutaneous, intradermal, and other parenteral routes of administration.

In one embodiment, the formulation may contain, e.g., about $1.0 \times 10^{11}$ genome copies per kilogram of patient body weight (GC/kg) to about $1 \times 10^{14}$ GC/kg, about $5 \times 10^{11}$ genome copies per kilogram of patient body weight (GC/kg) to about $3 \times 10^{13}$ GC/kg, or about $1 \times 10^{12}$ to about $1 \times 10^{14}$ GC/kg, as measured by oqPCR or digital droplet PCR (ddPCR) as described in, e.g., M. Lock et al, Hum Gene Ther Methods. 2014 Apr. 25 (2):115-25. doi: 10.1089/hgtb.2013.131. Epub 2014 Feb. 14, which is incorporated herein by reference. In one embodiment, the rAAV.hFVIII formulation is a suspension containing at least $1 \times 10^{13}$ genome copies (GC)/mL, or greater, as measured by oqPCR or digital droplet PCR (ddPCR) as described in, e.g., M. Lock et al, supra.

In order to ensure that empty capsids are removed from the dose of AAV.hFVIII that is administered to patients, empty capsids are separated from vector particles during the vector purification process, e.g., using the method discussed herein. In one embodiment, the vector particles containing packaged genomes are purified from empty capsids using the process described in International Patent Application No. PCT/US2016/066013, filed Dec. 9, 2016 and U.S. Patent Appln No. 62/322,055, filed on Apr. 13, 2016, and entitled "Scalable Purification Method for AAVrh.10", which is incorporated by reference herein. Briefly, a two-step purification scheme is described which selectively captures and isolates the genome-containing rAAV vector particles from the clarified, concentrated supernatant of a rAAV production cell culture. The process utilizes an affinity capture method performed at a high salt concentration followed by an anion exchange resin method performed at high pH to provide rAAV vector particles which are substantially free of rAAV intermediates. Similar purification methods can be used for AAVhu.37 based vectors. Other purification methods are described, e.g., in U.S. Patent Application Nos. 62/266,347, 62/266,357, 62/322,071, 62/266,351, 62/322,083, 62/266, 341, and 62/322,098, each of which is incorporated herein by reference.

While any conventional manufacturing process can be utilized, the process described herein (and in International Patent Application No. PCT/US2016/066013) yields vector preparations wherein between 50 and 70% of the particles have a vector genome, i.e., 50 to 70% full particles. Thus for an exemplary dose of $1.6 \times 10^{12}$ GC/kg, and the total particle dose will be between $2.3 \times 10^{12}$ and $3 \times 10^{12}$ particles. In another embodiment, the proposed dose is one half log higher, or $5 \times 10^{12}$ GC/kg, and the total particle dose will be between $7.6 \times 10^{12}$ and $1.1 \times 10^{13}$ particles. In one embodiment, the formulation is be characterized by an rAAV stock having a ratio of "empty" to "full" of 1 or less, preferably less than 0.75, more preferably, 0.5, preferably less than 0.3.

Briefly, in one embodiment, a method for separating AAV viral particles from AAV capsid intermediates is provided which involves: subjecting a mixture comprising recombinant AAV viral particles and AAV capsid intermediates to fast performance liquid chromatography, wherein the AAV viral particles and AAV intermediates are bound to an anion exchange resin equilibrated at a pH of about 10.0 and subjected to a salt gradient while monitoring eluate for ultraviolet absorbance at about 260 and about 280, wherein the AAV full capsids are collected from a fraction which is eluted when the ratio of A260/A280 reaches an inflection point.

In one embodiment, the method further includes (a) mixing a suspension comprising recombinant AAV viral particles and AAV capsid intermediates and a Buffer A comprising 20 mM to 50 mM Bis-Tris propane (BTP) and a pH of about 10.0; (b) loading the suspension of (a) onto a strong anion exchange resin column; (c) washing the loaded anion exchange resin with Buffer 1% B which comprises a salt having the ionic strength of 10 mM to 40 mM NaCl and BTP with a pH of about 10.0; (d) applying an increasing salt concentration gradient to the loaded and washed anion exchange resin, wherein the salt gradient is the equivalent of about 10 mM to about 40 mM NaCl; and (e) collecting rAAV particles from elute obtained at a salt concentration equivalent to at least 70 mM NaCl, where the rAAV particles are at least about 90% purified from AAV intermediates. In one embodiment, this is determined by genome copies.

In one embodiment, the intermediates are eluted from the anion exchange resin when the salt concentration is the equivalent of greater than about 50 mM NaCl. In still a further embodiment, Buffer A is further admixed with NaCl to a final concentration of 1M in order to form or prepare Buffer B. In yet another embodiment, the salt gradient has an ionic strength equivalent to 10 mM to about 190 mM NaCl. The elution gradient may be from 1% buffer B to about 19% Buffer B. Optionally, the vessel containing the anion exchange resin is a monolith column and where Buffer A, Buffer B, and the salt gradient are in about 60 column volumes.

A stock or preparation of rAAV particles (packaged genomes) is "substantially free" of AAV empty capsids (and other intermediates) when the rAAV particles in the stock are at least about 75% to about 100%, at least about 80%, at least about 85%, at least about 90%, at least about 95%, or at least 99% of the rAAV in the stock and "empty capsids" are less than about 1%, less than about 5%, less than about 10%, less than about 15% of the rAAV in the stock or preparation.

In a further embodiment, the average yield of rAAV particles is at least about 70%. This may be calculated by determining titer (genome copies) in the mixture loaded onto the column and the amount presence in the final elutions. Further, these may be determined based on q-PCR analysis and/or SDS-PAGE techniques such as those described herein or those which have been described in the art.

For example, to calculate empty and full particle content, VP3 band volumes for a selected sample (e.g., an iodixanol gradient-purified preparation where # of GC=# of particles) are plotted against GC particles loaded. The resulting linear equation (y=mx+c) is used to calculate the number of particles in the band volumes of the test article peaks. The number of particles (pt) per 20 μL loaded is then multiplied by 50 to give particles (pt)/mL. Pt/mL divided by GC/mL gives the ratio of particles to genome copies (pt/GC). Pt/mL−GC/mL gives empty pt/mL. Empty pt/mL divided by pt/mL and ×100 gives the percentage of empty particles.

Generally, methods for assaying for empty capsids and AAV vector particles with packaged genomes have been known in the art. See, e.g., Grimm et al., *Gene Therapy* (1999) 6:1322-1330; Sommer et al., Molec. Ther. (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., J. Virol. (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacylamide gels (e.g., Novex). Silver staining may be performed using SilverXpress (Invitrogen, Calif.) according to the manufacturer's instructions. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied Biosystems Prism 7700 Sequence Detection System. Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is provided herein which utilizes a broad spectrum serine protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher. Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000 fold) and subjected to TaqMan analysis as described in the standard assay.

Additionally, or alternatively, droplet digital PCR (ddPCR) may be used. For example, methods for determining single-stranded and self-complementary AAV vector genome titers by ddPCR have been described. See, e.g., M. Lock et al, Flu Gene Therapy Methods, Hum Gene Ther Methods. 2014 Apr. 5 (2):115-25. doi: 10.1089/hgtb.2013.131. Epub 2014 Feb. 14.

5.1.3 Manufacturing

The rAAV.hFVIII vector can be manufactured as shown in the flow diagram shown in FIG. 13. Briefly, cells (e.g. HEK 293 cells) are propagated in a suitable cell culture system and transfected for vector generation. The rAAV.hFVIII vector can then be harvested, concentrated and purified to prepare bulk vector which is then filled and finished in a downstream process.

Methods for manufacturing the gene therapy vectors described herein include methods well known in the art such as generation of plasmid DNA used for production of the gene therapy vectors, generation of the vectors, and purification of the vectors. In some embodiments, the gene therapy vector is an AAV vector and the plasmids generated are an AAV cis-plasmid encoding the AAV genome and the gene of interest, an AAV trans-plasmid containing AAV rep and cap genes, and an adenovirus helper plasmid. The vector generation process can include method steps such as initiation of cell culture, passage of cells, seeding of cells, transfection of cells with the plasmid DNA, post-transfection medium exchange to serum free medium, and the harvest of vector-containing cells and culture media. The harvested vector-containing cells and culture media are referred to herein as crude cell harvest.

The crude cell harvest may thereafter be subject method steps such as concentration of the vector harvest, diafiltration of the vector harvest, microfluidization of the vector harvest, nuclease digestion of the vector harvest, filtration of microfluidized intermediate, purification by chromatography, purification by ultracentrifugation, buffer exchange by tangential flow filtration, and formulation and filtration to prepare bulk vector.

In one embodiment, the production plasmid is that shown in SEQ ID NO: 13. In one embodiment, the production plasmid is that shown in SEQ ID NO: 14. In one embodiment, the production plasmid is that shown in SEQ ID NO: 15. In another embodiment, the production plasmid is that shown in SEQ ID NO: 16.

In a specific embodiment, the methods used for manufacturing the gene therapy vectors are described in Section 8, infra.

5.2 Patient Population

Severe or moderate hemophilia A (HemA) patients are the chosen study population for several reasons. Severe hemophilia A patients are defined as having less than 1% of normal Factor VIII (FVIII) activity thus requiring frequent infusions of FVIII to control their bleeding diathesis. This represents a significant burden with respect to carrying on a normal life and in addition, the blood levels of FVIII go through the well-known peaks and troughs pattern, which is not optimal. The fact that FVIII blood levels in severe patients is less than 1% makes it possible to reliably measure even low to moderate increases in FVIII blood levels after rAAV.hVIII has been administered. Recent clinical trials have borne out the validity of this approach. Moderate HemA patients are defined as having 1% up to 5% of FVIII levels in blood.

Patients who are candidates for treatment are preferably adult males ≥18 years of age, diagnosed with moderate/severe or severe hemophilia A. In one embodiment, the patient has a baseline FVIII activity ≤2% of normal or documented history of FVIII activity ≤2%. In some embodiments, a patient <18 years of age can be treated. Candidates for treatment include subjects who have had at least 3 bleeding episodes per year that require on-demand treatment with FVIII. Other candidates for treatment include subjects who are treated with a prophylactic regimen of FVIII. Other criteria demonstrating that the subject is appropriate for treatment includes at least 100 days exposure history to FVIII; no documented history of inhibitors (neutralizing antibodies) to exogenous FVIII; no known allergic reaction to exogenous FVIII or any component of the rAAV.FVIII vector composition.

Prior to treatment, the hemophilia A patient should be assessed for NAb to the AAV serotype used to deliver the hFVIII gene (e.g, AAVhu.37 or AAVrh.10). Such NAbs can interfere with transduction efficiency and reduce therapeutic efficacy. Hemophilia A patients that have a baseline serum NAb titer <1:5 are good candidates for treatment with the rAAV.hFVIII gene therapy protocol.

Subjects may be permitted to continue their standard of care treatment(s) (e.g., recombinant FVIII therapy) prior to and concurrently with the gene therapy treatment at the discretion of their caring physician. In the alternative, the physician may prefer to stop standard of care therapies prior to administering the gene therapy treatment and, optionally, resume standard of care treatments as a co-therapy after administration of the gene therapy.

Desirable endpoints of the gene therapy regimen are an increase in FVIII activity to 3% of normal from baseline up to 52 weeks after administration of the gene therapy treatment. In one embodiment, patients achieve desired circulating FVIII levels (e.g., 5% or greater) after treatment with rAAV.hFVIII, alone and/or combined with the use of adjunctive treatments. In another embodiment, patients achieve circulating FVIII levels of 10%, 15%, 20% or greater after treatment with rAAV.hFVIII, alone and/or combined with the use of adjunctive treatments. In another embodiment, patients achieve circulating FVIII levels of 25%, 30%, 35%, 40%, 45%, 50%, 55%, 60%, 65%, 70%, 75%, 80%, 85%, 95%, 95% or greater after treatment with rAAV.hFVIII, alone and/or combined with the use of adjunctive treatments.

Nevertheless, patients having one or more of the following characteristics may be excluded from treatment at the discretion of their caring physician:
1. History of significant liver disease (ie, portal hypertension).
2. Significant hepatic inflammation or cirrhosis.
3. Evidence of active hepatitis B virus (HBV) or hepatitis C virus (HCV) infection.
4. History of human immunodeficiency virus (HIV) infection AND any of the following: CD4+ cell count <350 cells/mm$^3$, change in antiretroviral therapy regimen within 6 months prior to Day 0, or plasma viral load >200 copies/ml, on 2 separate occasions, as measured by PCR.
5. Anti-AAVhu.37 (or anti-AAVrh10, as appropriate) neutralizing antibody titer >1:5 or ≥1:10.
6. Participation (current or previous) in another gene therapy study.
7. Participation in another investigational medicine study within 3 months before screening.

In other embodiments, a caring physician may determine that the presence of one or more of these physical characteristics (medical history) should not preclude treatment as provided herein.

5.3. Dosing & Route of Administration

In one embodiment, the rAAV.hFVIII vector is delivered as a single dose per patient. In another embodiment, the rAAV.hFVIII vector is delivered as multiple doses per patient. In a further embodiment, the rAAV.hFVIII vector is delivered as two doses per patient. In one embodiment, the subject is delivered the minimal effective dose (MED) (as determined by preclinical study described in the Examples herein). As used herein, MED refers to the rAAV.hFVIII dose required to achieve 5% of normal Factor VIII activity.

As is conventional, the vector titer is determined on the basis of the DNA content of the vector preparation. In one embodiment, quantitative PCR or optimized quantitative PCR as described in the Examples is used to determine the DNA content of the rAAV.hFVIII vector preparations. In one embodiment, digital droplet PCR as described in the Examples is used to determine the DNA content of the rAAV.hFVIII vector preparations. In one embodiment, the dosage is about $1\times10^{11}$ genome copies (GC)/kg body weight to about $1\times10^{13}$ GC/kg, inclusive of endpoints. In one embodiment, the dosage is $5\times10^{11}$ GC/kg. In another embodiment, the dosage is $5\times10^{12}$ GC/kg. In specific embodiments, the dose of rAAV.hFVIII administered to a patient is at least $5\times10^{11}$ GC/kg, $1\times10^{12}$ GC/kg, $1.5\times10^{12}$ GC/kg, $2.0\times10^{12}$ GC/kg, $2.5\times10^{12}$ GC/kg, $3.0\times10^{12}$ GC/kg, $3.5\times10^{12}$ GC/kg, $4.0\times10^{12}$ GC/kg, $4.5\times10^{12}$ GC/kg, $5.0\times10^{12}$ GC/kg, $5.5\times10^{12}$ GC/kg, $6.0\times10^{12}$ GC/kg, $6.5\times10^{12}$ GC/kg, $7.0\times10^{12}$ GC/kg, or $7.5\times10^{12}$ GC/kg. Also, the replication-defective virus compositions can be formulated in dosage units to contain an amount of replication-defective virus that is in the range of about $1.0\times10^9$ GC to about $1.0\times10^{15}$ GC. As used herein, the term "dosage" can refer to the total dosage delivered to the subject in the course of treatment, or the amount delivered in a single (of multiple) administration.

In another embodiment, the composition is readministered at a later date. Optionally, more than one readministration is permitted. Such readministration may be with the same type of vector or a different viral vector as described herein. In one embodiment, the vector is readministered about 6 months after the first administration. In another embodiment, the vector is readministered about 1 year after the first administration. In another embodiment, the vector is readministered about 2 years after the first administration. In another embodiment, the vector is readministered about 3 years after the first administration. In another embodiment, the vector is readministered about 4 years after the first administration. In another embodiment, the vector is readministered about 5 years after the first administration. In another embodiment, the vector is readministered about 6 years after the first administration. In another embodiment, the vector is readministered about 7 years after the first administration. In another embodiment, the vector is readministered about 8 years after the first administration. In another embodiment, the vector is readministered about 9 years after the first administration. In another embodiment, the vector is readministered about 10 years or more after the first administration.

In one embodiment, the dosage is sufficient to increase the Factor VIII levels in the patient to 1% of normal. In one embodiment, the dosage is sufficient to increase the Factor VIII levels in the patient to 2% of normal. In one embodiment, the dosage is sufficient to increase the Factor VIII levels in the patient to 3% of normal. In another embodiment, the dosage is sufficient to increase the Factor VIII levels in the patient to 4% of normal. In another embodiment, the dosage is sufficient to increase the Factor VIII levels in the patient to 5% of normal. In another embodiment, the dosage is sufficient to increase the Factor VIII levels in the patient to 6, 7, 8, 9, 10, 11, 12, 13, 14, 15, 16, 17, 18, 19, 20, 25, 30, 35, 40, 45, 50, 55, 60, 65, 70, 75, 80, 85, 90, 95% or greater of normal.

In some embodiments, rAAV.hFVIII is administered in combination with one or more therapies for the treatment of hemophilia A, such as administration of recombinant FVIII.

5.4. Measuring Clinical Objectives

Measurements of efficacy of treatment can be measured by transgene expression and activity as determined by plasma Factor VIII levels and Factor VIII activity. Further assessment of efficacy can be determined by clinical assessment of replacement Factor VIII requirements and frequency of spontaneous bleeding episodes. Such assessments may be conducted twice a week for 4 weeks after the administration of the product, weekly from week 6 to week 12, monthly throughout the remainder of the first year and at 6 month intervals for a total period of 5 years.

Safety of the gene therapy vector after administration can be assessed by the number of adverse events, changes noted on physical examination, and/or clinical laboratory parameters assessed at multiple time points up to about 52 weeks post vector administration. Although physiological effect may be observed earlier, e.g., in about one week, in one embodiment, steady state levels expression levels are reached by about 12 weeks. The following assessments may be conducted twice a week for 4 weeks after the administration of the product, weekly from week 6 to week 12, monthly throughout the remainder of the first year and at 6 month intervals for a total period of 5 years. Such assessments include:

a. Physical examination
b. ECG
c. Biochemical assessment: Serum electrolytes, BUN, creatinine, calcium, phosphate, total protein, albumin, LDH, CPK, AST, ALT, alkaline phosphatase, bilirubin
d. Hematological assessment: CBC and differential, coagulation profile
e. Urinalysis
f. Immunological assessment:
g. Serological response to hu.37 capsid (or rh.10 capsid, as appropriate) and to Factor VIII
h. T cell response to hu.37 capsid (or rh.10 capsid, as appropriate) and Factor VIII antigens
i. Assessment of vector DNA; qPCR measurements in plasma, urine and saliva. hFVIII increase achieved with rAAV.hFVIII administration can be assessed as a defined percent change in hFVIII at about 12 weeks, or at other desired timepoints, compared to hFVIII levels of a patient not having hemophilia A, i.e., so-called normal hFVIII levels of about 100%. In another embodiment, the change is compared to the patient's baseline hFVIII levels. In one embodiment, the desired efficacy is an increase in the Factor VIII levels in the patient to 3% of normal. In one embodiment, the desired efficacy is an increase in the Factor VIII levels in the patient to 4% of normal. In one embodiment, the desired efficacy is an increase in the Factor VIII levels in the patient to 5% of normal. In one embodiment, the desired efficacy is an increase in the Factor VIII levels in the patient to 6% of normal. In one embodiment, the desired efficacy is an increase in the Factor VIII levels in the patient to 7% of normal. In one embodiment, the desired efficacy is an increase in the Factor VIII levels in the patient to 8% of normal. In one embodiment, the desired efficacy is an increase in the Factor VIII levels in the patient to 9% of normal. In another embodiment, the dosage is sufficient to increase the Factor VIII levels in the patient to 10% of normal. In another embodiment, the dosage is sufficient to increase the Factor VIII levels in the patient to 15% of normal. In another embodiment, the dosage is sufficient to increase the Factor VIII levels in the patient to 20% or greater of normal. In one embodiment, coagulation panels are performed as a part of standard testing to infer FVIII activity.

As used herein, the rAAV.hFVIII vector herein "functionally replaces" or "functionally supplements" the patients defective FVIII with active FVIII when the patient expresses a sufficient level of FVIII to achieve at least one of these clinical endpoints. Expression levels of hFVIII which achieve as low as about 1% to less than 100% of normal wild-type clinical endpoint levels in a non-hemophilia patient may provide functional replacement.

In one embodiment, expression may be observed as early as about 8 hours to about 24 hours post-dosing. One or more of the desired clinical effects described above may be observed within several days to several weeks post-dosing.

Long term (up to 260 weeks) safety and efficacy can be assessed after rAAV.hFVIII administration.

In one aspect, a regimen for delivery of a hFVIII gene product to a human patient is provided. The regimen comprises (a) delivery of a first rAAV.hFVIII vector comprising an expression cassette as described herein; and (b) delivery of a second rAAV.hFVIII vector comprising an expression cassette as described herein, wherein the first recombinant AAV vector or the second AAV vector has an AAV3B capsid. The sequence of AAV3B is shown in SEQ ID NO: 20 and Accession No. AAB95452.1. In one embodiment, the other of the first or the second AAV vector has an rh.10 capsid. In another embodiment, the other of the first or the second AAV vector has an AAVhu.37 capsid. Such regimens are described in International Patent Application No. PCT/US16/42472, which is incorporated herein by reference.

The viral vectors described herein may be used in preparing a medicament for delivering hFVIII to a subject (e.g., a human patient) in need thereof, supplying functional hFVIII to a subject, and/or for treating hemophilia A disease.

In another aspect, an rAAV.hFIII vector as described herein is provided for use in treating hemophilia A. In one embodiment, multiple doses are provided for use in treating hemophilia A. In another aspect, an rAAV.hFIII vector as described herein is provided for the manufacture of a medicament for treating hemophilia A.

In one embodiment, a second administration of a rAAV.hFVIII vector is given. In one embodiment, the rAAV.hFVIII vector of the second administration has the same AAV capsid as provided with the first dosage. In one embodiment, the rAAV.hFVIII vector of the second administration has an AAVrh.10 capsid. In another embodiment, the rAAV.hFVIII vector of the second administration has a different AAV capsid as the vector of the first dose. In one embodiment, the rAAV.hFVIII vector of the second administration has a tropism for liver. In one embodiment, the rAAV.hFVIII vector of the second administration has an AAV3B capsid.

In a further aspect, the invention involves targeting hepatocytes of the patient.

In one aspect, the delivery of the first rAAV and the second rAAV are temporally separated by at least about one month, at least about three months, or about 1 year to about 10 years.

The following examples are illustrative only and are not intended to limit the present invention.

EXAMPLES

6. EXAMPLE 1: PRECLINICAL TESTING

6.1 hFVIII Vector

Unlike human factor FIX (hFIX), the cDNA for hFVIII is much larger and adjustments need to be made to fit this transgene into the standard AAV genome. As the B Domain Deleted (BDD) hFVIII transgene is 1457 amino acids and with the inclusion of other necessary elements for transcription, an AAV vector is still at the limit of its packing capacity. Therefore, steps have been taken to reduce the size of the other elements, including the transgene expression control elements.

In order to restrict expression of hFVIII to the liver while keeping the size of the elements as small as possible several strong liver-specific promoters were shortened and combined, with combinations of up to three liver-specific enhancer sequences, to generate 42 enhancer/promoter combinations. hFVIII activity and immunogenicity of the transgene were evaluated in FVIII KO mice following administration of AAV vectors.

6.1.1 AAV Vector Production for Pre-Clinical Testing 42 plasmids were generated containing one of the enhancer/promoter combinations. 14 enhancer combinations were generated using three enhancer sequences; En34 (34 bp core enhancer from the human apolipoprotein hepatic control region), ABPS (shortened version of the 100 bp distal enhancer from the α1-microglogulin/bikunin precursor [ABP] to 42 bp), and EnTTR (100 bp enhancer sequence from transthyretin). The number of enhancer combinations was restricted due to the total ITR-ITR size and by combination of the enhancers in the following sequence: 5'-EnTTR-ABPS-En34-Promoter-3'. Table 1. Each of the 14 enhancer combinations were inserted upstream of one of three promoters; TBG-S1 (P1, shortened version of the liver-specific thyroxine binding globulin or TBG promoter), A1AT (P2, modified SERINA1 [α1-antitrypsin] promoter), and TTR (P3, transthyretin promoter). The resulting constructs were designed to express a codon-optimized version of the human factor VIII protein where the B domain is deleted and replaced by a short 14 amino acid linker, hFVIIIco-SQ (SEQ ID NO: 2).

All AAV vectors were produced as described in Gao G, Lu Y, Calcedo R, et al. Biology of AAV serotype vectors in liver-directed gene transfer to nonhuman primates. *Mol Ther.* 2006; 13(1):77-87, which is incorporated herein by reference. Briefly, plasmids expressing hFVIII from one of the 42 enhancer/promoter combinations were packaged with the AAVrh10 viral capsid. Plasmids expressing hFVIII from E06.TTR were also packaged in AAV8, AAV9, AAVhu37, and AAVrh64R1 viral capsids.

6.1.2 SDS-PAGE Analysis of Vectors

The AAVrh10 enhancer/promoter combination vector lots used in the study were subjected to purity assessment by sodium dodecyl sulfate-polyacrylamide gel electrophoresis (SDS-PAGE) as described in Lock M, Alvira M, Vandenberghe L H, et al. Rapid, simple, and versatile manufacturing of recombinant adeno-associated viral vectors at scale. *Hum Gene Ther.* 2010; 21(10):1259-1271, which is incorporated herein by reference. Briefly, denatured and reduced vector samples containing $5 \times 10^9$ GC were loaded for SDS-PAGE. Proteins were stained by SYPRO ruby stain (Invitrogen, Carlsbad, Calif., USA) following fixation, visualized, and then quantified using Syngene imaging analysis system and GeneTool software (Syngene, Frederick, Md.). The percent purity of the capsid (VP1, VP2, and VP3 proteins indicated over total protein) was calculated. The percentage purity of the 42 vectors ranged from 29% (AAVrh10.E12.P3) to 100%, with a mean purity of 90% (data not shown).

6.1.3 Mice

Breeding pairs of FVIII KO mice were obtained from The Jackson Laboratory (Bar Harbor, Me., USA) and a colony was maintained at the University of Pennsylvania's Translational Research Laboratories housed under specific pathogen-free conditions. All animal procedures and protocols were approved by the Institutional Animal Care and Use Committee (IACUC) of the University of Pennsylvania. Male FVIII KO at 6-12 weeks of age were injected IV with $10^{10}$ GC of vector per mouse into the tail vein. Vector was diluted in phosphate buffered saline (PBS) and 100 µl of the vector dilution was injected. Plasma was collected biweekly by retro-orbital bleeds into sodium citrate collection tubes.

6.1.4 Determination of hFVIII Activity hFVIII activity was measured in plasma by COATEST SP4 kit according to the manufacturer's protocol (DiaPharma, Ohio, USA). At week 2 post-injection, mice showed a vast range in hFVIII activity from 0.12-2.12 IU/ml (FIG. 5).

Five constructs demonstrated significantly increased activity levels over the others; E03.TTR, E05.A1AT, E05.TTR, E06.TTR, and E12.A1AT (FIG. 5A). The variation in hFVIII activity levels seen at week 2 was prior to the generation of antibodies to the transgene (FIG. 5B). Therefore, there were construct-dependent significant differences in activity levels.

6.1.5 Detection of Anti-hFVIII IgG in Mouse Plasma

IgG antibodies against hFVIII in mouse plasma were measured by ELISA, where all reagents were from Sigma-Aldrich (St. Louis, Mo., USA) unless otherwise stated. ELISA plates were coated with 1 µg/ml BDD-hFVIII-SQ (Xyntha, Wyeth Pharmaceuticals Inc., Dallas, Tex., USA) in 0.1 M carbonate buffer (pH 9.6) and incubated overnight at 4° C. Wells were washed five times with 0.05% Tween 20 in PBS and blocked with 5% non-fat milk (Bio Rad, Hercules, Calif., USA) in PBS for one hour at room temperature. Following removal of the blocking buffer, plasma samples diluted in 5% non-fat milk were added to the plates and incubated for one hour at room temperature. Plasma samples from naïve mice were used as the control. Plates were then washed five times and HRP-conjugated anti-mouse IgG was added at a 1:1000 dilution in non-fat milk. Following incubation at room temperature for 90 minutes, plates were washed eight times and 3,3',5,5'-tetramethylbenzidine (TMB) was added for detection. The reaction was stopped after 5 minutes at room temperature using 2N sulfuric acid and plates were read at 450 nm using a BioTek µQuant plate reader (Winooski, Vt., USA).

FVIII KO mice showed antibody generation to hFVIII at week 4 post-vector administration and by week 8 mice in most of the 42 vector groups had detectable anti-hFVIII IgG levels with a corresponding decrease in hFVIII activity levels (FIG. 6). Time courses of hFVIII activity and antibody generation quantified by titer are presented in FIGS. 7 and 8, respectively. More than 50% of mice injected with constructs E05.A1AT, E10.A1AT, and all promoters with the E06 enhancer combination had antibodies to the transgene by week 8. However, antibodies to the transgene were not seen in all groups. For 6 out of the 42 vector groups (E11.TTR, E13.TBG-S1, E13.A1AT, and all constructs using E01), no hFVIII antibodies were detected at week 8 (FIG. 6) and two groups had no detectable antibodies throughout the duration of the 12 week study (E01.A1AT and E11.TTR). Time to event analysis for the generation of antibodies to hFVIII was also performed. Mice injected with vectors using E01.A1AT, E11.TTR, E01.TBG-S1, E11.A1AT, and E13.TBG-S1 for expression had the longest time to antibody expression, whereas constructs containing E06.TTR, E06.A1AT, E05.A1AT, E09.TBG-S1, and E14.TTR had the shortest time to antibody expression.

6.1.6 Statistical Analysis

To identify similar treatment groups according to hFVIII activity in plasma at week 2, the data were analyzed using a single fixed factor ANOVA model with Tukey post hoc tests to identify group mean activity levels that differ from one another. Time to event analysis was performed for the generation of antibodies against hFVIII.

6.1.9 Comparison of Activity and Immunogenicity by a Variety of AAV Capsids

Next the differences in activity levels were determined and potential contribution to immunogenicity by the AAV capsid used was ascertained. For this study the most immunogenic genome from the previous studies was selected—E06.TTR. Interestingly, this construct produced significantly higher expression than the majority of the other constructs at week 2 but in the following weeks antibodies were generated against the hFVIII transgene in 80% of injected mice.

The same vector genome using the E06 enhancer combination with the liver-specific TTR promoter was packaged with one of five AAV capsids; AAVrh10, AAV8, AAV9, AAVhu37 and AAVrh64R1. Again, FVIII KO mice were injected IV at a dose of $10^{10}$ GC per mouse and plasma hFVIII activity levels and anti-hFVIII IgG titers were followed throughout a 12 week study. Stark differences in expression and immunogenicity of the transgene were seen based on the AAV vector used for gene transfer (FIG. 9). At week 2 post-vector administration, hFVIII activity in plasma varied from 0.51 IU/ml following AAVrh64R1 administration to 1.26 IU/ml with AAVrh10 (FIG. 9A). During the course of the study, several of the mice generated anti-hFVIII antibodies ranging from 20% of mice administered with AAV8 or AAV9 vectors to 63% of mice that received AAVrh10 (FIG. 9B). Therefore, even with a highly immunogenic enhancer and promoter combination, the immune response to the transgene can vary based on the AAV capsid used for gene transfer.

6.1.10 Discussion

Previous studies in FVIII KO mice where the HLP promoter was used for expression did not detect antibodies to the transgene throughout the duration of the study. The HLP promoter sequence is similar to that of the E01.A1AT enhancer/promoter combination, where mice administered with this AAVrh10 vector had no detectable antibodies throughout the duration of the 12 week study. Unfortunately, activity from this vector in FVIII KO mice was relatively low with only 0.189 IU/ml detectable in plasma at week 2 post-vector administration and a peak level of 0.303 IU/ml at week 6.

Interestingly, the AAV capsid used for gene transfer of the same transgene cassette significantly influenced both immunogenicity to hFVIIII and peak hFVIII activity. In order to study the effect of capsid on generation of anti-hFVIII antibodies, the most immunogenic transgene cassette was used (E06.TTR). The five vector capsids studied could be divided into two groups; those were ≤20% of mice generated anti-hFVIII antibodies (AAV8 and AAV9) and those where >20% of mice developed a humoral immune response (AAVrh10, AAVhu37, and AAVrh64R1). The tolerance towards the hFVIII transgene associated with the AAV8 capsid is perhaps unsurprising due to previous studies that demonstrate that IV delivery of this capsid may activate transgene-specific regulatory T cells in the context of the tolerogenic nature of the liver. In addition, we have previously shown that there were no detectable FIX inhibitors following IM injection of AAV8 in hemophilia B mice. Therefore, even with a highly immunogenic enhancer and promoter combination, the immune response to the transgene can vary based on the AAV capsid used for gene transfer.

hFVIII activity levels in plasma following administration of the five different AAV capsids also varied significantly from 0.51 IU/ml with AAVrh64R1 to 1.26 IU/ml with AAVrh10 at week 2 post-vector administration. Expression from the AAVrh10 vector was significantly elevated compared to AAV8 and coincided with the generation of anti-hFVIII antibodies in 63% of mice. This capsid comparison study was performed using a highly immunogenic transgene cassette and likely does not model that seen in humans where ~30% of hemophilia A patients generate antibodies to the recombinant protein. Therefore, the higher expression levels produced following administration of the AAVrh10 vector may be more beneficial to the clinical situation where a lower dose of vector would be required for significant improvements in the incidence of bleeding events and supplementation with the recombinant hFVIII protein.

Figure 1:
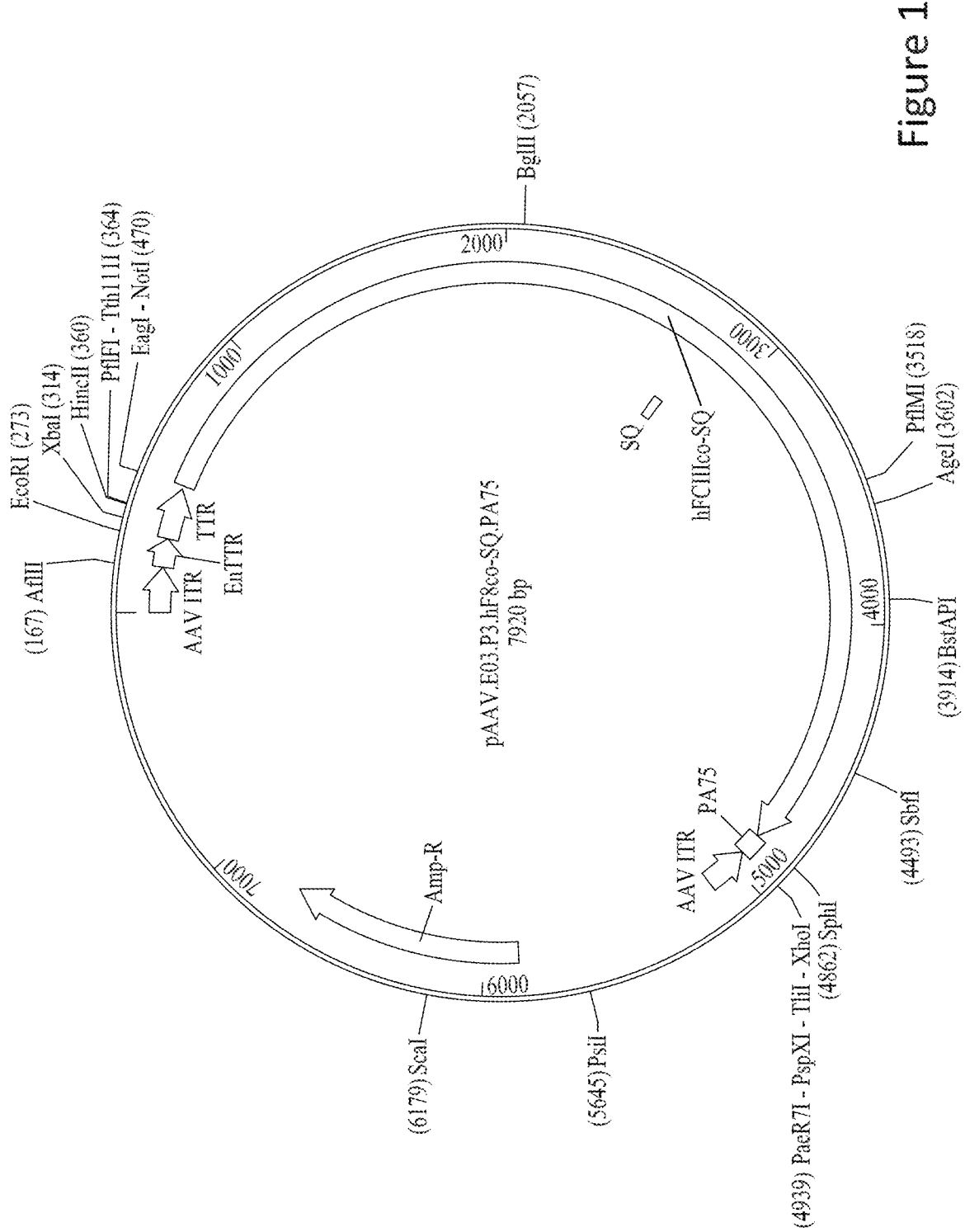
FIG. 1 is a schematic representation of pAAV.E03.P3.hF8co-SQ.PA75 cis plasmid.

From the results of this study, the E03.TTR (FIG. 1; SEQ ID NO: 13), E03.A1AT (FIG. 3; SEQ ID NO: 15), E12.TTR (FIG. 2; SEQ ID NO: 14) and E12.A1AT (FIG. 4; SEQ ID NO: 16) constructs were selected for further testing.

6.2 Dosage Studies 6.2.1 Studies in FVIII KO Mice to Inform on the Approximate MED FVIII KO mice in C57BL/6 and 129 background receive a tail vein injection of one of four vector doses of AAVhu37.E03.TTR.hFVIIIco-SQ.PA75. Such vector doses are $5 \times 10^{10}$ GC/kg, $5 \times 10^{11}$ GC/kg, $5 \times 10^{12}$ GC/kg, and $5 \times 10^{13}$ GC/kg. A cohort of animals receiving control article only (vehicle buffer) is included as a vehicle control. After vector administration, the animals are monitored daily for general observations. Blood is collected from the animals at the appropriate time points to capture the hFVIII activity levels. Animals in subset A are sacrificed on day 60 after dosing, animals in subset B are sacrificed on day 28 after dosing, and animals in subset C are sacrificed on day 3 after dosing. Blood is also collected at necropsy for a serum chemistry panel and hematology. Sacrificed animals will be necropsied; the organs, such as right Inguinal lymph node, right testis, pancreas, duodenum, colon, brain, right gastrocnemius muscle, stomach, right kidney, right lung, spleen, heart, liver and gross lesions if any, are harvested for biodistribution and histopathology examinations. Total cellular DNA and RNA are extracted for mice that received the highest dose of vector and those that received the control article. qPCR and RT-qPCR assays are performed on the extracted DNA/RNA to measure vector genome copies and transcript levels in the organs, respectively. The efficacy of the test article is determined by the hFVIII protein activity levels in plasma by COATEST assay. Also, anti-hFVIII antibodies re monitored by anti-hFVIII IgG ELISA assay and the extrinsic pathway of coagulation is evaluated by prothrombin time (PT) assay.

6.3 Studies in Non-Human Primates 6.3.1 Expression Studies in NHP

The primary objective of this non-GLP study is to evaluate the potential vector related toxicity and biodistribution in NHP.

Male rhesus and cynomolgus macaques were used for this study. Only male animals were used in the study since hemophilia A is an X-linked genetic disorder. All macaques had NAb titers of <1:5 at the start of the studies determined as described previously (CALCEDO et al. (2009) Worldwide epidemiology of neutralizing antibodies to adeno-associated viruses. J Infect Dis, 199, 381-90). Prior to vector administration, macaques were anesthetized with a mixture of ketamine (10-15 mg/kg) and dexmedetomidine (0.05-0.10 mg/kg) injected IM. Macaques were administered with vectors IV via the saphenous vein. Blood samples were taken prior to the initiation of the study and biweekly during the study via venipuncture of the femoral vein. All clinical pathology tests on blood samples were conducted by Antech Diagnostics (Irvine, Calif.), including complete blood counts and differentials, complete clinical chemistries, and coagulation panels.

Pilot studies for expression of hFVIII in NHPs were performed. Two rhesus macaques and two cynomolgus macaques were administered IV with $3 \times 10^{12}$ GC/kg of AAVrh10 (FIG. 10A) and AAVhu37 (FIG. 10B) vectors expressing hFVIII from the ABP2.TGB-S1 enhancer/promoter combination, respectively. High peak expression was seen in all animals but by weeks 6-8. A humoral immune response to hFVIII in macaques injected with AAVrh10 was seen. The development of anti-hFVIII antibodies was delayed in one animal that received AAVhu37, occurring at 12 week post-vector administration, and did not develop throughout the course of the study for the other animal. The macaque which received AAVhu37.TBG-S1.hFVIII-SQ.PA7 was followed for 35 months post-injection (FIGS. 22 to 24).

Based on the FVIII KO mouse studies and this small pilot rhesus macaque study, two of the original 42 enhancer/promoter combinations were selected for further evaluation in cynomolgus macaques, using two different Clade E capsids for expression.

6.3.2 Further Studies in NHP

Subsequently 20 male cynomolgus macaques were dosed with one of four vectors; AAVrh10.E03.TTR.hFVIIIco-SQ.PA75, AAVrh10.E12.A1AT.hFVIIIco-SQ.PA75, AAVhu37.E03.TTR.hFVIIIco-SQ.PA75, and AAVhu37.E12.A1AT.hFVIIIco-SQ.PA75 (n=5 macaques per vector). Vector was IV administered at a dose of $1.2 \times 10^{13}$ GC/kg (based on middle oqPCR titer). With one capsid plus enhancer/promoter combination, peak expression of 37% of normal FVIII levels was seen at week 2 post-vector administration, which then plateaued at 20% of normal (FIG. 11). While antibodies to the hFVIII were detected in the majority of macaques by week 8, antibodies remained undetectable in two animals at week 30 post-vector administration (FIG. 12). Methods discussed below. By using time to event analysis for the generation of antibodies, it was determined that there was a significant difference between AAVrh10 and AAVhu37 (FIG. 14).

6.3.3 Determination of hFVIII Expression in NHP Plasma hFVIII expression was measured by ELISA, where all reagents were from Sigma-Aldrich (St. Louis, Mo., USA) unless otherwise stated. ELISA plates were coated with anti-hFVIII IgG (Green Mountain Antibodies, Vt., USA) at a 1:500 dilution in 0.1 M carbonate buffer (pH 9.6) and incubated overnight at 4° C. Wells were washed four times with 0.1% Tween 20 in PBS and blocked with 5% non-fat milk (Bio Rad, Hercules, Calif., USA) in PBS for one hour at room temperature. Following removal of the blocking buffer, plasma samples diluted in 5% non-fat milk were added to the plates and incubated for one hour at room temperature. Plates were then washed four times and anti-hFVIII IgG (ThermoFisher Scientific, Mass., USA) was added at a 1:1000 dilution in non-fat milk. Following incubation for one hour at room temperature plates were washed four times and HRP-conjugated anti-sheep IgG was added at a 1:1000 dilution in non-fat milk. Following incubation at room temperature for 90 minutes, plates were washed five times and 3,3',5,5'-tetramethylbenzidine (TMB) was added for detection. The reaction was stopped after 5 minutes at room temperature using 2N sulfuric acid and plates were read at 450 nm using a BioTek µQuant plate reader (Winooski, Vt., USA). FIG. 11.

Results of long-term stable expression of human FVIII in a cynomolgus macaque (35 months) following a single intravenous injection of AAVhu37.TBG-S1.hFVIII-SQ.PA75 are shown in FIG. 22. Results show stable expression until necropsy at 35 months. Results of liver enzyme testing are shown in FIG. 23 Results show that liver enzyme levels where within the normal range, except for transient elevation after liver biopsy. Neutralizing antibody (Nab) response to the AAVhu.37 capsid is shown in FIG. 24.

Single cell technology was used to detect AAV vector DNA and RNA in the hepatocytes of NHP M11269, discussed above, who received intravenous administration of of AAVhu37.TBG-S1.hFVIII-SQ.PA75 at 3E12 GC/kg. Single cell hepatocytes were evaluated for presence of AAV genomes and expression. 150 weeks post vector, hepatocytes were isolated from a liver wedge by perfusing with a mixture of collagenase/protease. Single cells were sorted into individual wells of a 96 well plate. Cells from one 96 well plate were whole genome amplified (WGA) and AAV genomes in cells quantified by digital PCR using a probe against human FVIII. A second 96 well plate was whole-transcriptome amplified (WTA) for evaluating FVIII expression.

Results shown below in Table 3. AAV genomes could be detected in ~25% of the single cells evaluated. RNA expression was only detected in ~4% or 20% of the cells that take up DNA. RNA expressing cells could be stratified into two types as low and high. It is unclear why a substantial number of cells take up vector but fail to express the transgene. These results were corroborated by in situ hybridization studies performed by CMC core (data not shown).

TABLE 3

Percent DNA and RNA Positive Single Cells

| | Sample | Positives/total | Percent positive |
|---|---|---|---|
| Single cell (w152) | DNA | 23/96 | 24% |
| | RNA | 4/96 | 4% |
| | RNA/DNA positive cells | 4/23 | 17% |

| | Sample | w42 biopsy | w152 necropsy |
|---|---|---|---|
| liver homogenate | DNA (GC/cell) | 10 | 7.6 +/− 1.1 |
| | hFVIII RNA (copies ug RNA) | 4.4 +/− 1.1 E4 | 6.4 +/− 0.7E4 |

6.3.4 Detection of Anti-hFVIII IgG in NHP Plasma

IgG antibodies against hFVIII in NHP plasma were measured by ELISA as described previously, with the exception that HRP-conjugated anti-NHP IgG was added at a 1:2000 dilution in non-fat milk for detection (FIG. 12).

6.3.5 Detection of Bethesda Titer in NHP Plasma

Inhibitory antibody against human FVIII was measured by Nijmegen modified Bethesday assay (Giles et al., 1998). One Bethesda unit represents inhibition of coagulation activity of normal human plasma by 50%.

6.3.6 Liver Biopsies

Two NHPs from each group received a liver biopsy at week 5 post-vector administration performed by mini-laparotomy. Selection of animals was based on hFVIII expression in plasma at week 4. The first animal selected was the animal with the median hFVIII level, the second animal selected was the animal with hFVIII level closest or second closest (if the closest one is the median one) to the mean level. Samples of liver tissue were taken for histopathology, vector biodistribution, and transgene mRNA analysis. On day 3 post-liver biopsy, blood was taken for complete blood counts and differentials, complete clinical chemistries, and coagulation panels.

6.3.7 Immunosuppression Protocol

An immunosuppression regimen was initiated as required in animals where the ability to detect hFVIII expression was lost in the presence of detectable antibodies to hFVIII (Bethesda unit >1) following vector administration. The immunosuppression regimen was performed with rituximab (250 mg/m$^2$, IV at 4 weekly intervals, total of 4 infusions) and cyclophosphamide (300 mg/m$^2$, slow intravenous infusions every 15 days, total of 8 doses over 4 months) as described previously (Mcintosh et al. (2013) Therapeutic levels of FVIII following a single peripheral vein administration of rAAV vector encoding a novel human factor VIII variant. Blood, 121, 3335-44.).

6.3.8 Vector Biodistribution

Tissue samples (inguinal lymph nodes, lumbar lymph nodes, muscle [right gastrocnemius], right testis, pancreas, right kidney, spleen, right lung, heart, and liver) from C57BL/6J mice were snap frozen at the time of necropsy, and DNA was extracted using the QIAamp DNA Mini Kit (Qiagen, Valencia, Calif., USA). Detection and quantification of vector genomes copies (GC) in extracted DNA and relative hFVIII transcript expression in extracted RNA were performed by real-time PCR as described previously. Briefly, vector GCs and RNA were quantified using primers/probe designed against the hFVIII transgene sequence of the vector. Quantification of GC from liver was performed on one liver sample from each mouse (n=3/group). RNA relative transcript expression was determined using the AACT of each sample normalized to 18S expression.

The vector biodistribution was evaluated for a subset of 18 of the AAVrh10 enhancer/promoter vectors. AAVrh10 vectors expressing hFVIIIco IV were administered at a dose of $10^{11}$ GC per mouse into 6 to 8 week old C57BL/6J wild type mice. Mice were necropsied at day 14 post-vector administration and muscle (right gastrocnemius), right testis, pancreas, right kidney, spleen, right lung, heart, and liver was collected. DNA and RNA were extracted and vector GCs and RNA transcript levels, respectively, were quantified using primers/probe designed against the hFVIII transgene sequence of the vector. There were no significant differences in liver vector GC (FIG. 20A) or RNA transcript levels (FIG. 20B) across the vector administered groups, and there were no detectable GC or RNA in the control (PBS) administered groups. However, there was a trend towards higher RNA transcript levels in the liver for vectors that used the A1AT promoter for expression, regardless of the enhancer sequences (FIG. 20B). For the other tissues collected, hFVIII RNA transcript levels were on average 1000-fold lower than in the liver but high extrahepatic expression was seen in muscle and heart in the C57BL/6J mice following administration of E01.TBG-S1, E02.A1AT, E09.A1AT, and E09.TTR (FIG. 21).

6.4. Testing of Vector

Characterization assays including serotype identity, empty particle content and transgene product identity are performed. Descriptions of all the assays appear below.

6.4.1 Genomic Copy (GC) Titer

An optimized quantitative PCR (oqPCR) assay is used to determine genomic copy titer by comparison with a cognate plasmid standard. The oqPCR assay utilizes sequential digestion with DNase I and Proteinase K, followed by qPCR analysis to measure encapsidated vector genomic copies. DNA detection is accomplished using sequence specific primers targeting the PA75 polyA region in combination with a fluorescently tagged probe hybridizing to this same region. Comparison to the plasmid DNA standard curve allows titer determination without the need of any post-PCR sample manipulation. A number of standards, validation samples and controls (for background and DNA contamination) have been introduced into the assay. This assay has been qualified by establishing and defining assay parameters including sensitivity, limit of detection, range of qualification and intra and inter assay precision. An internal AAVrh.10 reference lot was established and used to perform the qualification studies.

6.4.2 Vector Capsid Identity: AAV Capsid Mass Spectrometry of VP3

Confirmation of the AAV2/hu.37 or AAV2/rh.10 serotype of the vector is achieved by an assay based upon analysis of peptides of the VP3 capsid protein by mass spectrometry (MS). The method involves multi-enzyme digestion (trypsin, chymotrypsin and endoproteinase Glu-C) of the VP3 protein band excised from SDS-PAGE gels followed by characterization on a UPLC-MS/MS on a Q-Exactive Orbitrap mass spectrometer to sequence the capsid protein. A tandem mass spectrometry (MS) method was developed that allows for identification of certain contaminant proteins and deriving peptide sequence from mass spectra.

6.4.3 Empty to Full Particle Ratio

Vector particle profiles are using analytical ultracentrifugation (AUC) Sedimentation velocity as measured in an analytical ultracentrifuge is an excellent method for obtaining information about macromolecular structure heterogeneity, difference in confirmation and the state of association or aggregation. Sample was loaded into cells and sedimented at 12000 RPM in a Beckman Coulter Proteomelab XL-I analytical ultracentrifuge. Refractive index scans were recorded every two minutes for 3.3 hours. Data are analyzed by a c(s) model (Sedfit program) and calculated sedimentation coefficients plotted versus normalized c(s) values. A major peak representing the monomeric vector should be observed. The appearance of peaks migrating slower than the major monomeric peak indicate empty/misassembled particles. The sedimentation coefficient of the empty particle peak is established using empty AAV8 particle preparations. Direct quantitation of the major monomeric peak and preceding peaks allow for the determination of the empty to full particle ratio.

6.4.4 Infectious Titer

The infectious unit (IU) assay is used to determine the productive uptake and replication of vector in RC32 cells (rep2 expressing HeLa cells). Briefly, RC32 cell in 96 well plates are co-infected by serial dilutions of vector and a uniform dilution of Ad5 with 12 replicates at each dilution of rAAV. Seventy-two hours after infection the cells are lysed, and qPCR performed to detect rAAV vector amplification over input. An end-point dilution TCID50 calculation (Spearman-Karber) is performed to determine a replicative titer expressed as IU/ml. Since "infectivity" values are dependent on particles coming into contact with cells, receptor binding, internalization, transport to the nucleus and genome replication, they are influenced by assay geometry and the presence of appropriate receptors and post-binding pathways in the cell line used. Receptors and post-binding pathways critical for AAV vector import are usually maintained in immortalized cell lines and thus infectivity assay titers are not an absolute measure of the number of "infectious" particles present. However, the ratio of encapsidated GC to "infectious units" (described as GC/IU ratio) can be used as a measure of product consistency from lot to lot.

7. EXAMPLE 2: PROTOCOL FOR TREATING HUMAN SUBJECTS

This Example relates to a gene therapy treatment for patients with genetically confirmed X-linked hemophilia A due to mutations in the clotting factor 8 (FVIII) gene. In this example, the gene therapy vector, AAVhu.37.hFVIII, a replication deficient adeno-associated viral vector hu.37 (AAVhu.37) expressing hFVIII is administered to patients with hemophilia A. Efficacy of treatment can be assessed using FVIII levels as a surrogate for transgene expression. Primary efficacy assessments include FVIII levels at about 12 weeks post treatment, with persistence of effect followed thereafter for at least 1 year. Long term safety and persistence of transgene expression may be measured post-treatment in liver biopsy samples.

7.1. Gene Therapy Vector—AAV.hFVIII 7.1.1. AAVhu.37.hFVIII

The AAVhu.37.hFVIII vector consists of the AAV vector active ingredient and a formulation buffer. The external AAV vector component is a serotype hu.37, T=1 icosahedral capsid consisting of 60 copies of three AAV viral proteins, VP1, VP2, and VP3, at a predicted ratio of 1:1:10. The capsid contains a single-stranded DNA recombinant AAV (rAAV) vector genome (FIG. 1-FIG. 4).

The genome contains a human factor VIII (FVIII) transgene flanked by the two AAV inverted terminal repeats (ITRs). An enhancer, promoter, human factor VIII (hFVIII) coding sequence, and polyadenylation (polyA) signal comprise a B domain deleted, codon optimized human FVIII transgene. The ITRs are the genetic elements responsible for the replication and packaging of the genome during vector production and are the only viral cis elements required to generate rAAV. In one embodiment, expression of the human FVIII coding sequence is driven from the transthyretin promoter (SEQ ID NO: 7). In another embodiment, expression of the human FVIII coding sequence is driven from the modified A1AT promoter (SEQ ID NO: 9). The construct includes at least one enhancer element to stimulate promoter activity. In one embodiment, an enTTR enhancer (SEQ ID NO: 5) is included. In another embodiment, two copies of the ABP-S enhancer (SEQ ID NO: 6) proceed one copy of the enTTR enhancer (SEQ ID NO: 5). A synthetic polyA signal of about 75 nt (SEQ ID NO: 10) is included to mediate termination of human FVIII mRNA transcripts.

The vector is supplied as a suspension of AAVhu.37.hFVIII vector in formulation buffer. In one embodiment, the formulation buffer is 0.001% Pluronic F-68 in TMN200 (200 mM sodium chloride, 1 mM magnesium chloride, 20 mM Tris, pH 8.0).

Details of the vector manufacturing and characterization of the vectors, are described in the sections below.

7.1.2. AAVrh.10.hFVIII

The AAVrh.10.hFVIII vector consists of the AAV vector active ingredient and a formulation buffer. The external AAV vector component is a serotype rh.10, T=1 icosahedral capsid consisting of 60 copies of three AAV viral proteins, VP1, VP2, and VP3, at a predicted ratio of 1:1:10. The capsid contains a single-stranded DNA recombinant AAV (rAAV) vector genome (FIG. 1-FIG. 4).

The genome contains a human factor VIII (FVIII) transgene flanked by the two AAV inverted terminal repeats (ITRs). An enhancer, promoter, human factor VIII (hFVIII) coding sequence, and polyadenylation (polyA) signal comprise a B domain deleted, codon optimized human FVIII transgene. The ITRs are the genetic elements responsible for the replication and packaging of the genome during vector production and are the only viral cis elements required to generate rAAV. In one embodiment, expression of the human FVIII coding sequence is driven from the transthyretin promoter (SEQ ID NO: 7). In another embodiment, expression of the human FVIII coding sequence is driven from the modified A1AT promoter (SEQ ID NO: 9). The construct includes at least one enhancer element to stimulate promoter activity. In one embodiment, an enTTR enhancer (SEQ ID NO: 5) is included. In another embodiment, two copies of the ABP-S enhancer (SEQ ID NO: 6) proceed one copy of the enTTR enhancer (SEQ ID NO: 5). A synthetic polyA signal of about 75 nt (SEQ ID NO: 10) is included to mediate termination of human FVIII mRNA transcripts.

The vector is supplied as a suspension of AAVrh.10.hFVIII vector in formulation buffer. In one embodiment, the formulation buffer is 0.001% Pluronic F-68 in TMN200 (200 mM sodium chloride, 1 mM magnesium chloride, 20 mM Tris, pH 8.0).

7.2. Patient Population

Severe hemophilia A patients are the chosen study population for several reasons. Severe hemophilia A patients are defined as having less than 1% of normal Factor VIII (FVIII) activity thus requiring frequent infusions of FVIII to control their bleeding diathesis. This represents a significant burden with respect to carrying on a normal life and in addition, the blood levels of FVIII go through the well-known peaks and troughs pattern, which is not optimal. The fact that FVIII blood levels in severe patients is less than 1% makes it possible to reliably measure even low to moderate increases in FVIII blood levels after AAV.hFVIII has been administered. Recent clinical trials have borne out the validity of this approach.

Patients who are candidates for treatment are preferably adult males ≥18 years of age, diagnosed with moderate/ severe or severe hemophilia A. In one embodiment, the patient has a baseline FVIII activity ≤2% of normal or documented history of FVIII activity ≤2%. In some embodiments, a patient <18 years of age can be treated. Candidates for treatment include subjects who have had at least 3 bleeding episodes per year that require on-demand treatment with FVIII. Other candidates for treatment include subjects who are treated with a prophylactic regimen of FVIII. Other criteria demonstrating that the subject is appropriate for treatment includes at least 100 days exposure history to FVIII; no documented history of inhibitors (neutralizing antibodies) to exogenous FVIII; no known allergic reaction to exogenous FIX or any component of AAV.hFVIII.

Patients that are treated can have a baseline serum AAVhu.37 or AAVrh.10 (as appropriate for the chosen vector) neutralizing antibody (Nab) titer ≤1:5.

Subjects may be permitted to continue their standard of care treatment(s) (e.g., replacment FVIII) prior to and concurrently with the gene therapy treatment at the discretion of their caring physician. In the alternative, the physician may prefer to stop standard of care therapies prior to administering the gene therapy treatment and, optionally, resume standard of care treatments as a co-therapy after administration of the gene therapy.

7.3. Dosing & Route of Administration

Patients receive a single dose of AAVrh.10.hFVIII or AAVhu.37.hFVIII administered via a peripheral vein by infusion. The dose of AAVrh.10.hFVIII or AAVhu.37.hFVIII administered to a patient is about 5×10$^{11}$ GC/kg or 1.6×10$^{12}$ GC/kg or 5×10$^{12}$ GC/kg or 1×10$^{13}$ GC/kg. In order to ensure that empty capsids are removed from the dose of AAVrh.10.hFVIII or AAVhu.37.hFVIII that is administered to patients, empty capsids are separated from vector particles by cesium chloride gradient ultracentrifugation or by ion exchange chromatography during the vector purification process, as discussed above.

7.4. Measuring Clinical Objectives

Primary assessments are for safety of the administered product. The following assessments are conducted twice a week for 4 weeks after the administration of the product, weekly from week 6 to week 12, monthly throughout the remainder of the first year and at 6 month intervals for a total period of 5 years.
 a. Physical examination
 b. ECG
 c. Biochemical assessment: Serum electrolytes, BUN, creatinine, calcium, phosphate, total protein, albumin, LDH, CPK, AST, ALT, alkaline phosphatase, bilirubin
 d. Hematological assessment: CBC and differential, coagulation profile
 e. Urinalysis
 f. Immunological assessment:
 g. Serological response to hu.37 or rh.10 capsid and to Factor VIII
 h. T cell response to hu.37 or rh.10 capsid and Factor VIII antigens
 i. Assessment of vector DNA; qPCR measurements in plasma, urine and saliva Secondary assessments are based on measurements of transgene expression and activity as determined by
 a. Plasma Factor VIII levels and Factor VIII activity
 b. Clinical assessment of replacement Factor VIII requirements and frequency of spontaneous bleeding episodes

8. EXAMPLE 3: MANUFACTURE OF AAV.hFVIII 8.1. Plasmids used to Produce AAV.hFVIII AAVrh.10.hFVIII is produced by 3 plasmid DNA transfection of human
 HEK 293 MCB cells with:
 (i) a vector plasmid as described in Section 8.2.1.1-8.2.1.4
 (ii) an AAV helper plasmid termed pAAV2.rh10.KanR containing the AAV rep2 and cap rh10 wild-type genes described in Section 8.2.2.1 and
 (iii) a helper adenovirus plasmid termed pAdDeltaF6 (Kan) described in Section 8.2.3

AAVhu.37.hFVIII is produced by 3 plasmid DNA transfection of human HEK 293 MCB cells with:
 (i) a vector plasmid as described in Section 8.2.1.1-8.2.1.4
 (ii) an AAV helper plasmid termed pAAV2.hu.37.KanR containing the AAV rep2 and cap hu.37 wild-type genes described in Section 8.2.2.2 and
 (iii) a helper adenovirus plasmid termed pAdDeltaF6 (Kan) described in Section 8.2.3

8.2.1 Cis Plasmids (Vector Genome Expression Construct):

8.2.1.1 pAAV.E03.p3.hF8co-SQ.PA75 containing the human FVIII expression cassette (FIG. 1). This cis plasmid encodes the rAAV vector genome. Expression of the human FVIII-SQco cDNA is driven from the TTR promoter with an enTTR enhancer. The polyA signal for the expression cassette is an artificial polyA sequence of about 75 nt.

Description of the Sequence Elements

1. Inverted terminal repeats (ITR): AAV ITRs are sequences that are identical on both ends, but found in opposite orientation. The AAV2 (GenBank #NC001401) ITR sequences function as both the origin of vector DNA replication and the packaging signal for the vector genome, when AAV and adenovirus (ad) helper functions are provided in trans. As such, the ITR sequences represent the only cis acting sequences required for vector genome replication and packaging. The 5' ITR sequence used in the exemplified vector is shown in SEQ ID NO: 11. The 3' ITR sequence used in the exemplified vector is shown in SEQ ID NO: 12.

2. TTR promoter: The transthyretin promoter (SEQ ID NO: 7) and is used to drive high-level, liver specific hFVIII gene expression.

3. TTR Enhancer (enTTR): A 100 bp enhancer sequence (SEQ ID NO: 5) from transthyretin is present in the vector expression cassette to increase expression of FVIII.

4. Human coagulation factor VIII (FVIII) cDNA (SEQ ID NO: 1 shows native sequence; SEQ ID NO: 2 shows codon optimized sequence). The human coagulation factor 8 (FVIII) cDNA encodes a coagulation factor essential for the formation of blood clots. The hFVIII is a B-Domain Deleted sequence in which the B domain has been replaced with a short "SQ" sequence, as described herein. The hFVIII cDNA is codon optimized for expression in humans.

5. Artificial polyadenylation signal: (SEQ ID NO: 10) A 75 bp artificial polyadenylation signal provides cis sequences for efficient polyadenylation of the hFVIII mRNA. This element functions as a signal for transcriptional termination, a specific cleavage event at the 3' end of the nascent transcript followed by addition of a polyadenyl tail.

Figure 2:
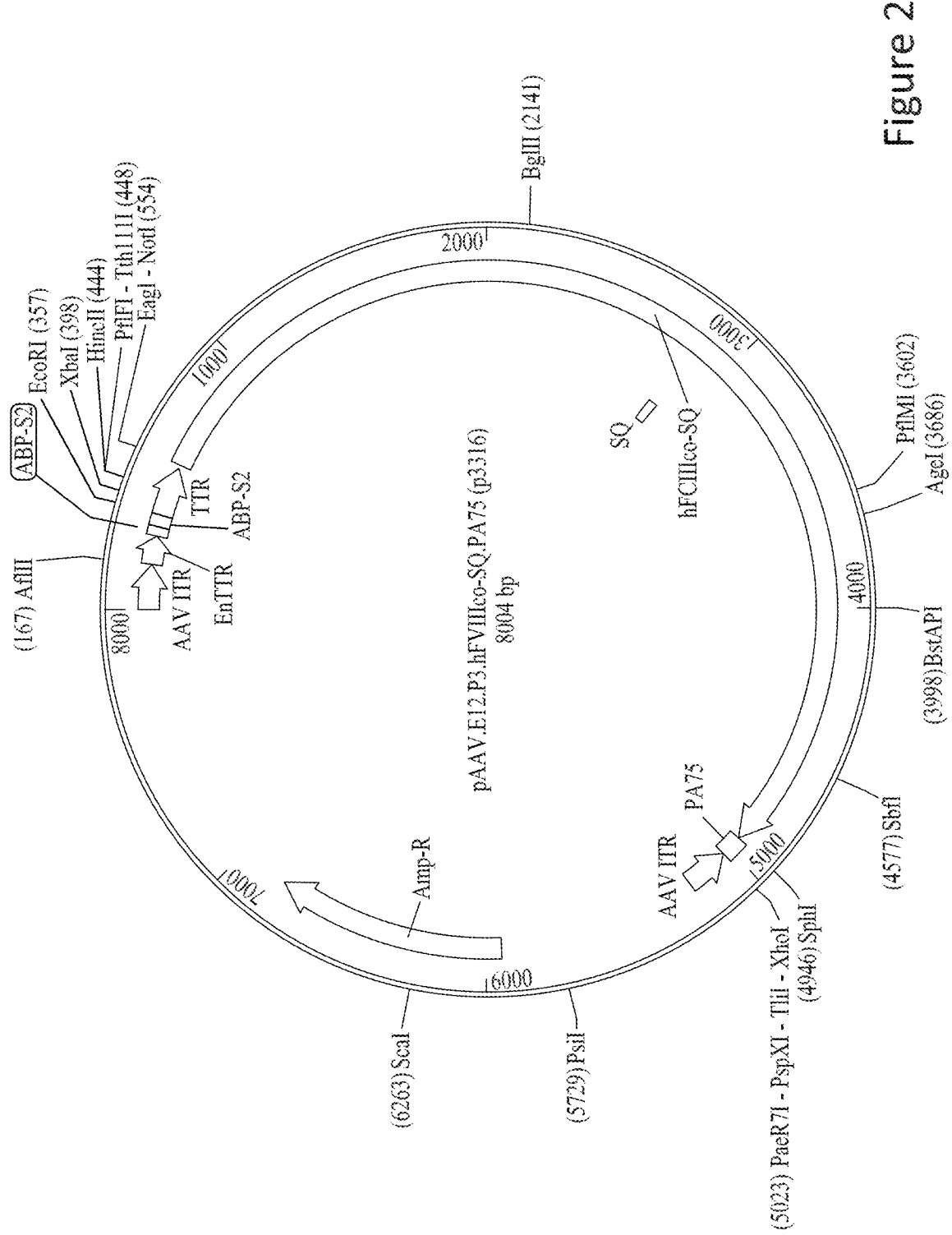
FIG. 2 is a schematic representation of pAAV.E12.P3.hF8co-SQ.PA75 cis plasmid.

8.2.1.2 pAAV.E12.p3.hF8co-SQ.PA75 containing the human FVIII expression cassette (FIG. 2). This cis plasmid encodes the rAAV vector genome. Expression of the human FVIII-SQco cDNA is driven from the TTR promoter with a ABPS and enTTR enhancer. The polyA signal for the expression cassette is an artificial polyA sequence of about 75 nt.

Description of the Sequence Elements

1. Inverted terminal repeats (ITR): Same as for 8.2.1.1

2. TTR promoter: Same as for 8.2.1.1

3. Enhancer: A shortened version of the 100 bp distal enhancer from the α1-microglogulin/bikunin precursor [ABP] to 42 bp (SEQ ID NO: 6) with two copies of the 100 bp enhancer sequence from transthyretin (enTTR) (SEQ ID NO: 5) are present in the vector expression cassette to increase expression of FVIII.

4. Human coagulation factor VIII (FVIII) cDNA: Same as for 8.2.1.1

5. Artificial polyadenylation signal: Same as for 8.2.1.1

Figure 3:
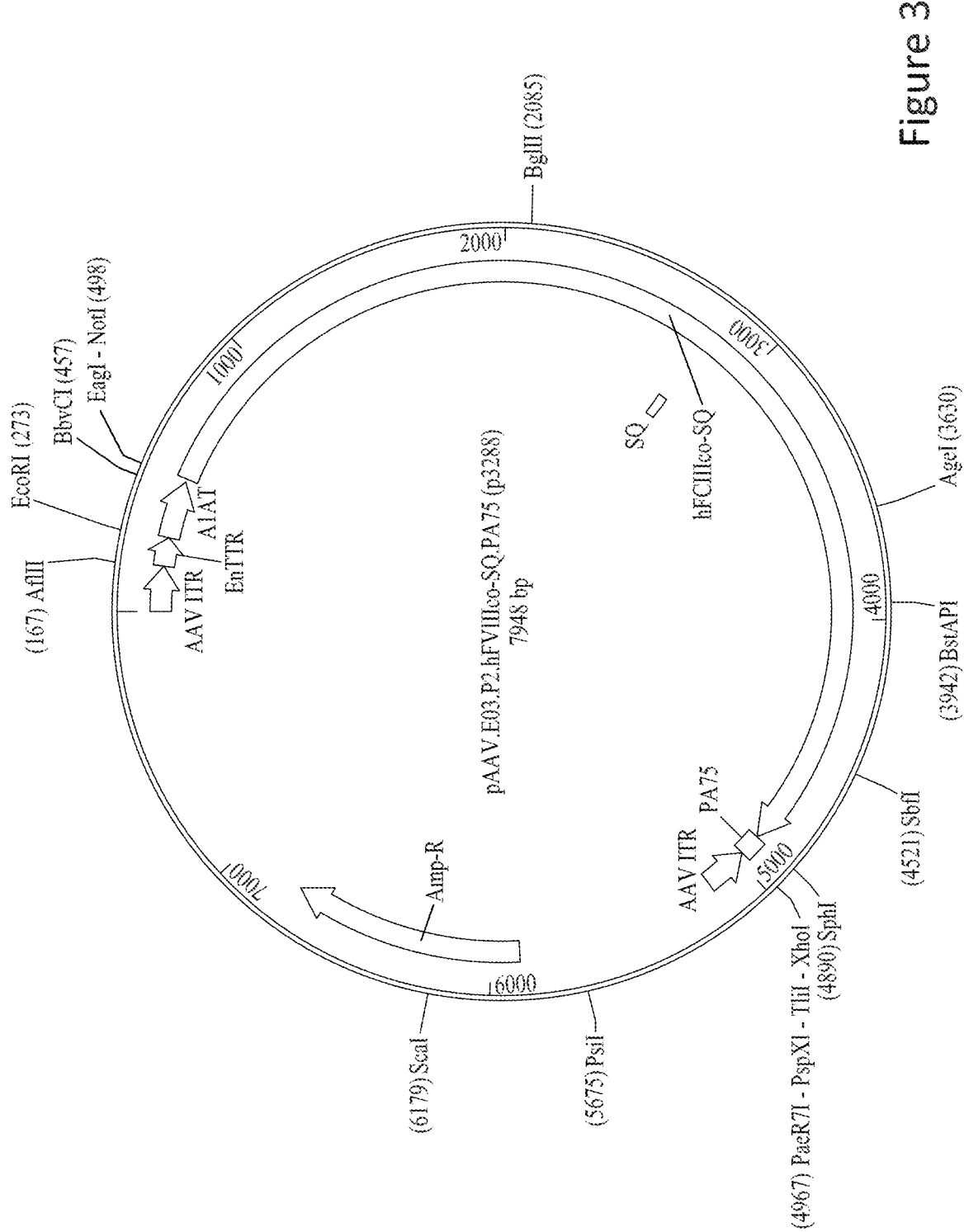
FIG. 3 is a schematic representation of pAAV.E03.P2.hF8co-SQ.PA75 cis plasmid.

8.2.1.3 pAAV.E03.p2.hF8co-SQ.PA75 containing the human FVIII expression cassette (FIG. 3). This cis plasmid encodes the rAAV vector genome. Expression of the human FVIII-SQco cDNA is driven from a modified A1AT promoter with a enTTR enhancer. The polyA signal for the expression cassette is an artificial polyA sequence of about 75 nt.

Description of the Sequence Elements
1. Inverted terminal repeats (ITR): Same as for 8.2.1.1
2. A1AT promoter: A modified SERINA1 [α1-antitrypsin] promoter (SEQ ID NO: 9) and is used to drive high-level, liver specific hFVIII gene expression.
3. TTR Enhancer (enTTR): A 100 bp enhancer sequence from transthyretin is present in the vector expression cassette to increase expression of FVIII.
4. Human coagulation factor VIII (FVIII) cDNA: Same as for 8.2.1.1
5. Artificial polyadenylation signal: Same as for 8.2.1.1

Figure 4:
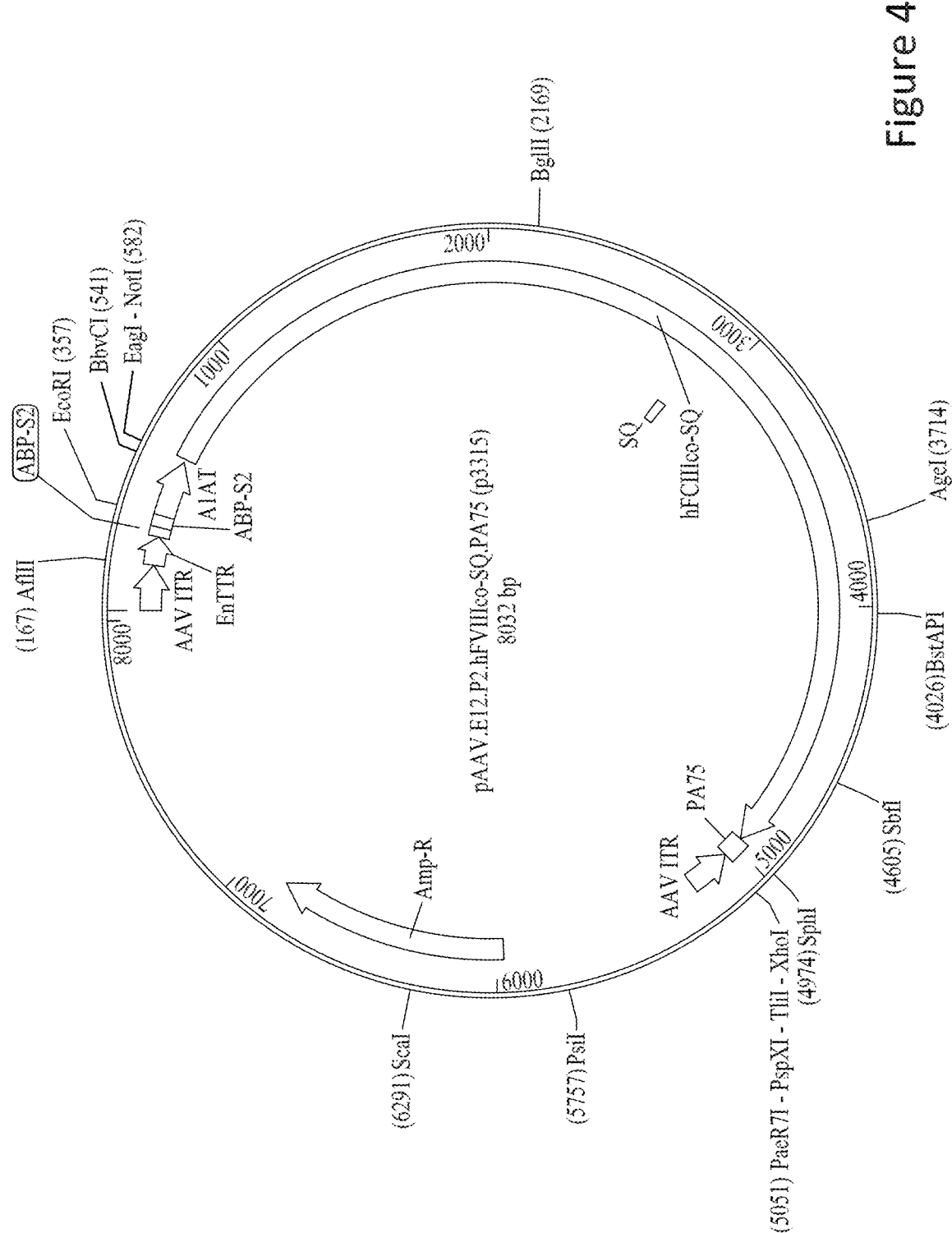
FIG. 4 is a schematic representation of pAAV.E12.P2.hF8co-SQ.PA75 cis plasmid.

8.2.1.4 pAAV.E12.p2.hF8co-SQ.PA75 containing the human FVIII expression cassette (FIG. 4). This cis plasmid encodes the rAAV vector genome. Expression of the human FVIII-SQco cDNA is driven from the TTR promoter with a ABPS and enTTR enhancer. The polyA signal for the expression cassette is an artificial polyA sequence of about 75 nt.

Description of the Sequence Elements
1. Inverted terminal repeats (ITR): Same as for 8.2.1.1
2. AlAT promoter: Same as for 8.2.1.3
3. Enhancer: Same as for 8.2.1.1
4. Human coagulation factor VIII (FVIII) cDNA: Same as for 8.2.1.1
5. Artificial polyadenylation signal: Same as for 8.2.1.1

8.2.2 Helper Plasmid 8.2.2.1 AAVrh10 Helper Plasmid pAAV2.rh10.KanR

This AAVrh10 helper plasmid (8,036 bp) encodes the 4 wild-type AAV2 rep proteins and the 3 wild-type AAV VP capsid proteins from serotype rh10. A novel AAV sequence was obtained from the liver tissue DNA of a rhesus monkey and designated AAV serotype rh10. To create the chimeric packaging construct, the AAV2 cap gene was removed from plasmid p5E18 and replaced with a PCR fragment of the AAVrh10 cap gene amplified from a primate liver DNA to give plasmid p5E18VD2/rh10. Note that the AAV p5 promoter which normally drives rep expression is moved in this construct from the 5' end of rep to the 3' end of the rh10 cap gene. This arrangement serves to introduce a spacer between the promoter and the rep gene (i.e., the plasmid backbone) to down-regulate expression of rep and increase the ability to support high titer vector production. The plasmid backbone in p5E18 is from pBluescript KS. All component parts of the plasmid have been verified by direct sequencing. Finally the ampicillin resistance gene was replaced by the kanamycin resistance gene to give pAAV2/rh10 (Kan).

8.2.2.2 AAVhu.37 Helper Plasmid pAAV2.hu.37.KanR

This AAVhu.37 helper plasmid (8,036 bp) encodes the 4 wild-type AAV2 rep proteins and the 3 wild-type AAV VP capsid proteins from serotype hu.37. A schematic of the pAAV2.rh10.KanR plasmid is shown below. To create the chimeric packaging construct, the AAV2 cap gene was removed from plasmid p5E18 and replaced with a PCR fragment of the AAVhu.37 cap gene amplified from a primate liver DNA to give plasmid p5E18VD2/hu.37. The plasmid backbone in p5E18 is from pBluescript KS. All component parts of the plasmid have been verified by direct sequencing. Finally the ampicillin resistance gene was replaced by the kanamycin resistance gene to give pAAV2/hu.37 (Kan).

8.2.3 pAdDeltaF6(Kan) Adenovirus Helper Plasmid

Plasmid pAdDeltaF6(Kan) is 15,774 bp in size. The plasmid contains the regions of adenovirus genome that are important for AAV replication, namely E2A, E4, and VA RNA (the adenovirus E1 functions are provided by the 293 cells), but does not contain other adenovirus replication or structural genes. The plasmid does not contain the cis elements critical for replication such as the adenoviral inverted terminal repeats and therefore, no infectious adenovirus is expected to be generated. It was derived from an E1, E3 deleted molecular clone of Ad5 (pBHG10, a pBR322 based plasmid). Deletions were introduced in the Ad5 DNA to remove expression of unnecessary adenovirus genes and reduce the amount of adenovirus DNA from 32 kb to ~12 kb. Finally the ampicillin resistance gene was replaced by the kanamycin resistance gene to give pAdΔF6(kan). The identity of these 3 adenovirus genes were confirmed by DNA plasmid sequencing performed by Qiagen Genomic Services on the plasmid source stock that was sent to Aldevron Inc. for plasmid DNA manufacturing. DNA Analysis revealed 100% homology with the 3 Adenovirus type 5 gene regions (GenBank Accession number AF369965).

8.2.4 Bacterial Master Cell Banks (MCB)

Bacterial MCBs for the three DNA production plasmids that are used to support the manufacture of DTX101 were produced by Aldevron Inc. Cell banks were made from the expansion of selected cultures and extensive testing was performed for qualification of each bacterial MCB following Aldevron SOPs and in accordance with CBER recommendations. Information regarding the specifics of bacterial MCB generation and testing for each of the three plasmids are performed and recorded.

8.2.5 Plasmid DNA Manufacturing

All plasmids used in the production process were produced by Aldevron Inc. under its GMP-STM quality system and infrastructure utilizing the most salient features of cGMP manufacturing; traceability, document control, and materials segregation. Information regarding the specifics of plasmid DNA generation and testing for each plasmid are performed and recorded.

8.2.6 Human Embryonic Kidney (HEK) 293 Master Cell Bank (MCB)

HEK 293 cells were originally generated by transforming HEK cells with sheared adenovirus type 5 DNA by Frank Graham and colleagues. The cells express the E1a and E1b gene products required for high-titer rAAV production. HEK293 cells are adherent and highly transfectable yielding high-titers of rAAV upon DNA plasmid transfection.

8.3 Recombinant AAV Vector Manufacturing 8.3.1 Description of the Manufacturing Process 1. Cell Seeding: A qualified human embryonic kidney 293 cell line is used for the production process. Cells are cultivated in medium composed of Dulbecco's Modified Eagle Medium (DMEM), supplemented with 10% gamma irradiated Fetal Bovine Serum (FBS). The cells are anchorage dependent and cell disassociation is accomplished using TrypLE Select, a non-animal cell dissociation reagent. The cells are maintained at 37° C. (+/−1° C.), in 5% (+/−0.5%) $CO_2$ atmosphere.

2. Transient Transfection: Following 3 days of growth (DMEM media+10% FBS), Hyperstack cell culture media is replaced with fresh, serum free DMEM media and transfected with the 3 production plasmids using an optimized PEI precipitation method.

Sufficient DNA plasmid transfection complex is prepared in the BSC to transfect twenty Corning 36-layer Hyperstacks (per BDS lot). Initially a DNA/PEI mixture is prepared containing 3.0 mg of pDTX.hFIX.101 vector plasmid, 60 mg of pAdDeltaF6(Kan), 30 mg of pAAV2.rh10.KanR AAV helper plasmid and GMP grade PEI (PEIPro, PolyPlus Transfection SA). After mixing well, the solution is allowed to sit at room temperature for 25 min. and then added to serum-free media to quench the reaction and then added to the Corning 36-layer Hyperstacks. The transfection mixture is equalized between all 36 layers of the Hyperstack and the cells are incubated at 37° C. (+/−2° C.) in a 5% (+/−0.5%) CO$_2$ atmosphere for 5 days.

3. Cell Media Harvesting: Transfected cells and media are harvested from each Hypertack using disposable bioprocess bags by aseptically draining the medium out of the units. Following the harvest of media, the ~80 liter volume is supplemented with MgCl$_2$ to a final concentration of 2 mM (co-factor for Benzonase) and Benzonase nuclease (Cat#: 1.016797.0001, Merck Group) added to a final concentration of 25 units/ml. The product (in a disposable bioprocess bag) is incubated at 37° C. for 2-3 hr in an incubator to provide sufficient time for enzymatic digestion of residual cellular and plasmid DNA present in the harvest as a result of the transfection procedure. This step is performed to minimize the amount of residual DNA in the final vector DP. After the incubation period, NaCl is added to a final concentration of 500 mM to aid in the recovery of the product during filtration and downstream tangential flow filtration.

4. Clarification: Cells and cellular debris are removed from the product using a depth filter capsule (1.2 μm/0.22 μm) connected in series as a sterile, closed tubing and bag set that is driven by a peristaltic pump. The media is passed through a Sartorius Sartoguard PES capsule filter (1.2 μm/0.22 μm) (Sartorius Stedim Biotech Inc.).

5. Large-scale Tangential Flow Filtration: Volume reduction (10-20 fold) of the clarified product is achieved using Tangential Flow Filtration (TFF) using a custom sterile, closed bioprocessing tubing, bag and membrane set produced by Spectrum Labs.

8.4 Readministration with Second Vector 8.4.1 Readministration of AAV3B or AAV5

The efficiency of vector readministration using AAV3B or AAV5 in rhesus macaques previously treated with AAVrh10 or AAV8 vectors was evaluated. Vectors as shown in Table 4 were produced as previously described in which the vector was recovered from the supernatant following triple transfection in HEK293 cells and purified on an iodixanol gradient. Vector titer was determined by a digital PCR method.

Twenty four male rhesus macaques (3-5 years old) were enrolled into study in 8 groups (n=3/group; Table 1) based on the status of pre-existing NAb. Macaques were injected on day zero with 1.0×10$^{13}$ GC/kg AAV.TBG.hCG.WPRE, with the AAV vector as shown in Table 4. At week 12, macaques received a second injection with 1.0×10$^{13}$ GC/kg AAV.TBG.hCG.WPRE, with the AAV vector as shown in Table 4. Liver biopsies were performed at week 2 and week 14, and a necropsy was performed at week 26.

TABLE 4

Cohort and Vector Summary

| Cohort | Animal ID | 1st Injection | 2nd Injection |
|---|---|---|---|
| G1A | RA0931<br>RA1388<br>RQ9745 | PBS | AAV3B.TBG.rhAFP |
| G1B | RA0923<br>RQ1275<br>RQ9383 | PBS | AAV5.TBG.rhAFP |
| G2A | RA0985<br>RQ9638<br>RQ9746 | AAVrh10.TBG.rhCG.WPRE | AAV3B.TBG.rhAFP |
| G2B | RA0992<br>RA1322<br>RA1417 | AAVrh10.TBG.rhCG.WPRE | AAV5.TBG.rhAFP |
| G3A | RA1234<br>RQ9737<br>RQ9751 | AAV8.TBG.rhCG.WPRE | AAV3B.TBG.rhAFP |
| G3B | RA1339<br>RA1390<br>RQ9805 | AAV8.TBG.rhCG.WPRE | AAV5.TBG.rhAFP |
| G4 | RA0548<br>RA0658<br>RQ9840 | AAV3B.TBG.rhCG.WPRE | N/A |
| G5 | RA0968<br>RA1208<br>RA1239 | AAV5.TBG.rhCG.WPRE | N/A |

Expression levels of transgenes (rhCG—rhesus chorionic gonadotropin b subunit; rhAFP—rhesus alpha fetoprotein) in the serum were measured by enzyme-linked immunosorbent assay (ELISA). To measure vector DNA copies in liver, QPCR assays were performed on total cellular DNA extracted from liver samples collected during liver biopsy and necropsy. AAV NAb assay was performed as previously described. Liver sections were stained with an anti-CG antibody for imaging.

FIG. 15 shows a comparison of rhCG expression levels by AAVrh10, AAV8, AAV3B and AAV5 vectors (first vector injection). FIG. 16A-16D shows rhCG vector DNA copies in liver at different time points. FIG. 17A-17B shows rhAFP levels after readministration (second vector injection) with AAV3B (FIG. 17A) or AAV5 (FIG. 17B) vectors expressing rhAFP. FIG. 18B and FIG. 18B shows rhAFP vector genome copies in liver. FIG. 19 shows differential AAV Nab response in macaques.

In naïve animals, clade E vectors (AAVrh10 & AAV8) demonstrated the highest levels of periportal gene transfer with AAV5 vectors having the lowest; the periportal zone is nearest to the entering vascular supply, receives the most oxygenated blood, and is an important region of the liver for metabolic processes. AAVrh10 and AAV5 elicited higher levels of neutralizing antibodies (NAb) than AAV8 and AAV3B. Significant animal-to-animal variation in transgene expression was noted with AAV3B in seronegative animals. Within the short time frame tested, NAb elicited from AAVrh10 appears to have inhibited subsequent in vivo transduction with the serologically distinct AAV3B serotype; prior exposure to AAV8 did not interfere with AAV3B transduction.

All publications cited in this specification, as well as U.S. provisional patent application Nos. 62/323,336, 62/331,807, and 62/428,866, are incorporated herein by reference. Similarly, the SEQ ID NOs which are referenced herein and which appear in the appended Sequence Listing, and the sequence listing itself, are incorporated by reference. While the invention has been described with reference to particular embodiments, it will be appreciated that modifications can be made without departing from the spirit of the invention. Such modifications are intended to fall within the scope of the appended claims.

Sequence Listing Free Text

The following information is provided for sequences containing free text under numeric identifier <223>.

| SEQ ID NO: (containing free text) | Free text under <223> |
|---|---|
| 4 | <223> constructed sequence |
| 5 | <223> constructed sequence |
| 6 | <223> constructed sequence |
| 7 | <223> constructed sequence |
| 8 | <223> constructed sequence |
| 9 | <223> constructed sequence |
| 10 | <223> constructed sequence |
| 11 | <223> constructed sequence |
| 12 | <223> constructed sequence |
| 13 | <223> constructed sequence |

| SEQ ID NO: (containing free text) | Free text under <223> |
|---|---|
| 14 | <223> constructed sequence |
| 15 | <223> constructed sequence |
| 16 | <223> constructed sequence |
| 17 | <223> AAVhu.37 capsid |
| 18 | <223> AAVrh.10 capsid |
| 19 | <223> constructed sequence |
| 20 | <223> AAV3B capsid |

What is claimed is:

1. A recombinant adeno-associated virus (rAAV) comprising an AAV capsid and a vector genome packaged therein, said vector genome comprising:
   an AAV 5'-inverted terminal repeat (ITR) sequence;
   a liver-specific promoter;
   a coding sequence encoding a human Factor VIII having coagulation function; and
   an AAV 3'-ITR sequence,
   wherein said coding sequence comprises the nucleotide sequence as set forth in SEQ ID NO: 2.

2. The rAAV according to claim 1, wherein the AAV capsid is a hu.37 capsid.

3. The rAAV according to claim 1, wherein the AAV 5'-ITR is from AAV2.

4. The rAAV according to claim 3, wherein the AAV 5'-ITR comprises the nucleotide sequence as set forth in SEQ ID NO: 11.

5. The rAAV according to claim 1, wherein the AAV 3'-ITR is from AAV2.

6. The rAAV according to claim 5, wherein the AAV 3'-ITR comprises the nucleotide sequence as set forth in SEQ ID NO: 12.

7. The rAAV according to claim 1, wherein the AAV 5'-ITR and AAV 3'-ITR are from AAV2.

8. The rAAV according to claim 1, wherein the liver-specific promoter is a transthyretin (TTR) promoter.

9. The rAAV according to claim 8, wherein the TTR promoter comprises the nucleotide sequence as set forth in SEQ ID NO: 7.

10. The rAAV according to claim 1, wherein the vector genome further comprises an enhancer.

11. The rAAV according to claim 10, wherein the enhancer is a liver-specific enhancer.

12. The rAAV according to claim 11, wherein the liver-specific enhancer is a transthyretin enhancer (enTTR).

13. The rAAV according to claim 12, wherein the enTTR comprises the nucleotide sequence as set forth in SEQ ID NO: 5.

14. The rAAV according to claim 1, wherein the vector genome further comprises a polyA sequence.

15. The rAAV according to claim 14, wherein the polyA sequence comprises the nucleotide sequence as set forth in SEQ ID NO: 10.

16. The rAAV according to claim 1, wherein the vector genome is 5 kilobases to 5.5 kilobases in size.

17. An aqueous suspension comprising an aqueous suspending liquid and $1\times10^{12}$ to $1\times10^{14}$ genome copies (GC)/kilogram of the rAAV of claim 1, wherein the aqueous suspension is suitable for administration to a patient with hemophilia A.

18. The aqueous suspension according to claim 17, wherein the suspension further comprises a surfactant, a preservative, and/or a buffer in the aqueous suspending liquid.

19. A recombinant adeno-associated virus (rAAV) comprising an AAVhu.37 capsid and a vector genome packaged therein, said vector genome comprising:
   an AAV 5'-inverted terminal repeat (ITR) sequence;
   a transthyretin (TTR) promoter;
   transthyretin enhancer (enTTR);
   a coding sequence encoding a human Factor VIII having coagulation function; and
   an AAV 3'-ITR sequence,
   wherein said coding sequence comprises the nucleic acid sequence set forth in SEQ ID NO: 2.

* * * * *

SEQUENCE LISTING

<160> NUMBER OF SEQ ID NOS: 20

<210> SEQ ID NO 1
<211> LENGTH: 4371
<212> TYPE: DNA
<213> ORGANISM: Homo sapiens

<400> SEQUENCE: 1

```
atgcaaatag agctctccac ctgcttcttt ctgtgccttt tgcgattctg ctttagtgcc      60
accagaagat actacctggg tgcagtggaa ctgtcatggg actatatgca aagtgatctc     120
ggtgagctgc ctgtggacgc aagatttcct cctagagtgc caaaatcttt tccattcaac     180
acctcagtcg tgtacaaaaa gactctgttt gtagaattca cggatcacct tttcaacatc     240
gctaagccaa ggccaccctg gatgggtctg ctaggtccta ccatccaggc tgaggtttat     300
gatacagtgg tcattacact taagaacatg gcttcccatc ctgtcagtct tcatgctgtt     360
ggtgtatcct actggaaagc ttctgaggga gctgaatatg atgatcagac cagtcaaagg     420
gagaaagaag atgataaagt cttccctggt ggaagccata catatgtctg gcaggtcctg     480
aaagagaatg gtccaatggc ctctgaccca ctgtgcctta cctactcata tctttctcat     540
gtggacctgg taaaagactt gaattcaggc ctcattggag ccctactagt atgtagagaa     600
gggagtctgg ccaaggaaaa gacacagacc ttgcacaaat ttatactact ttttgctgta     660
tttgatgaag ggaaaagttg gcactcagaa acaaagaact ccttgatgca ggatagggat     720
gctgcatctg ctcgggcctg gcctaaaatg cacacagtca atggttatgt aaacaggtct     780
ctgccaggtc tgattggatg ccacaggaaa tcagtctatt ggcatgtgat tggaatgggc     840
accactcctg aagtgcactc aatattcctc gaaggtcaca catttcttgt gaggaaccat     900
cgccaggcgt cctggaaat ctcgccaata actttcctta ctgctcaaac actcttgatg     960
gaccttggac agtttctact gttttgtcat atctcttccc accaacatga tggcatggaa    1020
gcttatgtca agtagacag ctgtccagag gaaccccaac tacgaatgaa aaataatgaa    1080
gaagcggaag actatgatga tgatcttact gattctgaaa tggatgtggt caggtttgat    1140
gatgacaact ctccttcctt tatccaaatt cgctcagttg ccaagaagca tcctaaaact    1200
tgggtacatt acattgctgc tgaagaggag gactgggact atgctccctt agtcctcgcc    1260
cccgatgaca aagttataa agtcaatat ttgaacaatg ccctcagcg gattggtagg    1320
aagtacaaaa aagtccgatt tatggcatac acagatgaaa ccttttaagac tcgtgaagct    1380
attcagcatg aatcaggaat cttgggacct tactttatg gggaagttgg agacacactg    1440
ttgattatat ttaagaatca agcaagcaga ccatataaca tctaccctca cggaatcact    1500
gatgtccgtc ctttgtattc aaggagatta ccaaaaggtg taaacatttt gaaggatttt    1560
```

```
ccaattctgc caggagaaat attcaaatat aaatggacag tgactgtaga agatgggcca    1620
actaaatcag atcctcggtg cctgacccgc tattactcta gtttcgttaa tatggagaga    1680
gatctagctt caggactcat tggccctctc ctcatctgct acaaagaatc tgtagatcaa    1740
agaggaaacc agataatgtc agacaagagg aatgtcatcc tgttttctgt atttgatgag    1800
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt ccttcctgtc ttcttctctg gatataccct caaacacaaa    2040
atggtctatg aagacacact caccctattc ccattctcag agaaactgt cttcatgtcg     2100 atggaaaacc caggtctatg gattctgggg tgccacaact cagactttcg aacagaggc     2160 atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctcccaga atccaccagt cttgaaacgc atcaacggg aaataactcg tactactctt     2340
cagtcagatc aagaggaaat tgactatgat gataccatat cagttgaaat gaagaaggaa    2400
gattttgaca tttatgatga ggatgaaaat cagagccccc gcagctttca aaagaaaaca    2460
cgacactatt ttattgctgc agtggagagg ctctgggatt atgggatgag tagctcccca    2520
catgttctaa gaaacagggc tcagagtggc agtgtccctc agttcaagaa agttgtttc     2580 caggaattta ctgatggctc ctttactcag cccttatacc gtggagaact aaatgaacat    2640
ttgggactcc tgggggccata taagagca gaagttgaag ataatatcat ggtaactttc     2700
agaaatcagg cctctcgtcc ctattccttc tattctagcc ttatttctta tgaggaagat    2760
cagaggcaag gagcagaacc tagaaaaac tttgtcaagc ctaatgaaac caaaacttac     2820
ttttggaaag tgcaacatca tatggcaccc actaaagatg agttttgactg caaagcctgg    2880 gcttatttct ctgatgttga cctggaaaaa gatgtgcact caggcctgat tggaccccctt   2940 ctggtctgcc acactaacac actgaaccct gctcatggga gacaagtgac agtacaggaa    3000
tttgctctgt ttttcaccat cttttgatgag accaaaagct ggtacttcac tgaaaatatg    3060
gaaagaaact gcagggctcc ctgcaatatc cagatggaag atcccacttt taaagagaat    3120
tatcgcttcc atgcaatcaa tggctacata atggatacac tacctggctt agtaatggct    3180
caggatcaaa ggattcgatg gtatctgctc agcatgggca gcaatgaaaa catccattct    3240
attcatttca gtggacatgt gttcactgta cgaaaaaaag aggagtataa aatggcactg    3300
tacaatctct atccaggtgt ttttgagaca gtggaaatgt taccatccaa agctggaatt    3360
tggcgggtgg aatgccttat tggcgagcat ctacatgctg ggatgagcac acttttctg     3420 gtgtacagca ataagtgtca gactcccctg gaatggctt ctggacacat tagagatttt      3480
cagattacag cttcaggaca atatggacag tgggccccaa agctggccag acttcattat    3540
tccggatcaa tcaatgcctg gagcaccaag gagccctttt cttggatcaa ggtggatctg    3600
ttggcaccaa tgattattca cggcatcaag acccagggtg cccgtcagaa gttctccagc    3660
ctctacatct ctcagtttat catcatgtat agtcttgatg ggaagaagtg gcagacttat    3720
cgaggaaatt ccactggaac cttaatggtc ttctttggca atgtggattc atctgggata    3780
aaacacaata tttttaaccc tccaattatt gctcgataca tccgtttgca cccaactcat    3840
tatagcattc gcagcactct tcgcatggag ttgatgggct gtgatttaaa tagttgcagc    3900
atgccattgg gaatggagag taaagcaata tcagatgcac agattactgc ttcatcctac    3960
```

| | |
|---|---|
| tttaccaata tgtttgccac ctggtctcct tcaaaagctc gacttcacct ccaagggagg | 4020 |
| agtaatgcct ggagacctca ggtgaataat ccaaaagagt ggctgcaagt ggacttccag | 4080 |
| aagacaatga aagtcacagg agtaactact cagggagtaa aatctctgct taccagcatg | 4140 |
| tatgtgaagg agttcctcat ctccagcagt caagatggcc atcagtggac tctctttttt | 4200 |
| cagaatggca agtaaaggt ttttcaggga aatcaagact ccttcacacc tgtggtgaac | 4260 |
| tctctagacc caccgttact gactcgctac cttcgaattc accccagag ttgggtgcac | 4320 |
| cagattgccc tgaggatgga ggttctgggc tgcgaggcac aggacctcta c | 4371 |

<210> SEQ ID NO 2
<211> LENGTH: 4374
<212> TYPE: DNA
<213> ORGANISM: Artificial Sequence
<220> FEATURE:
<223> OTHER INFORMATION: constructed sequence

<400> SEQUENCE: 2

| | |
|---|---|
| atgcagatcg agctgagcac ctgcttcttc ctgtgcctgc tgcggttctg cttctccgcc | 60 |
| acccggcggt actacctggg agccgtggag ctgagctggg attacatgca gagcgatctg | 120 |
| ggagagctgc cagtggatgc ccggttccca ccacgggtgc caaagagctt cccattcaac | 180 |
| accagcgtgg tgtacaagaa gaccctgttc gtggagttca ccgatcacct gttcaacatc | 240 |
| gccaagccac ggccacccctg gatgggactg ctgggaccaa ccatccaggc cgaggtgtac | 300 |
| gataccgtgg tgatcaccct gaagaacatg gcctctcatc ctgtgtccct gcacgccgtg | 360 |
| ggagtgagct actggaaggc cagcgaggga gccgagtacg atgatcagac cagccagcgg | 420 |
| gagaaggagg atgataaggt gttcccagga ggaagccaca cctacgtgtg gcaggtgctg | 480 |
| aaggagaacg gaccaatggc cagcgatcca ctgtgcctga cctacagcta cctgagccac | 540 |
| gtggatctgg tgaaggatct gaacagcgga ctgatcggag ccctgctggt gtgccgggag | 600 |
| ggaagcctgg ccaaggagaa gacccagacc ctgcacaagt tcatcctgct gttcgccgtg | 660 |
| ttcgatgagg gaaagagctg gcacagcgag accaagaaca gcctgatgca ggatcgggat | 720 |
| gccgccagcg cccgggcctg gccaaagatg cacaccgtga acggatacgt gaaccggagc | 780 |
| ctgccaggac tgatcggatg ccaccggaag agcgtgtact ggcacgtgat cggaatggga | 840 |
| accaccccag aggtgcactc tatcttcctg gagggacaca ccttttctgg tgcggaaccac | 900 |
| cggcaggcca gcctggagat cagcccaatc accttcctga ccgcccagac cctgctgatg | 960 |
| gatctgggac agttcctgct gttctgccat atcagcagcc accagcacga tggaatggag | 1020 |
| gcctacgtga aggtggatag ctgcccagag gagccacagc tgcggatgaa gaacaacgag | 1080 |
| gaggccgagg attacgatga tgatctgacc gatagcgaga tggatgtggt gcggttcgat | 1140 |
| gatgataaca gcccaagctt catccagatc cggagcgtgg ccaagaagca cccaaagacc | 1200 |
| tgggtgcact acatcgccgc cgaggaggag gattgggatt acgccccact ggtgctggcc | 1260 |
| cctgatgatc ggagctacaa gagccagtac ctgaacaacg gaccacagcg gatcggacgg | 1320 |
| aagtacaaaa aagtgcggtt catggcctac accgatgaga ccttcaagac ccgggaggcc | 1380 |
| atccagcacg agagcggaat cctgggacca ctgctgtacg agaggtggg agataccctg | 1440 |
| ctgatcatct tcaagaacca ggccagccgg ccatacaaca tctacccaca cggaatcacc | 1500 |
| gatgtgcggc cactgtacag ccggcggctg ccaaagggag tgaagcacct gaaggatttc | 1560 |
| ccaatcctgc caggagagat cttcaagtac aagtggacag tgacagtgga ggatggacca | 1620 |

```
accaagtctg atccaagatg cctgaccaga tactacagca gctttgtgaa catggagaga    1680
gacctggcct ctggactgat tggaccactg ctgatctgct acaaggagtc tgtggatcag    1740
agaggaaacc agatcatgtc tgataagaga aatgtgatcc tgttctctgt gtttgatgag    1800
aacagaagct ggtacctgac agagaacatc cagagattcc tgccaaaccc agccggagtg    1860
cagctggagg atccagagtt ccaggccagc aacatcatgc acagcatcaa cggatacgtg    1920
ttcgatagcc tgcagctgag cgtgtgcctg cacgaggtgg cctattggta tatcctgagc    1980
atcggagccc agaccgattt cctgagcgtg ttcttcagcg atacacctt caagcacaag     2040 atggtgtacg aggatacccc gaccctgttc ccattctccg agagaccgt gttcatgagc     2100 atggagaacc aggactgtg gatcctggga tgccacaact ctgatttcag aaacagagga    2160
atgactgccc tgctgaaagt gtccagctgt gataagaaca ctggagatta ctatgaggat    2220
agctatgagg atatctctgc ctacctgctg agcaagaaca atgccattga gccaagaagc    2280
ttcagccaga acccaccagt gctgaagaga caccagagag atcaccag aaccaccctg     2340 cagtctgatc aggaggagat tgattatgat gataccatct ctgtggagat gaagaaggag    2400
gattttgata tctatgatga ggatgagaac cagagcccaa gaagcttcca gaagaagacc    2460
agacactact tcatcgctgc agtggagaga ctgtgggatt atggaatgag cagcagccca    2520
cacgtgctga gaaacagagc ccagagcgga tctgtgccac agttcaagaa ggtggtgttc    2580
caggagttca ccgatggaag cttcacccag ccactgtacc gggagagct gaacgagcac    2640 ctgggactgc tgggaccata catccgggcc gaggtggagg ataacatcat ggtgaccttc    2700
cggaaccagc ccagccggcc atacagcttc tacagcagcc tgatcagcta cgaggaggat    2760
cagcggcagg gagccgagcc acggaagaac ttcgtgaagc caaacgagac caagacctac    2820
ttctggaagg tgcagcacca catggcccca accaaggatg agttcgattg caaggcctgg    2880
gcctacttca gcgatgtgga tctggagaag gatgtgcaca gcggactgat cggaccactg    2940
ctggtgtgcc acaccaacac cctgaaccca gcccacggac ggcaggtgac cgtgcaggag    3000
ttcgccctgt tcttcaccat cttcgatgag accaagagct ggtacttcac cgagaacatg    3060
gagcggaact gccgggcccc ttgcaacatc cagatggagg atccaacctt caaggagaac    3120
taccggttcc acgccatcaa cggatacatc atggataccc tgccaggact ggtgatggcc    3180
caggatcagc ggatccggtg gtacctgctg agcatgggaa gcaacgagaa catccacagc    3240
atccacttca gcggacacgt gttcaccgtg cggaagaagg aggagtacaa gatggccctg    3300
tacaacctgt acccaggagt gttcgagacc gtggagatgc tgccaagcaa ggccggaatc    3360
tggcgggtgg agtgcctgat cggagagcac ctgcacgccg aatgagcac cctgttcctg    3420 gtgtacagca caagtgcca gaccccactg ggaatggcca gcggacacat ccgggatttc    3480
cagatcaccg ccagcggaca gtacggacag tgggcccaa agctggcccg gctgcactac    3540
agcggaagca tcaacgcctg gagcaccaag gagccattca gctggatcaa gtggatctg    3600 ctggccccaa tgatcatcca cggaatcaag acccaggagc cccggcagaa gttcagcagc    3660
ctgtacatca gccagttcat catcatgtac agcctggatg gaaagaagtg gcagacctac    3720
cggggaaaca gcaccggaac cctgatggtg ttcttcggaa acgtggatag cagcggaatc    3780
aagcacaaca tcttcaaccc accaatcatc gcccgataca tccggctgca cccaacccac    3840
tacagcatca gaagcaccct gcggatggag ctgatgggat gtgatctgaa cagctgctcc    3900
atgccactgg gaatggagag caaggccatc agcgatgccc agatcaccgc cagcagctac    3960
ttcaccaaca tgttcgccac ctggagccca agcaaggccc ggctgcacct gcagggacgg    4020
```

-continued

```
agcaacgcct ggcggccaca ggtgaataac ccaaaggagt ggctgcaggt ggatttccag    4080
aagaccatga aggtgaccgg agtgaccacc cagggagtga agagcctgct gactagcatg    4140
tatgtgaagg agttcctgat cagcagcagc caggatggac accagtggac cctgttcttc    4200
cagaacggaa aggtgaaggt gttccaggga accaggata gcttcacccc agtggtgaac     4260
agcctggatc caccactgct gacccgatac ctgcggatcc acccacagag ctgggtgcac    4320
cagatcgccc tgagaatgga ggtgctggga tgcgaggccc aggatctgta ctga          4374
```

<210> SEQ ID NO 3
<211> LENGTH: 1457
<212> TYPE: PRT
<213> ORGANISM: Homo sapiens

<400> SEQUENCE: 3

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
```

```
            305                 310                 315                 320
Asp Leu Gly Gln Phe Leu Leu Phe Cys His Ile Ser Ser His Gln His
                325                 330                 335
Asp Gly Met Glu Ala Tyr Val Lys Val Asp Ser Cys Pro Glu Glu Pro
                340                 345                 350
Gln Leu Arg Met Lys Asn Asn Glu Ala Glu Asp Tyr Asp Asp Asp
                355                 360                 365
Leu Thr Asp Ser Glu Met Asp Val Val Arg Phe Asp Asp Asn Ser
            370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Glu Asp Trp Asp Tyr Ala Pro
                405                 410                 415
Leu Val Leu Ala Pro Asp Asp Arg Ser Tyr Lys Ser Gln Tyr Leu Asn
                420                 425                 430
Asn Gly Pro Gln Arg Ile Gly Arg Lys Tyr Lys Lys Val Arg Phe Met
                435                 440                 445
Ala Tyr Thr Asp Glu Thr Phe Lys Thr Arg Glu Ala Ile Gln His Glu
            450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
                500                 505                 510
Gly Val Lys His Leu Lys Asp Phe Pro Ile Leu Pro Gly Glu Ile Phe
            515                 520                 525
Lys Tyr Lys Trp Thr Val Thr Val Glu Asp Gly Pro Thr Lys Ser Asp
            530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Ile Met Ser Asp Lys Arg Asn Val
                580                 585                 590
Ile Leu Phe Ser Val Phe Asp Glu Asn Arg Ser Trp Tyr Leu Thr Glu
            595                 600                 605
Asn Ile Gln Arg Phe Leu Pro Asn Pro Ala Gly Val Gln Leu Glu Asp
            610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                645                 650                 655
Tyr Ile Leu Ser Ile Gly Ala Gln Thr Asp Phe Leu Ser Val Phe Phe
                660                 665                 670
Ser Gly Tyr Thr Phe Lys His Lys Met Val Tyr Glu Asp Thr Leu Thr
            675                 680                 685
Leu Phe Pro Phe Ser Gly Glu Thr Val Phe Met Ser Met Glu Asn Pro
            690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
```

-continued

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Val Leu
            755                 760                 765

Lys Arg His Gln Arg Glu Ile Thr Arg Thr Thr Leu Gln Ser Asp Gln
            770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Pro His Val Leu Arg Asn Arg Ala Gln
            835                 840                 845

Ser Gly Ser Val Pro Gln Phe Lys Lys Val Val Phe Gln Glu Phe Thr
850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
                900                 905                 910

Ser Leu Ile Ser Tyr Glu Glu Asp Gln Arg Gln Gly Ala Glu Pro Arg
            915                 920                 925

Lys Asn Phe Val Lys Pro Asn Glu Thr Lys Thr Tyr Phe Trp Lys Val
            930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu Phe Ala Leu Phe Phe Thr Ile Phe
            995                 1000                1005

Asp Glu Thr Lys Ser Trp Tyr Phe Thr Glu Asn Met Glu Arg Asn
    1010                1015                1020

Cys Arg Ala Pro Cys Asn Ile Gln Met Glu Asp Pro Thr Phe Lys
    1025                1030                1035

Glu Asn Tyr Arg Phe His Ala Ile Asn Gly Tyr Ile Met Asp Thr
    1040                1045                1050

Leu Pro Gly Leu Val Met Ala Gln Asp Gln Arg Ile Arg Trp Tyr
    1055                1060                1065

Leu Leu Ser Met Gly Ser Asn Glu Asn Ile His Ser Ile His Phe
    1070                1075                1080

Ser Gly His Val Phe Thr Val Arg Lys Lys Glu Glu Tyr Lys Met
    1085                1090                1095

Ala Leu Tyr Asn Leu Tyr Pro Gly Val Phe Glu Thr Val Glu Met
    1100                1105                1110

Leu Pro Ser Lys Ala Gly Ile Trp Arg Val Glu Cys Leu Ile Gly
    1115                1120                1125

Glu His Leu His Ala Gly Met Ser Thr Leu Phe Leu Val Tyr Ser
    1130                1135                1140

```
Asn Lys Cys Gln Thr Pro Leu Gly Met Ala Ser Gly His Ile Arg
    1145                1150                1155

Asp Phe Gln Ile Thr Ala Ser Gly Gln Tyr Gly Gln Trp Ala Pro
    1160                1165                1170

Lys Leu Ala Arg Leu His Tyr Ser Gly Ser Ile Asn Ala Trp Ser
    1175                1180                1185

Thr Lys Glu Pro Phe Ser Trp Ile Lys Val Asp Leu Leu Ala Pro
    1190                1195                1200

Met Ile Ile His Gly Ile Lys Thr Gln Gly Ala Arg Gln Lys Phe
    1205                1210                1215

Ser Ser Leu Tyr Ile Ser Gln Phe Ile Ile Met Tyr Ser Leu Asp
    1220                1225                1230

Gly Lys Lys Trp Gln Thr Tyr Arg Gly Asn Ser Thr Gly Thr Leu
    1235                1240                1245

Met Val Phe Phe Gly Asn Val Asp Ser Ser Gly Ile Lys His Asn
    1250                1255                1260

Ile Phe Asn Pro Pro Ile Ile Ala Arg Tyr Ile Arg Leu His Pro
    1265                1270                1275

Thr His Tyr Ser Ile Arg Ser Thr Leu Arg Met Glu Leu Met Gly
    1280                1285                1290

Cys Asp Leu Asn Ser Cys Ser Met Pro Leu Gly Met Glu Ser Lys
    1295                1300                1305

Ala Ile Ser Asp Ala Gln Ile Thr Ala Ser Ser Tyr Phe Thr Asn
    1310                1315                1320

Met Phe Ala Thr Trp Ser Pro Ser Lys Ala Arg Leu His Leu Gln
    1325                1330                1335

Gly Arg Ser Asn Ala Trp Arg Pro Gln Val Asn Asn Pro Lys Glu
    1340                1345                1350

Trp Leu Gln Val Asp Phe Gln Lys Thr Met Lys Val Thr Gly Val
    1355                1360                1365

Thr Thr Gln Gly Val Lys Ser Leu Leu Thr Ser Met Tyr Val Lys
    1370                1375                1380

Glu Phe Leu Ile Ser Ser Ser Gln Asp Gly His Gln Trp Thr Leu
    1385                1390                1395

Phe Phe Gln Asn Gly Lys Val Lys Val Phe Gln Gly Asn Gln Asp
    1400                1405                1410

Ser Phe Thr Pro Val Val Asn Ser Leu Asp Pro Pro Leu Leu Thr
    1415                1420                1425

Arg Tyr Leu Arg Ile His Pro Gln Ser Trp Val His Gln Ile Ala
    1430                1435                1440

Leu Arg Met Glu Val Leu Gly Cys Glu Ala Gln Asp Leu Tyr
    1445                1450                1455

<210> SEQ ID NO 4
<211> LENGTH: 34
<212> TYPE: DNA
<213> ORGANISM: Artificial Sequence
<220> FEATURE:
<223> OTHER INFORMATION: constructed sequence

<400> SEQUENCE: 4
tgtttgctgc ttgcaatgtt tgcccatttt aggg                            34

<210> SEQ ID NO 5
<211> LENGTH: 100
<212> TYPE: DNA
```

<213> ORGANISM: Artificial Sequence
<220> FEATURE:
<223> OTHER INFORMATION: constructed sequence

<400> SEQUENCE: 5
ctacctcgtg atcgcccggc ccctgttcaa acatgtccta atactctgtc tctgcaaggg    60
tcatcagtag ttttccatct tactcaacat cctcccagtg                         100

<210> SEQ ID NO 6
<211> LENGTH: 42
<212> TYPE: DNA
<213> ORGANISM: Artificial Sequence
<220> FEATURE:
<223> OTHER INFORMATION: constructed sequence

<400> SEQUENCE: 6
aggttaattt ttaaactgtt tgctctggtt aataatctca gg                       42

<210> SEQ ID NO 7
<211> LENGTH: 190
<212> TYPE: DNA
<213> ORGANISM: Artificial Sequence
<220> FEATURE:
<223> OTHER INFORMATION: constructed sequence

<400> SEQUENCE: 7
atttcataga acgaatgttc cgatgctcta atctctctag acaaggttca tatttgtatg    60
ggttacttat tctctctttg ttgactaagt caataatcag aatcagcagg tttgcagtca   120
gattggcagg gataagcagc ctagctcagg agaagtgagt ataaaagccc caggctggga   180
gcagccatca                                                          190

<210> SEQ ID NO 8
<211> LENGTH: 176
<212> TYPE: DNA
<213> ORGANISM: Artificial Sequence
<220> FEATURE:
<223> OTHER INFORMATION: constructed sequence

<400> SEQUENCE: 8
actcaaagtt caaaccttat catttttgc tttgttcctc ttggccttgg ttttgtacat     60
cagctttgaa ataccatcc cagggttaat gctggggtta atttataact aagagtgctc   120
tagttttgca atacaggaca tgctataaaa atggaaagat gttgctttct gagaga        176

<210> SEQ ID NO 9
<211> LENGTH: 218
<212> TYPE: DNA
<213> ORGANISM: Artificial Sequence
<220> FEATURE:
<223> OTHER INFORMATION: constructed sequence

<400> SEQUENCE: 9
tggacacagg acgctgtggt ttctgagcca gggggcgact cagatcccag ccagtggact    60
tagcccctgt ttgctcctcc gataactggg gtgaccttgg ttaatattca ccagcagcct   120
cccccgttgc ccctctggat ccactgctta aatacgacg aggacagggc cctgtctcct    180
cagcttcagg caccaccact gacctgggac agtgaata                            218

<210> SEQ ID NO 10
<211> LENGTH: 75
<212> TYPE: DNA
<213> ORGANISM: Artificial Sequence

```
<220> FEATURE:
<223> OTHER INFORMATION: constructed sequence

<400> SEQUENCE: 10
aataaagtct gagtgggcgg cagcctgtgt gtgcctgggt tctctctgtc ccggaatgtg      60
caaacaatgg aggtg                                                      75

<210> SEQ ID NO 11
<211> LENGTH: 168
<212> TYPE: DNA
<213> ORGANISM: Artificial Sequence
<220> FEATURE:
<223> OTHER INFORMATION: constructed sequence

<400> SEQUENCE: 11
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact    120
aggggttcct tgtagttaat gattaacccg ccatgctact tatctact                 168

<210> SEQ ID NO 12
<211> LENGTH: 164
<212> TYPE: DNA
<213> ORGANISM: Artificial Sequence
<220> FEATURE:
<223> OTHER INFORMATION: constructed sequence

<400> SEQUENCE: 12
gataagtagc atggcgggtt aatcattaac tacaaggaac ccctagtgat ggagttggcc      60
actccctctc tgcgcgctcg ctcgctcact gaggccgggc gaccaaaggt cgcccgacgc    120
ccgggctttg cccgggcggc ctcagtgagc gagcgagcgc gcag                     164

<210> SEQ ID NO 13
<211> LENGTH: 7920
<212> TYPE: DNA
<213> ORGANISM: Artificial Sequence
<220> FEATURE:
<223> OTHER INFORMATION: constructed sequence

<400> SEQUENCE: 13
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact    120
aggggttcct tgtagttaat gattaacccg ccatgctact tatctactta agctacctcg    180
tgatcgcccg gccctgttc aaacatgtcc taatactctg tctctgcaag ggtcatcagt    240
agttttccat cttactcaac atcctcccag tggaattcat ttcatagaac gaatgttccg    300
atgctctaat ctctctagac aaggttcata tttgtatggg ttacttattc tctctttgtt    360
gactaagtca ataatcagaa tcagcaggtt tgcagtcaga ttggcaggga taagcagcct    420
agctcaggag aagtgagtat aaaagcccca ggctgggagc agccatcagc ggccgccacc    480
atgcagatcg agctgagcac ctgcttcttc ctgtgcctgc tgcggttctg cttctccgcc    540
acccggcggt actacctggg agccgtggag ctgagctggg attacatgca gagcgatctg    600
ggagagctgc cagtggatgc ccggttccca ccacgggtgc caaagagctt cccattcaac    660
accagcgtgg tgtacaagaa gaccctgttc gtggagttca ccgatcacct gttcaacatc    720
gccaagccac ggccacctg gatgggactg ctgggaccaa ccatccaggc cgaggtgtac    780
gataccgtgg tgatcaccct gaagaacatg gcctctcatc ctgtgtccct gcacgccgtg    840
```

```
ggagtgagct actggaaggc cagcgaggga gccgagtacg atgatcagac cagccagcgg      900
gagaaggagg atgataaggt gttcccagga ggaagccaca cctacgtgtg gcaggtgctg      960
aaggagaacg gaccaatggc cagcgatcca ctgtgcctga cctacagcta cctgagccac     1020
gtggatctgg tgaaggatct gaacagcgga ctgatcggag ccctgctggt gtgccgggag     1080
ggaagcctgg ccaaggagaa gacccagacc ctgcacaagt tcatcctgct gttcgccgtg     1140
ttcgatgagg gaaagagctg gcacagcgag accaagaaca gcctgatgca ggatcgggat     1200
gccgccagcg cccgggcctg gccaaagatg cacaccgtga acggatacgt gaaccggagc     1260
ctgccaggac tgatcggatg ccaccggaag agcgtgtact ggcacgtgat cggaatggga     1320 accacccag aggtgcactc tatcttcctg gagggacaca cctttctggt gcggaaccac     1380
cggcaggcca gcctggagat cagcccaatc accttcctga ccgcccagac cctgctgatg     1440
gatctgggac agttcctgct gttctgccat atcagcagcc accagcacga tggaatggag     1500
gcctacgtga aggtggatag ctgcccagag gagccacagc tgcggatgaa gaacaacgag     1560
gaggccgagg attacgatga tgatctgacc gatagcgaga tggatgtggt gcggttcgat     1620
gatgataaca gcccaagctt catccagatc cggagcgtgg ccaagaagca cccaaagacc     1680
tgggtgcact acatcgccgc cgaggaggag gattgggatt acgccccact ggtgctggcc     1740
cctgatgatc ggagctacaa gagccagtac ctgaacaacg gaccacagcg gatcggacgg     1800
aagtacaaaa aagtgcggtt catggcctac accgatgaga ccttcaagac ccgggaggcc     1860
atccagcacg agagcggaat cctgggacca ctgctgtacg agaggtggg agatacctg      1920 ctgatcatct tcaagaacca ggccagccgg ccatacaaca tctacccaca cggaatcacc     1980
gatgtgcggc cactgtacag ccggcggctg ccaaagggag tgaagcacct gaaggatttc     2040
ccaatcctgc caggagagat cttcaagtac aagtggacag tgacagtgga ggatggacca     2100
accaagtctg atccaagatg cctgaccaga tactacagca gctttgtgaa catggagaga     2160
gacctggcct ctggactgat tggaccactg ctgatctgct acaaggagtc tgtggatcag     2220
agaggaaacc agatcatgtc tgataagaga aatgtgatcc tgttctctgt gtttgatgag     2280
aacagaagct ggtacctgac agagaacatc cagagattcc tgccaaaccc agccggagtg     2340
cagctggagg atccagagtt ccaggccagc aacatcatgc acagcatcaa cggatacgtg     2400
ttcgatagcc tgcagctgag cgtgtgcctg cacgaggtgg cctattggta tatcctgagc     2460
atcggagccc agaccgattt cctgagcgtg ttcttcagcg atacaccctt caagcacaag     2520
atggtgtacg aggatacccct gaccctgttc ccattctccg gagagaccgt gttcatgagc     2580
atggagaacc caggactgtg gatcctggga tgccacaact ctgatttcag aaacagagga     2640
atgactgccc tgctgaaagt gtccagctgt gataagaaca ctggagatta ctatgaggat     2700
agctatgagg atatctctgc ctacctgctg agcaagaaca atgccattga gccaagaagc     2760
ttcagccaga acccaccagt gctgaagaga caccagagag agatcaccag aaccaccctg     2820
cagtctgatc aggaggagat tgattatgat gataccatct ctgtggagat gaagaaggag     2880
gattttgata tctatgatga ggatgagaac cagagcccaa gaagcttcca gaagaagacc     2940
agacactact tcatcgctgc agtggagaga ctgtgggatt atggaatgag cagcagccca     3000
cacgtgctga aaacagagc ccagagcgga tctgtgccac agttcaagaa ggtggtgttc     3060
caggagttca ccgatggaag cttcacccag ccactgtacc ggggagagct gaacgagcac     3120
ctgggactgc tgggaccata catccggggcc gaggtggagg ataacatcat ggtgaccttc     3180
cggaaccagg ccagccggcc atacagcttc tacagcagcc tgatcagcta cgaggaggat     3240
```

```
cagcggcagg gagccgagcc acggaagaac ttcgtgaagc caaacgagac caagacctac    3300
ttctggaagg tgcagcacca catggcccca accaaggatg agttcgattg caaggcctgg    3360
gcctacttca gcgatgtgga tctggagaag gatgtgcaca gcggactgat cggaccactg    3420
ctggtgtgcc acaccaacac cctgaaccca gcccacggac ggcaggtgac cgtgcaggag    3480
ttcgccctgt tcttcaccat cttcgatgag accaagagct ggtacttcac cgagaacatg    3540
gagcggaact gccgggcccc ttgcaacatc cagatggagg atccaacctt caaggagaac    3600
taccggttcc acgccatcaa cggatacatc atggataccc tgccaggact ggtgatggcc    3660
caggatcagc ggatccggtg gtacctgctg agcatgggaa gcaacgagaa catccacagc    3720
atccacttca gcggacacgt gttcaccgtg cggaagaagg aggagtacaa gatggccctg    3780
tacaacctgt acccaggagt gttcgagacc gtggagatgc tgccaagcaa ggccggaatc    3840
tggcgggtgg agtgcctgat cggagagcac ctgcacgccg aatgagcac cctgttcctg    3900 gtgtacagca caagtgcca gaccccactg ggaatggcca gcggacacat ccgggatttc    3960
cagatcaccg ccagcggaca gtacggacag tgggccccaa agctggcccg gctgcactac    4020
agcggaagca tcaacgcctg gagcaccaag gagccattca gctggatcaa agtggatctg    4080
ctggccccaa tgatcatcca cggaatcaag acccaggag cccggcagaa gttcagcagc    4140
ctgtacatca gccagttcat catcatgtac agcctggatg aaagaagtg gcagacctac    4200 cggggaaaca gcaccggaac cctgatggtg ttcttcggaa acgtggatag cagcggaatc    4260
aagcacaaca tcttcaaccc accaatcatc gcccgataca tccggctgca cccaaccca    4320 tacagcatca gaagcaccct gcggatggag ctgatgggat gtgatctgaa cagctgctcc    4380
atgccactgg gaatggagag caaggccatc agcgatgccc agatcaccgc cagcagctac    4440
ttcaccaaca tgttcgccac ctggagccca agcaaggccc ggctgcacct gcagggacgg    4500
agcaacgcct ggcggccaca ggtgaataac ccaaaggagt ggctgcaggt ggatttccag    4560
aagaccatga aggtgaccgg agtgaccacc cagggagtga agagcctgct gactagcatg    4620
tatgtgaagg agttcctgat cagcagcagc caggatggac accagtggac cctgttcttc    4680
cagaacggaa aggtgaaggt gttccaggga aaccaggata gcttcacccc agtggtgaac    4740
agcctggatc caccactgct gacccgatac ctgcggatcc acccacagag ctgggtgcac    4800
cagatcgccc tgagaatgga ggtgctggga tgcgaggccc aggatctgta ctgatgagca    4860
tgcaataaag tctgagtggg cggcagcctg tgtgtgcctg ggttctctct gtcccggaat    4920
gtgcaaacaa tggaggtgct cgagtagata agtagcatgg cgggttaatc attaactaca    4980
aggaacccct agtgatggag ttggccactc cctctctgcg cgctcgctcg ctcactgagg    5040
ccgggcgacc aaaggtcgcc cgacgcccgg gctttgcccg gcggcctca gtgagcgagc    5100 gagcgcgcag ccttaattaa cctaattcac tggccgtcgt tttacaacgt cgtgactggg    5160
aaaaccctgg cgttacccaa cttaatcgcc ttgcagcaca tccccctttc gccagctggc    5220
gtaatagcga agaggcccgc accgatcgcc cttcccaaca gttgcgcagc ctgaatggcg    5280
aatgggacgc gccctgtagc ggcgcattaa gcgcggcggg tgtggtggtt acgcgcagcg    5340
tgaccgctac acttgccagc gccctagcgc ccgctccttt cgctttcttc ccttcctttc    5400
tcgccacgtt cgccggcttt ccccgtcaag ctctaaatcg gggctccct ttagggttcc    5460 gatttagtgc tttacggcac ctcgacccca aaaaacttga ttagggtgat ggttcacgta    5520
gtgggccatc gccctgatag acggtttttc gccctttgac gttggagtcc acgttcttta    5580
```

```
atagtggact cttgttccaa actggaacaa cactcaaccc tatctcggtc tattcttttg    5640
atttataagg gattttgccg atttcggcct attggttaaa aaatgagctg atttaacaaa    5700
aatttaacgc gaattttaac aaaatattaa cgcttacaat ttaggtggca cttttcgggg    5760
aaatgtgcgc ggaacccta tttgtttatt tttctaaata cattcaaata tgtatccgct    5820
catgagacaa taaccctgat aaatgcttca ataatattga aaaggaaga gtatgagtat    5880
tcaacatttc cgtgtcgccc ttattccctt ttttgcggca ttttgccttc ctgttttgc    5940
tcacccagaa acgctggtga agtaaaaga tgctgaagat cagttgggtg cacgagtggg    6000
ttacatcgaa ctggatctca acagcggtaa gatccttgag agttttcgcc ccgaagaacg    6060
ttttccaatg atgagcactt ttaaagttct gctatgtggc gcggtattat cccgtattga    6120
cgccgggcaa gagcaactcg gtcgccgcat acactattct cagaatgact tggttgagta    6180
ctcaccagtc acagaaaagc atcttacgga tggcatgaca gtaagagaat tatgcagtgc    6240
tgccataacc atgagtgata acactgcggc caacttactt ctgacaacga tcggaggacc    6300
gaaggagcta accgcttttt tgcacaacat gggggatcat gtaactcgcc ttgatcgttg    6360
ggaaccggag ctgaatgaag ccataccaaa cgacgagcgt gacaccacga tgcctgtagc    6420
aatggcaaca acgttgcgca aactattaac tggcgaacta cttactctag cttcccggca    6480
acaattaata gactggatgg aggcggataa agttgcagga ccacttctgc gctcggccct    6540
tccggctggc tggtttattg ctgataaatc tggagccggt gagcgtgggt ctcgcggtat    6600
cattgcagca ctggggccag atggtaagcc ctcccgtatc gtagttatct acacgacggg    6660
gagtcaggca actatggatg aacgaaatag acagatcgct gagataggtg cctcactgat    6720
taagcattgg taactgtcag accaagttta ctcatatata ctttagattg atttaaaact    6780
tcattttaa tttaaaagga tctaggtgaa gatcctttt gataatctca tgaccaaaat    6840
cccttaacgt gagttttcgt tccactgagc gtcagacccc gtagaaaaga tcaaaggatc    6900
ttcttgagat cctttttttc tgcgcgtaat ctgctgcttg caaacaaaaa aaccaccgct    6960
accagcggtg gtttgtttgc cggatcaaga gctaccaact cttttccga aggtaactgg    7020
cttcagcaga gcgcagatac caaatactgt tcttctagtg tagccgtagt taggccacca    7080
cttcaagaac tctgtagcac cgcctacata cctcgctctg ctaatcctgt taccagtggc    7140
tgctgccagt ggcgataagt cgtgtcttac cgggttggac tcaagacgat agttaccgga    7200
taaggcgcag cggtcgggct gaacggggg ttcgtgcaca cagcccagct tggagcgaac    7260
gacctacacc gaactgagat acctacagcg tgagctatga gaaagcgcca cgcttcccga    7320
agggagaaag gcggacaggt atccggtaag cggcagggtc ggaacaggag agcgcacgag    7380
ggagcttcca gggggaaacg cctggtatct ttatagtcct gtcgggtttc gccacctctg    7440
acttgagcgt cgatttttgt gatgctcgtc aggggggcgg agcctatgga aaaacgccag    7500
caacgcggcc tttttacggt tcctggcctt ttgctggcct tttgctcaca tgttctttcc    7560
tgcgttatcc cctgattctg tggataaccg tattaccgcc tttgagtgag ctgataccgc    7620
tcgccgcagc cgaacgaccg agcgcagcga gtcagtgagc gaggaagcgg aagagcgccc    7680
aatacgcaaa ccgcctctcc ccgcgcgttg gccgattcat taatgcagct ggcacgacag    7740
gtttcccgac tggaaagcgg gcagtgagcg caacgcaatt aatgtgagtt agctcactca    7800
ttaggcaccc caggctttac actttatgct tccggctcgt atgttgtgtg gaattgtgag    7860
cggataacaa tttcacacag gaaacagcta tgaccatgat tacgccagat ttaattaagg    7920
```

<210> SEQ ID NO 14
<211> LENGTH: 8004
<212> TYPE: DNA
<213> ORGANISM: Artificial Sequence
<220> FEATURE:
<223> OTHER INFORMATION: constructed sequence

<400> SEQUENCE: 14

| | | | | | |
|---|---|---|---|---|---|
| ctgcgcgctc | gctcgctcac | tgaggccgcc | cgggcaaagc | ccgggcgtcg | ggcgaccttt | 60 |
| ggtcgcccgg | cctcagtgag | cgagcgagcg | cgcagagagg | gagtggccaa | ctccatcact | 120 |
| aggggttcct | tgtagttaat | gattaacccg | ccatgctact | tatctactta | agctacctcg | 180 |
| tgatcgcccg | gccctgttc | aaacatgtcc | taatactctg | tctctgcaag | ggtcatcagt | 240 |
| agttttccat | cttactcaac | atcctcccag | tgaggttaat | ttttaaactg | tttgctctgg | 300 |
| ttaataatct | caggaggtta | atttttaaac | tgtttgctct | ggttaataat | ctcagggaat | 360 |
| tcatttcata | gaacgaatgt | tccgatgctc | taatctctct | agacaaggtt | catatttgta | 420 |
| tgggttactt | attctctctt | tgttgactaa | gtcaataatc | agaatcagca | ggtttgcagt | 480 |
| cagattggca | gggataagca | gcctagctca | ggagaagtga | gtataaaagc | cccaggctgg | 540 |
| gagcagccat | cagcggccgc | caccatgcag | atcgagctga | gcacctgctt | cttcctgtgc | 600 |
| ctgctgcggt | tctgcttctc | cgccacccgg | cggtactacc | tgggagccgt | ggagctgagc | 660 |
| tgggattaca | tgcagagcga | tctgggagag | ctgccagtgg | atgcccggtt | cccaccacgg | 720 |
| gtgccaaaga | gcttcccatt | caacaccagc | gtggtgtaca | gaagaccct | gttcgtggag | 780 |
| ttcaccgatc | acctgttcaa | catcgccaag | ccacggccac | cctggatggg | actgctggga | 840 |
| ccaaccatcc | aggccgaggt | gtacgatacc | gtggtgatca | ccctgaagaa | catggcctct | 900 |
| catcctgtgt | ccctgcacgc | cgtgggagtg | agctactgga | aggccagcga | gggagccgag | 960 |
| tacgatgatc | agaccagcca | gcgggagaag | gaggatgata | aggtgttccc | aggaggaagc | 1020 |
| cacacctacg | tgtggcaggt | gctgaaggag | aacggaccaa | tggccagcga | tccactgtgc | 1080 |
| ctgacctaca | gctacctgag | ccacgtggat | ctggtgaagg | atctgaacag | cggactgatc | 1140 |
| ggagccctgc | tggtgtgccg | ggagggaagc | ctggccaagg | agaagaccca | gaccctgcac | 1200 |
| aagttcatcc | tgctgttcgc | cgtgttcgat | gagggaaaga | gctggcacag | cgagaccaag | 1260 |
| aacagcctga | tgcaggatcg | ggatgccgcc | agcgcccggg | cctggccaaa | gatgcacacc | 1320 |
| gtgaacggat | acgtgaaccg | gagcctgcca | ggactgatcg | gatgccaccg | gaagagcgtg | 1380 |
| tactggcacg | tgatcggaat | gggaaccacc | ccagaggtgc | actctatctt | cctggaggga | 1440 |
| cacaccttc | tggtgcggaa | ccaccggcag | gccagcctgg | agatcagccc | aatcaccttc | 1500 |
| ctgaccgccc | agaccctgct | gatggatctg | gacagttcc | tgctgttctg | ccatatcagc | 1560 |
| agccaccagc | acgatggaat | ggaggcctac | gtgaaggtgg | atagctgccc | agaggagcca | 1620 |
| cagctgcgga | tgaagaacaa | cgaggaggcc | gaggattacg | atgatgatct | gaccgatagc | 1680 |
| gagatggatg | tggtgcggtt | cgatgatgat | aacagcccaa | gcttcatcca | gatccggagc | 1740 |
| gtggccaaga | agcaccccaa | gacctggtg | cactacatcg | ccgccgagga | ggaggattgg | 1800 |
| gattacgccc | cactggtgct | ggcccctgat | gatcggagct | acaagagcca | gtacctgaac | 1860 |
| aacggaccac | agcggatcgg | acggaagtac | aaaaaagtgc | ggttcatggc | ctacaccgat | 1920 |
| gagaccttca | agacccggga | ggccatccag | cacgagagcg | gaatcctggg | accactgctg | 1980 |
| tacgagagg | tgggagatac | cctgctgatc | atcttcaaga | accaggccag | ccggccatac | 2040 |
| aacatctacc | cacacggaat | caccgatgtg | cggccactgt | acagccggcg | gctgccaaag | 2100 |

```
ggagtgaagc acctgaagga tttcccaatc ctgccaggag agatcttcaa gtacaagtgg    2160
acagtgacag tggaggatgg accaaccaag tctgatccaa gatgcctgac cagatactac    2220
agcagctttg tgaacatgga gagagacctg gcctctggac tgattggacc actgctgatc    2280
tgctacaagg agtctgtgga tcagagagga accagatca tgtctgataa agaaaatgtg    2340
atcctgttct ctgtgtttga tgagaacaga agctggtacc tgacagagaa catccagaga    2400
ttcctgccaa acccagccgg agtgcagctg gaggatccag agttccaggc cagcaacatc    2460
atgcacagca tcaacggata cgtgttcgat agcctgcagc tgagcgtgtg cctgcacgag    2520
gtggcctatt ggtatatcct gagcatcgga gcccagaccg atttcctgag cgtgttcttc    2580
agcggataca ccttcaagca aagatggtg tacgaggata ccctgaccct gttcccattc    2640
tccggagaga ccgtgttcat gagcatgag aacccaggac tgtggatcct gggatgccac    2700
aactctgatt tcagaaacag aggaatgact gccctgctga agtgtccag ctgtgataag    2760 aacactggag attactatga ggatagctat gaggatatct ctgcctacct gctgagcaag    2820
aacaatgcca ttgagccaag aagcttcagc cagaacccac cagtgctgaa gagacaccag    2880
agagagatca ccagaaccac cctgcagtct gatcaggagg agattgatta tgatgatacc    2940
atctctgtgg agatgaagaa ggaggatttt gatatctatg atgaggatga aaccagagc    3000 ccaagaagct tccagaagaa gaccagacac tacttcatcg ctgcagtgga gagactgtgg    3060
gattatggaa tgagcagcag cccacacgtg ctgagaaaca gagcccagag cggatctgtg    3120
ccacagttca gaaggtggt gttccaggag ttcaccgatg aagcttcac ccagccactg    3180 taccggggag agctgaacga gcacctggga ctgctgggac atacatccg ggccgaggtg    3240 gaggataaca tcatggtgac cttccggaac caggccagcc ggccatacag cttctacagc    3300
agcctgatca gctacgagga ggatcagcgg cagggagccg agccacggaa gaacttcgtg    3360
aagccaaacg agaccaagac ctacttctgg aaggtgcagc accacatggc cccaaccaag    3420
gatgagttcg attgcaaggc ctgggcctac ttcagcgatg tggatctgga aggatgtg    3480 cacagcggac tgatcggacc actgctggtg tgccacacca acacctgaa cccagcccac    3540 ggacggcagg tgaccgtgca ggagttcgcc ctgttcttca ccatcttcga tgagaccaag    3600
agctggtact tcaccgagaa catggagcgg aactgccggg cccctgcaa catccagatg    3660 gaggatccaa ccttcaagga gaactaccgg ttccacgcca tcaacggata catcatggat    3720
accctgccag gactggtgat ggcccaggat cagcggatcc ggtggtacct gctgagcatg    3780
ggaagcaacg agaacatcca cagcatccac ttcagcggac acgtgttcac cgtgcggaag    3840
aaggaggagt acaagatggc cctgtacaac ctgtacccag agtgttcga gaccgtggag    3900 atgctgccaa gcaaggccgg aatctggcgg gtggagtgcc tgatcggaga gcacctgcac    3960
gccggaatga gcacctgtt cctggtgtac agcaacaagt gccagacccc actgggaatg    4020
gccagcggac acatccggga tttccagatc accgccagcg acagtacgg acagtgggcc    4080 ccaaagctgg cccggctgca ctacagcgga agcatcaacg cctggagcac caaggagcca    4140
ttcagctgga tcaaagtgga tctgctggcc ccaatgatca tccacggaat caagacccag    4200
ggagcccggc agaagttcag cagcctgtac atcagccagt tcatcatcat gtacagcctg    4260
gatggaaaga agtggcagac ctaccggga aacagcaccg gaaccctgat ggtgttcttc    4320
ggaaacgtgg atagcagcgg aatcaagcac aacatcttca acccaccaat catcgcccga    4380
tacatccggc tgcaccccaa ccactacagc atcagaagca cctgcgat ggagctgatg    4440 ggatgtgatc tgaacagctg ctccatgcca ctgggaatgg agagcaaggc catcagcgat    4500
```

```
gcccagatca ccgccagcag ctacttcacc aacatgttcg ccacctggag cccaagcaag    4560
gcccggctgc acctgcaggg acggagcaac gcctggcggc acaggtgaa taacccaaag    4620
gagtggctgc aggtggattt ccagaagacc atgaaggtga ccggagtgac cacccaggga    4680
gtgaagagcc tgctgactag catgtatgtg aaggagttcc tgatcagcag cagccaggat    4740
ggacaccagt ggaccctgtt cttccagaac ggaaaggtga aggtgttcca gggaaaccag    4800
gatagcttca ccccagtggt gaacagcctg atccaccac tgctgacccg atacctgcgg    4860
atccacccac agagctgggt gcaccagatc gccctgagaa tggaggtgct gggatgcgag    4920
gcccaggatc tgtactgatg agcatgcaat aaagtctgag tgggcggcag cctgtgtgtg    4980
cctgggttct ctctgtcccg gaatgtgcaa acaatggagg tgctcgagta gataagtagc    5040
atggcgggtt aatcattaac tacaaggaac ccctagtgat ggagttggcc actccctctc    5100
tgcgcgctcg ctcgctcact gaggccgggc gaccaaaggt cgcccgacgc ccgggctttg    5160
cccgggcggc ctcagtgagc gagcgagcgc gcagccttaa ttaacctaat tcactggccg    5220
tcgttttaca acgtcgtgac tgggaaaacc ctggcgttac ccaacttaat cgccttgcag    5280
cacatccccc tttcgccagc tggcgtaata gcgaagaggc ccgcaccgat cgcccttccc    5340
aacagttgcg cagcctgaat ggcgaatggg acgcgccctg tagcggcgca ttaagcgcgg    5400
cgggtgtggt ggttacgcgc agcgtgaccg ctacacttgc cagcgcccta gcgcccgctc    5460
ctttcgcttt cttcccttcc tttctcgcca cgttcgccgg ctttccccgt caagctctaa    5520
atcgggggct ccctttaggg ttccgattta gtgctttacg gcacctcgac cccaaaaaac    5580
ttgattaggg tgatggttca cgtagtgggc catcgccctg atagacggtt tttcgccctt    5640
tgacgttgga gtccacgttc tttaatagtg actcttgtt ccaaactgga acaacactca    5700
accctatctc ggtctattct tttgatttat aagggatttt gccgatttcg gcctattggt    5760
taaaaaatga gctgatttaa caaaaattta acgcgaattt taacaaaata ttaacgctta    5820
caatttaggt ggcacttttc ggggaaatgt gcgcggaacc cctatttgtt tatttttcta    5880
aatacattca aatatgtatc cgctcatgag acaataaccc tgataaatgc ttcaataata    5940
ttgaaaaagg aagagtatga gtattcaaca tttccgtgtc gcccttattc cctttttgc    6000
ggcattttgc cttcctgttt ttgctcaccc agaaacgctg gtgaaagtaa aagatgctga    6060
agatcagttg ggtgcacgag tgggttacat cgaactggat ctcaacagcg gtaagatcct    6120
tgagagtttt cgccccgaag aacgttttcc aatgatgagc acttttaaag ttctgctatg    6180
tggcgcggta ttatcccgta ttgacgccgg gcaagagcaa ctcggtcgcc gcatacacta    6240
ttctcagaat gacttggttg agtactcacc agtcacagaa aagcatctta cggatggcat    6300
gacagtaaga gaattatgca gtgctgccat aaccatgagt gataacactg cggccaactt    6360
acttctgaca acgatcggag gaccgaagga gctaaccgct tttttgcaca acatggggga    6420
tcatgtaact cgccttgatc gttgggaacc ggagctgaat gaagccatac caaacgacga    6480
gcgtgacacc acgatgcctg tagcaatggc aacaacgttg cgcaaactat taactggcga    6540
actacttact ctagcttccc ggcaacaatt aatagactgg atggaggcgg ataaagttgc    6600
aggaccactt ctgcgctcgg cccttccggc tggctggttt attgctgata atctggagc    6660
cggtgagcgt gggtctcgcg gtatcattgc agcactgggg ccagatggta agccctcccg    6720
tatcgtagtt atctacacga cggggagtca ggcaactatg gatgaacgaa atagacagat    6780
cgctgagata ggtgcctcac tgattaagca ttggtaactg tcagaccaag tttactcata    6840
```

| | |
|---|---|
| tatactttag attgatttaa aacttcattt ttaatttaaa aggatctagg tgaagatcct | 6900 |
| ttttgataat ctcatgacca aaatccctta acgtgagttt tcgttccact gagcgtcaga | 6960 |
| ccccgtagaa aagatcaaag gatcttcttg atccttttt tttctgcgcg taatctgctg | 7020 |
| cttgcaaaca aaaaaaccac cgctaccagc ggtggtttgt ttgccggatc aagagctacc | 7080 |
| aactctttt ccgaaggtaa ctggcttcag cagagcgcag ataccaaata ctgttcttct | 7140 |
| agtgtagccg tagttaggcc accacttcaa gaactctgta gcaccgccta catacctcgc | 7200 |
| tctgctaatc ctgttaccag tggctgctgc cagtggcgat aagtcgtgtc ttaccgggtt | 7260 |
| ggactcaaga cgatagttac cggataaggc gcagcggtcg ggctgaacgg ggggttcgtg | 7320 |
| cacacagccc agcttggagc gaacgaccta caccgaactg agatacctac agcgtgagct | 7380 |
| atgagaaagc gccacgcttc ccgaagggag aaaggcggac aggtatccgg taagcggcag | 7440 |
| ggtcggaaca ggagagcgca cgagggagct tccagggga aacgcctggt atctttatag | 7500 |
| tcctgtcggg tttcgccacc tctgacttga gcgtcgattt ttgtgatgct cgtcaggggg | 7560 |
| gcggagccta tggaaaaacg ccagcaacgc ggcctttta cggttcctgg ccttttgctg | 7620 |
| gccttttgct cacatgttct ttcctgcgtt atccctgat tctgtggata accgtattac | 7680 |
| cgcctttgag tgagctgata ccgctcgccg cagccgaacg accgagcgca gcgagtcagt | 7740 |
| gagcgaggaa gcggaagagc gcccaatacg caaaccgcct ctccccgcgc gttggccgat | 7800 |
| tcattaatgc agctggcacg acaggtttcc cgactgaaa gcgggcagtg agcgcaacgc | 7860 |
| aattaatgtg agttagctca ctcattaggc accccaggct ttacacttta tgcttccggc | 7920 |
| tcgtatgttg tgtggaattg tgagcggata acaatttcac acaggaaaca gctatgacca | 7980 |
| tgattacgcc agatttaatt aagg | 8004 |

<210> SEQ ID NO 15
<211> LENGTH: 7948
<212> TYPE: DNA
<213> ORGANISM: Artificial Sequence
<220> FEATURE:
<223> OTHER INFORMATION: constructed sequence

<400> SEQUENCE: 15

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| aggggttcct tgtagttaat gattaacccg ccatgctact tatctactta agctacctcg | 180 |
| tgatcgcccg gccctgttc aaacatgtcc taatactctg tctctgcaag ggtcatcagt | 240 |
| agttttccat cttactcaac atcctcccag tggaattctg gacacaggac gctgtggttt | 300 |
| ctgagccagg gggcgactca gatcccagcc agtggactta gcccctgttt gctcctccga | 360 |
| taactggggt gaccttggtt aatattcacc agcagcctcc cccgttgccc ctctggatcc | 420 |
| actgcttaaa tacggacgag gacagggccc tgtctcctca gcttcaggca ccaccactga | 480 |
| cctgggacag tgaatagcgg ccgccaccat gcagatcgag ctgagcacct gcttcttcct | 540 |
| gtgcctgctg cggttctgct tctccgccac ccggcggtac tacctgggag ccgtggagct | 600 |
| gagctgggat tacatgcaga gcgatctggg agagctgcca gtggatgccc ggttcccacc | 660 |
| acgggtgcca aagagcttcc cattcaacac cagcgtggtg tacaagaaga ccctgttcgt | 720 |
| ggagttcacc gatcacctgt tcaacatcgc caagccacgg ccaccctgga tgggactgct | 780 |
| gggaccaacc atccaggccg aggtgtacga taccgtggtg atcaccctga gaacatggc | 840 |
| ctctcatcct gtgtccctgc acgccgtggg agtgagctac tggaaggcca gcgagggagc | 900 |

-continued

```
cgagtacgat gatcagacca gccagcggga gaaggaggat gataaggtgt tcccaggagg    960
aagccacacc tacgtgtggc aggtgctgaa ggagaacgga ccaatggcca gcgatccact   1020
gtgcctgacc tacagctacc tgagccacgt ggatctggtg aaggatctga cagcggact   1080
gatcggagcc ctgctggtgt gccgggaggg aagcctggcc aaggagaaga cccagaccct   1140
gcacaagttc atcctgctgt tcgccgtgtt cgatgaggga aagagctggc acagcgagac   1200
caagaacagc ctgatgcagg atcgggatgc cgccagcgcc cgggcctggc aaagatgca    1260
caccgtgaac ggatacgtga accggagcct gccaggactg atcggatgcc accggaagag   1320
cgtgtactgg cacgtgatcg gaatgggaac cacccagag gtgcactcta tcttcctgga   1380
gggacacacc tttctggtgc ggaaccaccg gcaggccagc ctggagatca gcccaatcac   1440
cttcctgacc gcccagaccc tgctgatgga tctgggacag ttcctgctgt tctgccatat   1500
cagcagccac cagcacgatg gaatggaggc ctacgtgaag gtggatagct gcccagagga   1560
gccacagctg cggatgaaga caacgagga ggccgaggat tacgatgatg atctgaccga   1620
tagcgagatg gatgtggtgc ggttcgatga tgataacagc ccaagcttca tccagatccg   1680
gagcgtggcc aagaagcacc caaagacctg ggtgcactac atcgccgccg aggaggagga   1740
ttgggattac gccccactgg tgctggcccc tgatgatcgg agctacaaga gccagtacct   1800
gaacaacgga ccacgcgga tcggacggaa gtacaaaaaa gtgcggttca tggcctacac   1860
cgatgagacc ttcaagaccc gggaggcat ccagcacgag agcggaatcc tgggaccact   1920
gctgtacgga gaggtgggag ataccctgct gatcatcttc aagaaccagg ccagccggcc   1980
atacaacatc tacccacacg gaatcaccga tgtgcggcca ctgtacagcc ggcggctgcc   2040
aaagggagtg aagcacctga aggatttccc aatcctgcca ggagagatct tcaagtacaa   2100
gtggacagtg acagtggagg atggaccaac caagtctgat ccaagatgcc tgaccagata   2160
ctacagcagc tttgtgaaca tggagagaga cctggcctct ggactgattg gaccactgct   2220
gatctgctac aaggagtctg tggatcagag aggaaaccag atcatgtctg ataagagaaa   2280
tgtgatcctg ttctctgtgt ttgatgagaa cagaagctgg tacctgacag agaacatcca   2340
gagattcctg ccaaacccag ccggagtgca gctggaggat ccagagttcc aggccagcaa   2400
catcatgcac agcatcaacg gatacgtgtt cgatagcctg cagctgagcg tgtgcctgca   2460
cgaggtggcc tattggtata tcctgagcat cggagcccag accgatttcc tgagcgtgtt   2520
cttcagcgga tacaccttca gcacaagat ggtgtacgag gatacctga ccctgttccc   2580
attctccgga gagaccgtgt tcatgagcat ggagaaccca ggactgtgga tcctgggatg   2640
ccacaactct gatttcagaa acagaggaat gactgccctg ctgaaagtgt ccagctgtga   2700
taagaacact ggagattact atgaggatag ctatgaggat atctctgcct acctgctgag   2760
caagaacaat gccattgagc caagaagctt cagccagaac ccaccagtgc tgaagagaca   2820
ccagagagag atcaccagaa ccaccctgca gtctgatcag gaggagattg attatgatga   2880
taccatctct gtggagatga agaaggagga ttttgatatc tatgatgagg atgagaacca   2940
gagcccaaga agcttccaga agaagaccag acactactc atcgctgcag tggagagact   3000
gtgggattat ggaatgagca gcagcccaca cgtgctgaga aacagagccc agagcggatc   3060
tgtgccacag ttcaagaagg tggtgttcca ggagttcacc gatggaagct tcacccagcc   3120
actgtaccgg ggagagctga acgagcacct gggactgctg ggaccataca tccgggccga   3180
ggtggaggat aacatcatgg tgaccttccg gaaccaggcc agccggccat acagcttcta   3240
```

```
cagcagcctg atcagctacg aggaggatca gcggcaggga gccgagccac ggaagaactt   3300
cgtgaagcca aacgagacca agacctactt ctggaaggtg cagcaccaca tggcccccaac  3360 caaggatgag ttcgattgca aggcctgggc ctacttcagc gatgtggatc tggagaagga   3420
tgtgcacagc ggactgatcg gaccactgct ggtgtgccac accaacaccc tgaacccagc   3480
ccacggacgg caggtgaccg tgcaggagtt cgccctgttc ttcaccatct tcgatgagac   3540
caagagctgg tacttcaccg agaacatgga gcggaactgc cgggcccctt gcaacatcca   3600
gatggaggat ccaaccttca aggagaacta ccggttccac gccatcaacg atacatcat   3660 ggataccctg ccaggactgg tgatggccca ggatcagcgg atccggtggt acctgctgag   3720
catgggaagc aacgagaaca tccacagcat ccacttcagc ggacacgtgt tcaccgtgcg   3780
gaagaaggag gagtacaaga tggccctgta caacctgtac ccaggagtgt tcgagaccgt   3840
ggagatgctg ccaagcaagg ccggaatctg gcgggtggag tgcctgatcg agagcacct    3900 gcacgccgga atgagcaccc tgttcctggt gtacagcaac aagtgccaga ccccactggg   3960
aatggccagc ggacacatcc gggatttcca gatcaccgcc agcggacagt acggacagtg   4020 ggcccccaaag ctggcccggc tgcactacag cggaagcatc aacgcctgga gcaccaagga  4080
gccattcagc tggatcaaag tggatctgct ggccccaatg atcatccacg aatcaagac    4140 ccagggagcc cggcagaagt tcagcagcct gtacatcagc cagttcatca tcatgtacag   4200
cctggatgga aagaagtggc agacctaccg gggaaacagc accggaaccc tgatggtgtt   4260
cttcggaaac gtggatagca gcggaatcaa gcacaacatc ttcaacccac caatcatcgc   4320
ccgatacatc cggctgcacc caacccacta cagcatcaga agcaccctgc ggatggagct   4380
gatgggatgt gatctgaaca gctgctccat gccactggga atggagagca aggccatcag   4440
cgatgcccag atcaccgcca gcagctactt caccaacatg ttcgccacct ggagcccaag   4500
caaggcccgg ctgcacctgc agggacggag caacgcctgg cggccacagg tgaataaccc   4560
aaaggagtgg ctgcaggtgg atttccagaa gaccatgaag gtgaccggag tgaccaccca   4620
gggagtgaag agcctgctga ctagcatgta tgtgaaggag ttcctgatca gcagcagcca   4680
ggatggacac cagtggaccc tgttcttcca gaacggaaag gtgaaggtgt tccagggaaa   4740
ccaggatagc ttcaccccag tggtgaacag cctggatcca ccactgctga cccgatacct   4800
gcggatccac ccacagagct gggtgcacca gatcgccctg agaatggagg tgctgggatg   4860
cgaggcccag gatctgtact gatgagcatg caataaagtc tgagtgggcg gcagcctgtg   4920
tgtgcctggg ttctctctgt cccggaatgt gcaaacaatg gaggtgctcg agtagataag   4980
tagcatggcg ggttaatcat taactacaag gaaccctag tgatggagtt ggccactccc   5040
tctctgcgcg ctcgctcgct cactgaggcc gggcgaccaa aggtcgcccg acgcccgggc   5100
tttgcccggg cggcctcagt gagcgagcga gcgcgcagcc ttaattaacc taattcactg   5160
gccgtcgttt tacaacgtcg tgactgggaa accctggcg ttaccaact taatcgcctt    5220 gcagcacatc cccctttcgc cagctggcgt aatagcgaag aggcccgcac cgatcgccct   5280
tcccaacagt tgcgcagcct gaatggcgaa tgggacgcgc cctgtagcgg cgcattaagc   5340
gcggcgggtg tggtggttac gcgcagcgtg accgctacac ttgccagcgc cctagcgccc   5400
gctcctttcg ctttcttccc ttcctttctc gccacgttcg ccggctttcc ccgtcaagct   5460
ctaaatcggg ggctcccttt agggttccga tttagtgctt tacggcacct cgaccccaaa   5520
aaacttgatt agggtgatgg ttcacgtagt gggccatcgc cctgatagac ggtttttcgc   5580
cctttgacgt tggagtccac gttctttaat agtggactct tgttccaaac tggaacaaca   5640
```

```
ctcaacccta tctcggtcta ttcttttgat ttataaggga ttttgccgat ttcggcctat    5700
tggttaaaaa atgagctgat ttaacaaaaa tttaacgcga atttaacaa aatattaacg     5760 cttacaattt aggtggcact tttcggggaa atgtgcgcgg aacccctatt tgtttatttt    5820
tctaaataca ttcaaatatg tatccgctca tgagacaata accctgataa atgcttcaat   5880
aatattgaaa aaggaagagt atgagtattc aacatttccg tgtcgccctt attcccttt    5940 ttgcggcatt ttgccttcct gttttgctc acccagaaac gctggtgaaa gtaaaagatg    6000
ctgaagatca gttgggtgca cgagtgggtt acatcgaact ggatctcaac agcggtaaga   6060
tccttgagag ttttcgcccc gaagaacgtt ttccaatgat gagcactttt aaagttctgc   6120
tatgtggcgc ggtattatcc cgtattgacg ccgggcaaga gcaactcggt cgccgcatac   6180
actattctca gaatgacttg gttgagtact caccagtcac agaaaagcat cttacggatg   6240
gcatgacagt aagagaatta tgcagtgctg ccataaccat gagtgataac actgcggcca   6300
acttacttct gacaacgatc ggaggaccga aggagctaac cgcttttttg cacaacatgg   6360
gggatcatgt aactcgcctt gatcgttggg aaccggagct gaatgaagcc ataccaaacg   6420
acgagcgtga caccacgatg cctgtagcaa tggcaacaac gttgcgcaaa ctattaactg   6480
gcgaactact tactctagct tcccggcaac aattaataga ctggatggag gcggataaag   6540
ttgcaggacc acttctgcgc tcggcccttc cggctggctg gtttattgct gataaatctg   6600
gagccggtga gcgtgggtct cgcggtatca ttgcagcact ggggccagat ggtaagccct   6660
cccgtatcgt agttatctac acgacgggga gtcaggcaac tatggatgaa cgaaatagac   6720
agatcgctga gataggtgcc tcactgatta agcattggta actgtcagac caagtttact   6780
catatatact ttagattgat ttaaaacttc attttaatt taaaaggatc taggtgaaga   6840
tcctttttga taatctcatg accaaaatcc cttaacgtga gttttcgttc cactgagcgt   6900 cagacccgt agaaaagatc aaaggatctt cttgagatcc ttttttctg cgcgtaatct    6960 gctgcttgca acaaaaaaa ccaccgctac cagcggtggt ttgtttgccg gatcaagagc    7020
taccaactct ttttccgaag gtaactggct tcagcagagc gcagatacca atactgttc    7080 ttctagtgta gccgtagtta ggccaccact tcaagaactc tgtagcaccg cctacatacc   7140
tcgctctgct aatcctgtta ccagtggctg ctgccagtgg cgataagtcg tgtcttaccg   7200
ggttggactc aagacgatag ttaccggata aggcgcagcg tcgggctga acggggggtt    7260 cgtgcacaca gcccagcttg gagcgaacga cctacaccga actgagatac ctacagcgtg   7320
agctatgaga aagcgccacg cttcccgaag ggagaaaggc ggacaggtat ccggtaagcg   7380
gcagggtcgg aacaggagag cgcacgaggg agcttccagg gggaaacgcc tggtatcttt   7440
atagtcctgt cgggtttcgc cacctctgac ttgagcgtcg atttttgtga tgctcgtcag   7500
gggggcggag cctatggaaa aacgccagca acgcggcctt tttacggttc ctggcctttt   7560
gctggccttt tgctcacatg ttctttcctg cgttatcccc tgattctgtg ataaccgta    7620 ttaccgcctt tgagtgagct gataccgctc gccgcagccg aacgaccgag cgcagcgagt   7680
cagtgagcga ggaagcggaa gagcgcccaa tacgcaaacc gcctctcccc gcgcgttggc   7740
cgattcatta atgcagctgg cacgacaggt ttcccgactg gaaagcgggc agtgagcgca   7800
acgcaattaa tgtgagttag ctcactcatt aggcacccca ggctttacac tttatgcttc   7860
cggctcgtat gttgtgtgga attgtgagcg gataacaatt tcacacagga aacagctatg   7920
accatgatta cgccagattt aattaagg                                       7948
```

<210> SEQ ID NO 16
<211> LENGTH: 8032
<212> TYPE: DNA
<213> ORGANISM: Artificial Sequence
<220> FEATURE:
<223> OTHER INFORMATION: constructed sequence

<400> SEQUENCE: 16

| | | | | | |
|---|---|---|---|---|---|
| ctgcgcgctc | gctcgctcac | tgaggccgcc | cgggcaaagc | ccgggcgtcg | ggcgaccttt | 60 |
| ggtcgcccgg | cctcagtgag | cgagcgagcg | cgcagagagg | gagtggccaa | ctccatcact | 120 |
| aggggttcct | tgtagttaat | gattaacccg | ccatgctact | tatctactta | agctacctcg | 180 |
| tgatcgcccg | gcccctgttc | aaacatgtcc | taatactctg | tctctgcaag | ggtcatcagt | 240 |
| agttttccat | cttactcaac | atcctcccag | tgaggttaat | ttttaaactg | tttgctctgg | 300 |
| ttaataatct | caggaggtta | atttttaaac | tgtttgctct | ggttaataat | ctcagggaat | 360 |
| tctggacaca | ggacgctgtg | gtttctgagc | caggggcga | ctcagatccc | agccagtgga | 420 |
| cttagcccct | gtttgctcct | ccgataactg | gggtgacctt | ggttaatatt | caccagcagc | 480 |
| ctcccccgtt | gcccctctgg | atccactgct | taaatacgga | cgaggacagg | gccctgtctc | 540 |
| ctcagcttca | ggcaccacca | ctgacctggg | acagtgaata | gcggccgcca | ccatgcagat | 600 |
| cgagctgagc | acctgcttct | tcctgtgcct | gctgcggttc | tgcttctccg | ccacccggcg | 660 |
| gtactacctg | ggagccgtgg | agctgagctg | ggattacatg | cagagcgatc | tgggagagct | 720 |
| gccagtggat | gcccggttcc | caccacgggt | gccaaagagc | ttcccattca | acaccagcgt | 780 |
| ggtgtacaag | aagaccctgt | tcgtggagtt | caccgatcac | ctgttcaaca | tcgccaagcc | 840 |
| acggccaccc | tggatgggac | tgctgggacc | aaccatccag | gccgaggtgt | acgataccgt | 900 |
| ggtgatcacc | ctgaagaaca | tggcctctca | tcctgtgtcc | ctgcacgccg | tgggagtgag | 960 |
| ctactggaag | gccagcgagg | gagccgagta | cgatgatcag | accagccagc | gggagaagga | 1020 |
| ggatgataag | gtgttcccag | gaggaagcca | cacctacgtg | tggcaggtgc | tgaaggagaa | 1080 |
| cggaccaatg | gccagcgatc | cactgtgcct | gacctacagc | tacctgagcc | acgtggatct | 1140 |
| ggtgaaggat | ctgaacagcg | gactgatcgg | agccctgctg | gtgtgccggg | agggaagcct | 1200 |
| ggccaaggag | aagacccaga | ccctgcacaa | gttcatcctg | ctgttcgccg | tgttcgatga | 1260 |
| gggaaagagc | tggcacagcg | agaccaagaa | cagcctgatg | caggatcggg | atgccgccag | 1320 |
| cgcccgggcc | tggccaaaga | tgcacaccgt | gaacggatac | gtgaaccgga | gcctgccagg | 1380 |
| actgatcgga | tgccaccgga | agagcgtgta | ctggcacgtg | atcggaatgg | gaaccacccc | 1440 |
| agaggtgcac | tctatcttcc | tggagggaca | cacctttctg | gtgcggaacc | accggcaggc | 1500 |
| cagcctggag | atcagcccaa | tcaccttcct | gaccgcccag | accctgctga | tggatctggg | 1560 |
| acagttcctg | ctgttctgcc | atatcagcag | ccaccagcac | gatggaatgg | aggcctacgt | 1620 |
| gaaggtggat | agctgcccag | aggagccaca | gctgcggatg | aagaacaacg | aggaggccga | 1680 |
| ggattacgat | gatgatctga | ccgatagcga | gatggatgtg | gtgcggttcg | atgatgataa | 1740 |
| cagcccaagc | ttcatccaga | tccggagcgt | ggccaagaag | cacccaaaga | cctgggtgca | 1800 |
| ctacatcgcc | gccgaggagg | aggattggga | ttacgcccca | ctggtgctgg | ccctgatga | 1860 |
| tcggagctac | aagagccagt | acctgaacaa | cggaccacag | cggatcggac | ggaagtacaa | 1920 |
| aaaagtgcgg | ttcatggcct | acaccgatga | gaccttcaag | acccgggagg | ccatccagca | 1980 |
| cgagagcgga | atcctgggac | cactgctgta | cggagaggtg | ggagatacccc | tgctgatcat | 2040 |
| cttcaagaac | caggccagcc | ggccatacaa | catctaccca | cacggaatca | ccgatgtgcg | 2100 |

```
gccactgtac agccggcggc tgccaaaggg agtgaagcac ctgaaggatt tcccaatcct    2160
gccaggagag atcttcaagt acaagtggac agtgacagtg gaggatggac caaccaagtc    2220
tgatccaaga tgcctgacca gatactacag cagctttgtg aacatggaga gagacctggc    2280
ctctggactg attggaccac tgctgatctg ctacaaggga tctgtggatc agagaggaaa    2340
ccagatcatg tctgataaga gaaatgtgat cctgttctct gtgtttgatg agaacagaag    2400
ctggtacctg acagagaaca tccagagatt cctgccaaac ccagccggag tgcagctgga    2460
ggatccagag ttccaggcca gcaacatcat gcacagcatc aacggatacg tgttcgatag    2520
cctgcagctg agcgtgtgcc tgcacagagg ggcctattgg tatatcctga gcatcggagc    2580
ccagaccgat ttcctgagcg tgttcttcag cggatacacc ttcaagcaca agatggtgta    2640
cgaggatacc ctgaccctgt tcccattctc cggagagacc gtgttcatga gcatggagaa    2700
cccaggactg tggatcctgg gatgccacaa ctctgatttc agaaacagag aatgactgc    2760 cctgctgaaa gtgtccagct gtgataagaa cactggagat tactatgagg atagctatga    2820
ggatatctct gcctacctgc tgagcaagaa caatgccatt gagccaagaa gcttcagcca    2880
gaacccacca gtgctgaaga gacaccagag agagatcacc agaaccaccc tgcagtctga    2940
tcaggaggag attgattatg atgataccat ctctgtggag atgaagaagg aggattttga    3000
tatctatgat gaggatgaga accagagccc aagaagcttc cagaagaaga ccagacacta    3060
cttcatcgct gcagtggaga gactgtggga ttatggaatg agcagcagcc cacacgtgct    3120
gagaaacaga gcccagagcg gatctgtgcc acagttcaag aaggtggtgt tccaggagtt    3180
caccgatgga agcttcaccc agccactgta ccggggagag ctgaacgagc acctgggact    3240
gctgggacca tacatccggg ccgaggtgga ggataacatc atggtgacct tccggaacca    3300
ggccagccgg ccatacagct tctacagcag cctgatcagc tacgaggagg atcagcggca    3360
gggagccgag ccacggaaga acttcgtgaa gccaaacgag accaagacct acttctggaa    3420
ggtgcagcac cacatggccc caaccaagga tgagttcgat tgcaaggcct gggcctactt    3480
cagcgatgtg gatctggaga aggatgtgca cagcggactg atcggaccac tgctggtgtg    3540
ccacaccaac accctgaacc cagccacacg acggcaggtg accgtgcagg agttcgccct    3600
gttcttcacc atcttcgatg agaccaagag ctggtacttc accgagaaca tggagcggaa    3660
ctgccgggcc ccttgcaaca tccagatgga ggatccaacc ttcaaggaga actaccggtt    3720
ccacgccatc aacggataca tcatggatac cctgccagga ctggtgatgg cccaggatca    3780
gcggatccgt tggtacctgc tgagcatggg aagcaacgag aacatccaca gcatccactt    3840
cagcggacac gtgttcaccg tgcggaagaa ggaggagtac aagatggccc tgtacaacct    3900
gtacccagga gtgttcgaga ccgtggagat gctgccaagc aaggccggaa tctggcgggt    3960
ggagtgcctg atcggagagc acctgcacgc cggaatgagc accctgttcc tggtgtacag    4020
caacaagtgc cagaccccac tgggaatggc cagcggacac atccgggatt ccagatcac    4080 cgccagcgga cagtacggac agtgggcccc aaagctggcc cggctgcact acagcggaag    4140
catcaacgcc tggagcacca aggagccatt cagctggatc aaagtggatc tgctggcccc    4200
aatgatcatc cacggaatca agacccaggg agccgcgcag aagttcagca gcctgtacat    4260
cagccagttc atcatcatgt acagcctgga tgaaagaag tggcagacct accggggaaa    4320
cagcaccgga accctgatgg tgttcttcgg aaacgtggat agcagcggaa tcaagcacaa    4380
catcttcaac ccaccaatca tcgcccgata catccggctg cacccaaccc actacagcat    4440
```

| | | | | | |
|---|---|---|---|---|---|
| cagaagcacc | ctgcggatgg | agctgatggg | atgtgatctg | aacagctgct | ccatgccact | 4500 |
| gggaatggag | agcaaggcca | tcagcgatgc | ccagatcacc | gccagcagct | acttcaccaa | 4560 |
| catgttcgcc | acctggagcc | caagcaaggc | ccggctgcac | ctgcagggac | ggagcaacgc | 4620 |
| ctggcggcca | caggtgaata | acccaaagga | gtggctgcag | gtggatttcc | agaagaccat | 4680 |
| gaaggtgacc | ggagtgacca | cccagggagt | gaagagcctg | ctgactagca | tgtatgtgaa | 4740 |
| ggagttcctg | atcagcagca | gccaggatgg | acaccagtgg | accctgttct | tccagaacgg | 4800 |
| aaaggtgaag | gtgttccagg | gaaaccagga | tagcttcacc | ccagtggtga | acagcctgga | 4860 |
| tccaccactg | ctgacccgat | acctgcggat | ccacccacag | agctgggtgc | accagatcgc | 4920 |
| cctgagaatg | gaggtgctgg | gatgcgaggc | ccaggatctg | tactgatgag | catgcaataa | 4980 |
| agtctgagtg | ggcggcagcc | tgtgtgtgcc | tgggttctct | ctgtcccgga | atgtgcaaac | 5040 |
| aatggaggtg | ctcgagtaga | taagtagcat | ggcgggttaa | tcattaacta | caaggaaccc | 5100 |
| ctagtgatgg | agttgccac | tccctctctg | cgcgctcgct | cgctcactga | ggccgggcga | 5160 |
| ccaaaggtcg | cccgacgccc | gggctttgcc | cggcggcct | cagtgagcga | gcgagcgcgc | 5220 |
| agccttaatt | aacctaattc | actggccgtc | gttttacaac | gtcgtgactg | ggaaaaccct | 5280 |
| ggcgttaccc | aacttaatcg | ccttgcagca | catcccccctt | cgccagctg | gcgtaatagc | 5340 |
| gaagaggccc | gcaccgatcg | cccttcccaa | cagttgcgca | gcctgaatgg | cgaatgggac | 5400 |
| gcgccctgta | gcgcgcatt | aagcgcggcg | ggtgtggtgg | ttacgcgcag | cgtgaccgct | 5460 |
| acacttgcca | gcgccctagc | gcccgctcct | ttcgctttct | tcccttcctt | tctcgccacg | 5520 |
| ttcgccggct | ttccccgtca | agctctaaat | cgggggctcc | ctttagggtt | ccgatttagt | 5580 |
| gctttacggc | acctcgaccc | caaaaaactt | gattagggtg | atggttcacg | tagtgggcca | 5640 |
| tcgccctgat | agacggtttt | tcgccctttg | acgttggagt | ccacgttctt | taatagtgga | 5700 |
| ctcttgttcc | aaactggaac | aacactcaac | cctatctcgg | tctattcttt | tgatttataa | 5760 |
| gggattttgc | cgatttcggc | ctattggtta | aaaaatgagc | tgatttaaca | aaaatttaac | 5820 |
| gcgaatttta | acaaaatatt | aacgcttaca | atttaggtgg | cacttttcgg | ggaaatgtgc | 5880 |
| gcggaacccc | tatttgttta | tttttctaaa | tacattcaaa | tatgtatccg | ctcatgagac | 5940 |
| aataaccctg | ataaatgctt | caataatatt | gaaaaaggaa | gagtatgagt | attcaacatt | 6000 |
| tccgtgtcgc | ccttattccc | ttttttgcgg | cattttgcct | tcctgttttt | gctcacccag | 6060 |
| aaacgctggt | gaaagtaaaa | gatgctgaag | atcagttggg | tgcacgagtg | ggttacatcg | 6120 |
| aactggatct | caacagcggt | aagatccttg | agagttttcg | ccccgaagaa | cgttttccaa | 6180 |
| tgatgagcac | ttttaaagtt | ctgctatgtg | gcgcggtatt | atcccgtatt | gacgccgggc | 6240 |
| aagagcaact | cggtcgccgc | atacactatt | ctcagaatga | cttggttgag | tactcaccag | 6300 |
| tcacagaaaa | gcatcttacg | gatggcatga | cagtaagaga | attatgcagt | gctgccataa | 6360 |
| ccatgagtga | taacactgcg | gccaacttac | ttctgacaac | gatcggagga | ccgaaggagc | 6420 |
| taaccgcttt | tttgcacaac | atgggggatc | atgtaactcg | ccttgatcgt | tgggaaccgg | 6480 |
| agctgaatga | agccatacca | aacgacgagc | gtgacaccac | gatgcctgta | gcaatggcaa | 6540 |
| caacgttgcg | caaactatta | actggcgaac | tacttactct | agcttcccgg | caacaattaa | 6600 |
| tagactggat | ggaggcggat | aaagttgcag | gaccacttct | gcgctcggcc | cttccggctg | 6660 |
| gctggtttat | tgctgataaa | tctggagccg | gtgagcgtgg | gtctcgcggt | atcattgcag | 6720 |
| cactggggcc | agatggtaag | ccctcccgta | tcgtagttat | ctacacgacg | gggagtcagg | 6780 |
| caactatgga | tgaacgaaat | agacagatcg | ctgagatagg | tgcctcactg | attaagcatt | 6840 |

-continued

```
ggtaactgtc agaccaagtt tactcatata tactttagat tgatttaaaa cttcattttt      6900
aatttaaaag gatctaggtg aagatccttt ttgataatct catgaccaaa atcccttaac      6960
gtgagttttc gttccactga gcgtcagacc ccgtagaaaa gatcaaagga tcttcttgag      7020 atccttttt tctgcgcgta atctgctgct tgcaaacaaa aaaaccaccg ctaccagcgg       7080
tggtttgttt gccggatcaa gagctaccaa ctcttttttcc gaaggtaact ggcttcagca    7140
gagcgcagat accaaatact gttcttctag tgtagccgta gttaggccac cacttcaaga     7200
actctgtagc accgcctaca tacctcgctc tgctaatcct gttaccagtg gctgctgcca     7260
gtggcgataa gtcgtgtctt accgggttgg actcaagacg atagttaccg gataaggcgc     7320
agcggtcggg ctgaacgggg ggttcgtgca cacagcccag cttggagcga acgacctaca    7380
ccgaactgag atacctacag cgtgagctat gagaaagcgc cacgcttccc gaagggagaa    7440
aggcggacag gtatccggta agcggcaggg tcggaacagg agagcgcacg agggagcttc    7500
cagggggaaa cgcctggtat ctttatagtc ctgtcgggtt tcgccacctc tgacttgagc    7560
gtcgattttt gtgatgctcg tcagggggc ggagcctatg gaaaaacgcc agcaacgcgg     7620 ccttttttacg gttcctggcc ttttgctggc cttttgctca catgttcttt cctgcgttat    7680
cccctgattc tgtggataac cgtattaccg cctttgagtg agctgatacc gctcgccgca    7740
gccgaacgac cgagcgcagc gagtcagtga gcgaggaagc ggaagagcgc ccaatacgca    7800
aaccgcctct ccccgcgcgt tggccgattc attaatgcag ctggcacgac aggtttcccg    7860
actggaaagc gggcagtgag cgcaacgcaa ttaatgtgag ttagctcact cattaggcac    7920
cccaggcttt acactttatg cttccggctc gtatgttgtg tggaattgtg agcggataac    7980
aatttcacac aggaaacagc tatgaccatg attacgccag atttaattaa gg             8032
```

<210> SEQ ID NO 17  
<211> LENGTH: 738  
<212> TYPE: PRT  
<213> ORGANISM: Unknown  
<220> FEATURE:  
<223> OTHER INFORMATION: AAVhu.37 capsid
<400> SEQUENCE: 17

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Thr Gly Ile
```

-continued

```
            145                 150                 155                 160
        Gly Lys Lys Gly Gln Gln Pro Ala Lys Lys Arg Leu Asn Phe Gly Gln
                        165                 170                 175
        Thr Gly Asp Ser Glu Ser Val Pro Asp Pro Gln Pro Ile Gly Glu Pro
                        180                 185                 190
        Pro Ala Gly Pro Ser Gly Leu Gly Ser Gly Thr Met Ala Ala Gly Gly
                        195                 200                 205
        Gly Ala Pro Met Ala Asp Asn Asn Glu Gly Ala Asp Gly Val Gly Ser
                        210                 215                 220
        Ser Ser Gly Asn Trp His Cys Asp Ser Thr Trp Leu Gly Asp Arg Val
        225                 230                 235                 240
        Ile Thr Thr Ser Thr Arg Thr Trp Ala Leu Pro Thr Tyr Asn Asn His
                        245                 250                 255
        Leu Tyr Lys Gln Ile Ser Asn Gly Thr Ser Gly Gly Ser Thr Asn Asp
                        260                 265                 270
        Asn Thr Tyr Phe Gly Tyr Ser Thr Pro Trp Gly Tyr Phe Asp Phe Asn
                        275                 280                 285
        Arg Phe His Cys His Phe Ser Pro Arg Asp Trp Gln Arg Leu Ile Asn
                        290                 295                 300
        Asn Asn Trp Gly Phe Arg Pro Lys Arg Leu Ser Phe Lys Leu Phe Asn
        305                 310                 315                 320
        Ile Gln Val Lys Glu Val Thr Gln Asn Glu Gly Thr Lys Thr Ile Ala
                        325                 330                 335
        Asn Asn Leu Thr Ser Thr Ile Gln Val Phe Thr Asp Ser Glu Tyr Gln
                        340                 345                 350
        Leu Pro Tyr Val Leu Gly Ser Ala His Gln Gly Cys Leu Pro Pro Phe
                        355                 360                 365
        Pro Ala Asp Val Phe Met Ile Pro Gln Tyr Gly Tyr Leu Thr Leu Asn
                        370                 375                 380
        Asn Gly Ser Gln Ala Val Gly Arg Ser Ser Phe Tyr Cys Leu Glu Tyr
        385                 390                 395                 400
        Phe Pro Ser Gln Met Leu Arg Thr Gly Asn Asn Phe Glu Phe Ser Tyr
                        405                 410                 415
        Thr Phe Glu Asp Val Pro Phe His Ser Ser Tyr Ala His Ser Gln Ser
                        420                 425                 430
        Leu Asp Arg Leu Met Asn Pro Leu Ile Asp Gln Tyr Leu Tyr Tyr Leu
                        435                 440                 445
        Ser Arg Thr Gln Ser Thr Gly Gly Thr Gln Gly Thr Gln Gln Leu Leu
        450                 455                 460
        Phe Ser Gln Ala Gly Pro Ala Asn Met Ser Ala Gln Ala Lys Asn Trp
        465                 470                 475                 480
        Leu Pro Gly Pro Cys Tyr Arg Gln Gln Arg Val Ser Thr Thr Leu Ser
                        485                 490                 495
        Gln Asn Asn Asn Ser Asn Phe Ala Trp Thr Gly Ala Thr Lys Tyr His
                        500                 505                 510
        Leu Asn Gly Arg Asp Ser Leu Val Asn Pro Gly Val Ala Met Ala Thr
                        515                 520                 525
        His Lys Asp Asp Glu Glu Arg Phe Phe Pro Ser Ser Gly Val Leu Met
                        530                 535                 540
        Phe Gly Lys Gln Gly Ala Gly Arg Asp Asn Val Asp Tyr Ser Ser Val
        545                 550                 555                 560
        Met Leu Thr Ser Glu Glu Ile Lys Thr Thr Asn Pro Val Ala Thr
                        565                 570                 575
```

```
Glu Gln Tyr Gly Val Ala Asp Asn Leu Gln Gln Thr Asn Thr Gly
            580                 585                 590

Pro Ile Val Gly Asn Val Asn Ser Gln Gly Ala Leu Pro Gly Met Val
            595                 600                 605

Trp Gln Asn Arg Asp Val Tyr Leu Gln Gly Pro Ile Trp Ala Lys Ile
            610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
            645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
            725                 730                 735

Asn Leu

<210> SEQ ID NO 18
<211> LENGTH: 738
<212> TYPE: PRT
<213> ORGANISM: Unknown
<220> FEATURE:
<223> OTHER INFORMATION: AAVrh.10 capsid

<400> SEQUENCE: 18

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
            165                 170                 175

Thr Gly Asp Ser Glu Ser Val Pro Asp Pro Gln Pro Ile Gly Glu Pro
            180                 185                 190
```

```
Pro Ala Gly Pro Ser Gly Leu Gly Ser Gly Thr Met Ala Gly Gly
            195                 200                 205
Gly Ala Pro Met Ala Asp Asn Asn Glu Gly Ala Asp Gly Val Gly Ser
210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Asn Gly Thr Ser Gly Gly Ser Thr Asn Asp
            260                 265                 270
Asn Thr Tyr Phe Gly Tyr Ser Thr Pro Trp Gly Tyr Phe Asp Phe Asn
        275                 280                 285
Arg Phe His Cys His Phe Ser Pro Arg Asp Trp Gln Arg Leu Ile Asn
    290                 295                 300
Asn Asn Trp Gly Phe Arg Pro Lys Arg Leu Asn Phe Lys Leu Phe Asn
305                 310                 315                 320
Ile Gln Val Lys Glu Val Thr Gln Asn Glu Gly Thr Lys Thr Ile Ala
                325                 330                 335
Asn Asn Leu Thr Ser Thr Ile Gln Val Phe Thr Asp Ser Glu Tyr Gln
            340                 345                 350
Leu Pro Tyr Val Leu Gly Ser Ala His Gln Gly Cys Leu Pro Pro Phe
        355                 360                 365
Pro Ala Asp Val Phe Met Ile Pro Gln Tyr Gly Tyr Leu Thr Leu Asn
    370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Glu Phe Ser Tyr
                405                 410                 415
Gln Phe Glu Asp Val Pro Phe His Ser Ser Tyr Ala His Ser Gln Ser
            420                 425                 430
Leu Asp Arg Leu Met Asn Pro Leu Ile Asp Gln Tyr Leu Tyr Tyr Leu
        435                 440                 445
Ser Arg Thr Gln Ser Thr Gly Gly Thr Ala Gly Thr Gln Gln Leu Leu
    450                 455                 460
Phe Ser Gln Ala Gly Pro Asn Asn Met Ser Ala Gln Ala Lys Asn Trp
465                 470                 475                 480
Leu Pro Gly Pro Cys Tyr Arg Gln Gln Arg Val Ser Thr Thr Leu Ser
                485                 490                 495
Gln Asn Asn Asn Ser Asn Phe Ala Trp Thr Gly Ala Thr Lys Tyr His
            500                 505                 510
Leu Asn Gly Arg Asp Ser Leu Val Asn Pro Gly Val Ala Met Ala Thr
        515                 520                 525
His Lys Asp Asp Glu Glu Arg Phe Phe Pro Ser Ser Gly Val Leu Met
    530                 535                 540
Phe Gly Lys Gln Gly Ala Gly Lys Asp Asn Val Asp Tyr Ser Ser Val
545                 550                 555                 560
Met Leu Thr Ser Glu Glu Glu Ile Lys Thr Thr Asn Pro Val Ala Thr
                565                 570                 575
Glu Gln Tyr Gly Val Val Ala Asp Asn Leu Gln Gln Asn Ala Ala
            580                 585                 590
Pro Ile Val Gly Ala Val Asn Ser Gln Gly Ala Leu Pro Gly Met Val
        595                 600                 605
Trp Gln Asn Arg Asp Val Tyr Leu Gln Gly Pro Ile Trp Ala Lys Ile
```

```
                610                615                620
Pro His Thr Asp Gly Asn Phe His Pro Ser Pro Leu Met Gly Gly Phe
625                 630                635                640

Gly Leu Lys His Pro Pro Gln Ile Leu Ile Lys Asn Thr Pro Val
                645                650                655

Pro Ala Asp Pro Pro Thr Thr Phe Ser Gln Ala Lys Leu Ala Ser Phe
                660                665                670

Ile Thr Gln Tyr Ser Thr Gly Gln Val Ser Val Glu Ile Glu Trp Glu
            675                680                685

Leu Gln Lys Glu Asn Ser Lys Arg Trp Asn Pro Glu Ile Gln Tyr Thr
        690                695                700

Ser Asn Tyr Tyr Lys Ser Thr Asn Val Asp Phe Ala Val Asn Thr Asp
705                710                715                720

Gly Thr Tyr Ser Glu Pro Arg Pro Ile Gly Thr Arg Tyr Leu Thr Arg
                725                730                735

Asn Leu

<210> SEQ ID NO 19
<211> LENGTH: 4371
<212> TYPE: DNA
<213> ORGANISM: Artificial Sequence
<220> FEATURE:
<223> OTHER INFORMATION: constructed sequence

<400> SEQUENCE: 19
atgcagatcg agctgtctac ctgcttcttc ctgtgcctgc tgcggttctg cttcagcgcc      60
accagacggt actatctggg cgccgtggaa ctgagctggg actacatgca gagcgacctg     120
ggcgagctgc ccgtggacgc cagattccct ccaagagtgc ccaagagctt ccccttcaac     180
acctccgtgg tgtacaagaa aaccctgttc gtggaattca ccgaccacct gttcaatatc     240
gccaagccca ccccccctg  gatgggcctg ctgggaccta caattcaggc cgaggtgtac     300
gacaccgtcg tgatcaccct gaagaacatg gccagccacc ccgtgtctct gcacgccgtg     360
ggagtgtcct actggaaggc ctctgagggc gccgagtacg acgatcagac cagccagcgc     420
gagaaagagg acgacaaggt gttccctggc ggcagccaca cctacgtgtg gcaggtgctg     480
aaagaaaacg gccccatggc ctccgaccct ctgtgcctga catacagcta cctgagccac     540
gtggacctcg tgaaggacct gaacagcggc ctgatcggag ccctgctcgt gtgtagagag     600
ggcagcctgg ccaaagagaa aacccagacc ctgcacaagt tcatcctgct gttcgccgtg     660
ttcgacgagg gcaagagctg gcacagcgag acaaagaaca gcctgatgca ggaccgggac     720
gccgcctctg ctagagcctg gcccaaaatg cacaccgtga acggctacgt gaacagaagc     780
ctgcccggac tgatcggctg ccaccggaag tctgtgtact ggcacgtgat cggcatgggc     840
accaccctg  aggtgcacag catctttctg gaaggacaca ctttctcgt  gcggaaccac     900
cggcaggcca gctggaaat  cagccctatc accttcctga ccgccagac  actgctgatg     960
gacctgggcc agtttctgct gttctgccac atcagctccc accagcacga cggcatggaa    1020
gcctacgtga aggtggacag ctgccccgag gaacccagc  tgcggatgaa gaacaacgag    1080
gaagccgagg actacgacga cgacctgacc gacagcgaga tggacgtggt gcgcttcgac    1140
gacgataaca gcccagctt  catccagatc agaagcgtgg ccaagaagca cccaagacc    1200
tgggtgcact atatcgccgc cgaggaagag gactgggatt acgccctct  ggtgctggcc    1260
cccgacgaca agctacaa  gagccagtac ctgaacaacg gcccccagcg gatcggccgg    1320
```

```
aagtataaga aagtgcggtt catggcctac accgacgaga cattcaagac cagagaggcc    1380
atccagcacg agagcggcat cctgggccct ctgctgtatg gcgaagtggg cgacaccctg    1440
ctgatcatct tcaagaacca ggccagcaga ccctacaaca tctaccctca cggcatcacc    1500
gacgtgcggc ccctgtactc tagaaggctg cccaagggcg tgaaacacct gaaggacttc    1560
cccatcctgc ccggcgagat cttcaagtac aagtggaccg tgaccgtgga agatggcccc    1620
accaagagcg accccagatg cctgacacgg tactatagca gcttcgtgaa catggaacgg    1680
gacctggcct ccggcctgat tggcccactg ctgatctgct acaaagaaag cgtggaccag    1740
cggggcaacc agatcatgag cgacaagcgg aacgtgatcc tgtttagcgt gttcgatgag    1800
aaccggtcct ggtatctgac cgagaatatc cagcggttcc tgcccaaccc tgccggcgtg    1860
cagctggaag atcctgagtt ccaggcctcc aacatcatgc actccatcaa tggctatgtg    1920
ttcgacagcc tgcagctgag cgtgtgcctg cacgaggtgg cctactggta catcctgagc    1980
atcggggccc agaccgactt cctgtccgtg ttcttctccg gctacacctt caagcacaag    2040
atggtgtacg aggataccct gaccctgttc ccctttagcg cgaaaccgt gttcatgagc    2100
atggaaaacc ccggcctgtg gatcctgggc tgccacaaca gcgacttccg gaacagaggc    2160
atgaccgccc tgctgaaggt gtccagctgc gacaagaaca ccggcgacta ctacgaggac    2220
agctatgagg acatcagcgc ctacctgctg agcaagaaca acgccatcga gcccagaagc    2280
ttcagccaga ccccccccgt gctgaagcgg caccagagag atcacccg gaccaccctg    2340
cagtccgacc aggaagagat cgattacgac gacaccatca gcgtggaaat gaagaaagaa    2400
gatttcgaca tctacgacga ggacgagaac cagagccccc ggtcctttca gaaaaagacc    2460
cggcactact tcattgccgc tgtggaacgg ctgtgggact acggcatgag cagcagccct    2520
cacgtgctga aaacagggc ccagagcggc agcgtgcccc agttcaagaa agtggtgttc    2580
caggaattca cagacggcag cttcacccag cctctgtacc gcggcgagct gaacgagcac    2640
ctgggactgc tgggccccta tatcagagcc gaagtggaag ataacatcat ggtcaccttc    2700
cggaatcagg cctcccggcc ctacagcttc tacagctccc tgatcagcta cgaagaggac    2760
cagagacagg cgctgagcc ccggaagaac ttcgtgaagc ccaacgagac taagacctac    2820
tttttggaagg tgcagcacca catggcccct acaaaggacg agttcgactg caaggcctgg    2880
gcctacttct ccgacgtgga cctggaaaag gacgtgcact ctgggctgat cggcccctg    2940
ctcgtgtgcc acaccaacac cctgaatccc gcccacggca gacaggtgac agtgcaggaa    3000
ttcgccctgt tcttcaccat cttcgacgaa acaaagagct ggtacttcac cgaaaacatg    3060
gaaagaaact gccgggctcc ctgcaacatc cagatggaag atcccaccttt caaagagaac    3120
taccggttcc acgccatcaa cggctacatc atggacacac tgcccggcct cgtgatggct    3180
caggatcagc ggatccggtg gtatctgctg tccatgggct ccaacgagaa catccacagc    3240
atccacttca gcggccacgt gttcaccgtg cggaaaaaag aagagtacaa aatggccctg    3300
tacaacctgt accctggggt gttcgagaca gtggaaatgc tgcccagcaa ggccggcatc    3360
tggcgggtgg agtgtctgat cggcgagcac ctgcacgctg ggatgagcac actgtttctg    3420
gtgtacagca caagtgcca gacacctctg ggcatggcct ctggccacat ccgggacttt    3480
cagatcacag ccagcggcca gtacggccag tgggcccaa aactggccag actgcactac    3540
agcggcagca tcaacgcctg gtccaccaaa gagcccttca gctggatcaa ggtggacctg    3600
ctggctccca tgatcatcca cggaatcaag acccagggcg ccagacagaa gttcagcagc    3660
ctgtacatca gccagttcat catcatgtac agcctggacg gcaagaagtg cagacctac    3720
```

-continued

```
cggggcaata gcaccggcac cctgatggtg ttcttcggca acgtggactc cagcggcatt      3780
aagcacaaca tcttcaaccc ccccatcatt gcccggtaca tccggctgca ccccacccac      3840
tacagcatcc ggtccaccct gagaatggaa ctgatgggct gcgacctgaa ctcctgctcc      3900
atgcccctgg ggatggaaag caaggccatc tccgacgccc agatcaccgc ctccagctac      3960
ttcaccaaca tgttcgccac ctggtcccca tccaaggccc ggctgcacct gcagggcaga      4020
agcaatgctt ggaggcctca ggtgaacaac cccaaagagt ggctgcaggt ggacttccag      4080
aaaaccatga agtgaccgg cgtgaccacc agggcgtga agtctctgct gacctctatg       4140
tacgtgaaag agttcctgat ctccagcagc aggacggcc accagtggac cctgtttttc      4200
cagaacggca aagtgaaagt gtttcagggg aaccaggact ccttcacccc cgtcgtgaat      4260
agcctggacc ctccactgct gaccagatac ctgcggatcc accctcagag ttgggtgcac      4320
cagattgctc tgcggatgga agtgctggga tgcgaggccc aggacctgta c              4371
```

<210> SEQ ID NO 20
<211> LENGTH: 736
<212> TYPE: PRT
<213> ORGANISM: Unknown
<220> FEATURE:
<223> OTHER INFORMATION: AAV3B capsid

<400> SEQUENCE: 20

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
```

```
            245                 250                 255
Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
                275                 280                 285

Cys His Phe Ser Pro Arg Asp Trp Gln Arg Leu Ile Asn Asn Asn Trp
290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
                370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Asn Arg Thr
                435                 440                 445

Gln Gly Thr Thr Ser Gly Thr Thr Asn Gln Ser Arg Leu Leu Phe Ser
                450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
                500                 505                 510

Gly Arg Asp Ser Leu Val Asn Pro Gly Pro Ala Met Ala Ser His Lys
                515                 520                 525

Asp Asp Glu Glu Lys Phe Phe Pro Met His Gly Asn Leu Ile Phe Gly
530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
                580                 585                 590

Thr Arg Thr Val Asn Asp Gln Gly Ala Leu Pro Gly Met Val Trp Gln
                595                 600                 605

Asp Arg Asp Val Tyr Leu Gln Gly Pro Ile Trp Ala Lys Ile Pro His
                610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
                660                 665                 670
```

```
Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
        690                 695             700

Tyr Asn Lys Ser Val Asn Val Asp Phe Thr Val Asp Thr Asn Gly Val
705             710             715                 720

Tyr Ser Glu Pro Arg Pro Ile Gly Thr Arg Tyr Leu Thr Arg Asn Leu
                725             730             735
```